United States Patent
Berenson et al.

(10) Patent No.: US 11,957,346 B2
(45) Date of Patent: Apr. 16, 2024

(54) FORCE MODULATING DEEP SKIN STAPLES AND INSTRUMENTS

(71) Applicant: KitoTech Medical, Inc., Seattle, WA (US)

(72) Inventors: Ronald J. Berenson, Mercer Island, WA (US); Cheuk Yin Paul Leung, Bellevue, WA (US)

(73) Assignee: KitoTech Medical, Inc., Seattle, WA (US)

( * ) Notice: Subject to any disclaimer, the term of this patent is extended or adjusted under 35 U.S.C. 154(b) by 0 days.

(21) Appl. No.: 18/111,080

(22) Filed: Feb. 17, 2023

(65) Prior Publication Data
US 2023/0263523 A1 Aug. 24, 2023

Related U.S. Application Data

(60) Provisional application No. 63/268,218, filed on Feb. 18, 2022.

(51) Int. Cl.
*A61B 17/072* (2006.01)
*A61B 17/00* (2006.01)

(52) U.S. Cl.
CPC ............... *A61B 17/07207* (2013.01); *A61B 2017/00526* (2013.01); *A61B 2017/07214* (2013.01)

(58) Field of Classification Search
CPC ............................................. A61B 17/07207
See application file for complete search history.

(56) References Cited

U.S. PATENT DOCUMENTS

| | | | |
|---|---|---|---|
| 345,541 | A | 7/1886 | Reiohardt |
| 2,472,009 | A | 5/1949 | Gardner |
| 2,575,205 | A | 11/1951 | Brown |
| 2,619,084 | A | 11/1952 | Brown |
| 2,669,747 | A | 2/1954 | Detaranto |
| 3,068,869 | A | 12/1962 | Hunter et al. |
| 3,473,528 | A | 10/1969 | Mishkin et al. |
| 3,613,679 | A | 10/1971 | Bijou |
| 3,926,193 | A | 12/1975 | Hasson |
| 3,931,821 | A | 1/1976 | Kletschka et al. |

(Continued)

FOREIGN PATENT DOCUMENTS

| | | |
|---|---|---|
| AU | 767122 B2 | 10/2003 |
| AU | 2004200303 A1 | 2/2004 |

(Continued)

OTHER PUBLICATIONS

"U.S. Appl. No. 14/408,244, Examiner Interview Summary dated Nov. 8, 2018", 3 pgs.

(Continued)

*Primary Examiner* — Nathaniel C Chukwurah
(74) *Attorney, Agent, or Firm* — Schwegman Lundberg & Woessner, P.A.

(57) ABSTRACT

A wound closure device in the form of a force modulating deep skin staple. The deep skin staple includes a bridge portion extending along a longitudinal axis to support a first set of staple legs and an opposing second set of staple legs. Each staple leg coupled to the bridge portion via a spring arm. Each staple leg angled towards a middle section of the bridge portion. The staple legs designed to modulate forces with a wound down into the reticular dermis layer when applied to the wound.

24 Claims, 23 Drawing Sheets

(56) References Cited

U.S. PATENT DOCUMENTS

| | | |
|---|---|---|
| 4,430,998 A | 2/1984 | Harvey et al. |
| 4,535,772 A | 8/1985 | Sheehan |
| 4,637,380 A | 1/1987 | Orejola |
| 4,762,260 A | 8/1988 | Richards et al. |
| 4,803,078 A | 2/1989 | Sakai |
| 5,047,047 A | 9/1991 | Yoon |
| 5,234,462 A | 8/1993 | Pavletic |
| 5,531,790 A | 7/1996 | Frechet et al. |
| 5,843,123 A | 12/1998 | Brazeau |
| 5,916,224 A | 6/1999 | Esplin |
| 5,968,097 A | 10/1999 | Frechet et al. |
| 6,168,596 B1 | 1/2001 | Wellisz et al. |
| 6,254,624 B1 | 7/2001 | Oddsen et al. |
| 6,256,533 B1 | 7/2001 | Yuzhakov et al. |
| 6,312,612 B1 | 11/2001 | Sherman et al. |
| 6,334,856 B1 | 1/2002 | Allen et al. |
| 6,379,324 B1 | 4/2002 | Gartstein et al. |
| 6,451,240 B1 | 9/2002 | Sherman et al. |
| 6,471,715 B1 | 10/2002 | Weiss |
| 6,471,903 B2 | 10/2002 | Sherman et al. |
| 6,503,231 B1 | 1/2003 | Prausnitz et al. |
| 6,537,264 B1 | 3/2003 | Cormier et al. |
| 6,565,532 B1 | 5/2003 | Yuzhakov et al. |
| 6,589,202 B1 | 7/2003 | Powell |
| 6,611,707 B1 | 8/2003 | Prausnitz et al. |
| 6,652,478 B1 | 11/2003 | Gartstein et al. |
| 6,712,839 B1 | 3/2004 | Loenne |
| 6,743,211 B1 | 6/2004 | Prausnitz et al. |
| 6,931,277 B1 | 8/2005 | Yuzhakov et al. |
| 6,960,193 B2 | 11/2005 | Rosenberg |
| 7,060,192 B2 | 6/2006 | Yuzhakov et al. |
| 7,144,495 B2 | 12/2006 | Teodorczyk et al. |
| 7,160,312 B2 | 1/2007 | Saadat |
| 7,172,615 B2 | 2/2007 | Morriss et al. |
| 7,226,439 B2 | 6/2007 | Prausnitz et al. |
| 7,344,499 B1 | 3/2008 | Prausnitz et al. |
| 7,416,541 B2 | 8/2008 | Yuzhakov et al. |
| 7,455,681 B2 | 11/2008 | Wilke et al. |
| 7,510,566 B2 | 3/2009 | Jacobs et al. |
| 7,626,070 B2 | 12/2009 | Propp |
| 7,658,728 B2 | 2/2010 | Yuzhakov |
| 7,683,234 B2 | 3/2010 | Gurtner et al. |
| 7,686,829 B2 | 3/2010 | Elliott et al. |
| 7,785,301 B2 | 8/2010 | Yuzhakov |
| 7,806,266 B2 | 10/2010 | Hagino et al. |
| 8,049,058 B2 | 11/2011 | Propp |
| 8,053,624 B2 | 11/2011 | Propp |
| 8,063,263 B2 | 11/2011 | Gurtner et al. |
| 8,157,839 B2 | 4/2012 | Riskin et al. |
| 8,168,850 B2 | 5/2012 | Gurtner et al. |
| 8,183,428 B2 | 5/2012 | Gurtner et al. |
| 8,250,729 B2 | 8/2012 | Lee et al. |
| 8,388,631 B2 | 3/2013 | Oostman, Jr. et al. |
| 8,389,791 B2 | 3/2013 | Gurtner et al. |
| 8,397,973 B1 | 3/2013 | Hausen |
| 8,414,548 B2 | 4/2013 | Yuzhakov |
| 8,540,672 B2 | 9/2013 | Mcallister |
| 8,663,275 B2 | 3/2014 | O'malley et al. |
| 8,771,312 B1 * | 7/2014 | Knodel ............ A61B 17/0644 606/219 |
| 8,777,987 B2 | 7/2014 | Herrmann et al. |
| 8,852,214 B2 | 10/2014 | Kubiak |
| 8,894,683 B2 | 11/2014 | Weadock et al. |
| 9,050,086 B2 | 6/2015 | Belson et al. |
| 9,089,328 B2 | 7/2015 | Belson et al. |
| 9,358,376 B2 | 6/2016 | Altarac |
| 9,392,965 B2 | 7/2016 | Tenney et al. |
| 9,414,840 B2 | 8/2016 | Fleischmann |
| 9,427,309 B2 | 8/2016 | Kubiak et al. |
| 9,855,036 B2 | 1/2018 | Palmer et al. |
| 9,993,620 B2 | 6/2018 | Le et al. |
| 10,219,804 B2 * | 3/2019 | Linder ................ A61B 17/08 |
| 10,492,780 B2 | 12/2019 | Gross et al. |
| 10,751,050 B2 | 8/2020 | Rolandi et al. |
| 10,939,912 B2 | 3/2021 | Leung et al. |
| 11,253,252 B2 * | 2/2022 | Kubiak ............ A61B 17/1146 |
| 2001/0051815 A1 | 12/2001 | Esplin |
| 2002/0082543 A1 | 6/2002 | Park et al. |
| 2002/0133129 A1 | 9/2002 | Arias et al. |
| 2002/0168290 A1 | 11/2002 | Yuzhakov et al. |
| 2002/0193754 A1 | 12/2002 | Cho |
| 2003/0028087 A1 | 2/2003 | Yuzhakov et al. |
| 2003/0028125 A1 | 2/2003 | Yuzhakov et al. |
| 2003/0065360 A1 | 4/2003 | Jacobs et al. |
| 2003/0074021 A1 | 4/2003 | Morriss et al. |
| 2003/0176890 A1 | 9/2003 | Buckman et al. |
| 2003/0212344 A1 | 11/2003 | Yuzhakov et al. |
| 2004/0010276 A1 | 1/2004 | Jacobs et al. |
| 2004/0138705 A1 | 7/2004 | Heino et al. |
| 2004/0260340 A1 | 12/2004 | Jacobs et al. |
| 2005/0049549 A1 | 3/2005 | Wong et al. |
| 2005/0119694 A1 | 6/2005 | Jacobs et al. |
| 2005/0143713 A1 | 6/2005 | Delmore et al. |
| 2005/0148921 A1 | 7/2005 | Hsu |
| 2005/0197699 A1 | 9/2005 | Jacobs et al. |
| 2005/0261631 A1 | 11/2005 | Clarke et al. |
| 2006/0058842 A1 | 3/2006 | Wilke et al. |
| 2006/0093658 A1 | 5/2006 | Sathyan et al. |
| 2006/0228320 A1 | 10/2006 | Minami et al. |
| 2007/0021779 A1 | 1/2007 | Garvin et al. |
| 2007/0191761 A1 | 8/2007 | Boone et al. |
| 2007/0225676 A1 | 9/2007 | Prausnitz et al. |
| 2007/0282374 A1 | 12/2007 | Sogard et al. |
| 2007/0288040 A1 | 12/2007 | Ferree |
| 2007/0293815 A1 | 12/2007 | Chan et al. |
| 2007/0299388 A1 | 12/2007 | Chan et al. |
| 2008/0009825 A1 | 1/2008 | Ringsred et al. |
| 2008/0051723 A1 | 2/2008 | Laermer et al. |
| 2008/0125743 A1 | 5/2008 | Yuzhakov |
| 2008/0183144 A1 | 7/2008 | Trautman et al. |
| 2008/0195035 A1 | 8/2008 | Frederickson et al. |
| 2008/0262543 A1 | 10/2008 | Bangera et al. |
| 2008/0275409 A1 | 11/2008 | Kane et al. |
| 2009/0099437 A1 | 4/2009 | Yuzhakov |
| 2009/0131846 A1 | 5/2009 | Gurtner et al. |
| 2009/0216326 A1 | 8/2009 | Hirpara et al. |
| 2009/0312597 A1 | 12/2009 | Bar et al. |
| 2010/0048744 A1 | 2/2010 | Park et al. |
| 2010/0137679 A1 | 6/2010 | Lashinski et al. |
| 2010/0193997 A1 | 8/2010 | Frederickson et al. |
| 2010/0256568 A1 | 10/2010 | Frederickson et al. |
| 2010/0274283 A1 | 10/2010 | Kirsch et al. |
| 2010/0305473 A1 | 12/2010 | Yuzhakov |
| 2010/0312191 A1 | 12/2010 | Allen et al. |
| 2011/0288565 A1 | 11/2011 | Kubiak et al. |
| 2012/0029434 A1 | 2/2012 | Kobayashi et al. |
| 2012/0046586 A1 | 2/2012 | Gurtner et al. |
| 2012/0184916 A1 | 7/2012 | Kobayashi et al. |
| 2012/0203253 A1 | 8/2012 | Kubiak |
| 2012/0221044 A1 | 8/2012 | Archibald et al. |
| 2013/0123806 A1 | 5/2013 | Howlett et al. |
| 2013/0218083 A1 | 8/2013 | Yuzhakov |
| 2014/0046349 A1 | 2/2014 | Warner et al. |
| 2015/0032204 A1 | 1/2015 | Johansson |
| 2015/0250476 A1 | 9/2015 | Feezor et al. |
| 2015/0305739 A1 | 10/2015 | Rolandi et al. |
| 2016/0095592 A1 | 4/2016 | Levinson et al. |
| 2017/0119371 A1 | 5/2017 | Mims et al. |
| 2017/0333039 A1 * | 11/2017 | Leung .................... A61B 17/08 |
| 2018/0008263 A1 | 1/2018 | Goldstein et al. |
| 2021/0252256 A1 | 8/2021 | Berenson et al. |

FOREIGN PATENT DOCUMENTS

| | | |
|---|---|---|
| AU | 2013273965 A1 | 12/2014 |
| AU | 2013273965 B2 | 11/2017 |
| CA | 2510389 A1 | 12/1999 |
| CA | 2330207 C | 8/2005 |
| CA | 2376128 C | 1/2009 |
| CA | 2875227 A1 | 12/2013 |
| CN | 109069155 A | 12/2018 |
| EP | 0286657 A1 | 10/1988 |
| EP | 1183065 A1 | 3/2002 |
| EP | 1281352 A1 | 2/2003 |

(56) References Cited

FOREIGN PATENT DOCUMENTS

| | | |
|---|---|---|
| EP | 1284121 A2 | 2/2003 |
| EP | 1391716 A2 | 2/2004 |
| EP | 1598011 A2 | 11/2005 |
| EP | 1360931 B1 | 1/2006 |
| EP | 1360933 B1 | 7/2006 |
| EP | 1360932 B1 | 1/2007 |
| EP | 1086214 A4 | 5/2007 |
| EP | 1973479 A2 | 10/2008 |
| EP | 2209417 A1 | 7/2010 |
| EP | 1183064 B1 | 12/2012 |
| EP | 1183066 B1 | 12/2012 |
| EP | 1834589 B1 | 12/2012 |
| EP | 1904158 B1 | 7/2013 |
| EP | 2861181 A1 | 4/2015 |
| IN | 192015 A | 5/2015 |
| JP | 2003533326 A | 11/2003 |
| JP | 2009545382 A | 12/2009 |
| JP | 2013512062 A | 4/2013 |
| JP | 2013532997 A | 8/2013 |
| WO | WO-8801955 A3 | 4/1988 |
| WO | WO-0074764 A1 | 12/2000 |
| WO | WO-0074765 A1 | 12/2000 |
| WO | WO-0074766 A1 | 12/2000 |
| WO | WO-0167944 A2 | 9/2001 |
| WO | WO-0191846 A2 | 12/2001 |
| WO | WO-02072189 A2 | 9/2002 |
| WO | WO-2005123173 A1 | 12/2005 |
| WO | WO-2006016364 A2 | 2/2006 |
| WO | WO-2006124671 A2 | 11/2006 |
| WO | WO-2007002523 A2 | 1/2007 |
| WO | WO-2007081430 A2 | 7/2007 |
| WO | WO-2008019051 A2 | 2/2008 |
| WO | WO-2008020632 A1 | 2/2008 |
| WO | WO-2008067290 A2 | 6/2008 |
| WO | WO-2009048687 A1 | 4/2009 |
| WO | WO-2010124712 A1 | 11/2010 |
| WO | WO-2010140760 A2 | 12/2010 |
| WO | WO-2011016230 A1 | 2/2011 |
| WO | WO-2011067297 A1 | 6/2011 |
| WO | WO-2011135531 A2 | 11/2011 |
| WO | WO-2012170497 A2 | 12/2012 |
| WO | WO-2013042723 A1 | 3/2013 |
| WO | WO-2013096026 A1 | 6/2013 |
| WO | WO-2013188884 A1 | 12/2013 |
| WO | WO-2017151806 A1 | 9/2017 |
| WO | WO-2023159181 A1 | 8/2023 |

OTHER PUBLICATIONS

"U.S. Appl. No. 14/408,244, Final Office Action dated Mar. 6, 2019", 21 pgs.

"U.S. Appl. No. 14/408,244, Final Office Action dated Oct. 18, 2017", 21 pgs.

"U.S. Appl. No. 14/408,244, Non Final Office Action dated Feb. 7, 2017", 14 pgs.

"U.S. Appl. No. 14/408,244, Non Final Office Action dated Jun. 4, 2018", 13 pgs.

"U.S. Appl. No. 14/408,244, Non Final Office Action dated Nov. 27, 2019", 13 pgs.

"U.S. Appl. No. 14/408,244, Notice of Allowance dated Apr. 15, 2020", 10 pgs.

"U.S. Appl. No. 14/408,244, Preliminary Amendment filed Mar. 23, 2015", 5 pgs.

"U.S. Appl. No. 14/408,244, Response filed Feb. 20, 2018 to Final Office Action dated Oct. 18, 2017", 14 pgs.

"U.S. Appl. No. 14/408,244, Response filed Jul. 24, 2017 to Non Final Office Action dated Feb. 7, 2017", 11 pgs.

"U.S. Appl. No. 14/408,244, Response filed Nov. 5, 2018 to Non Final Office Action dated Jun. 4, 2018", 9 pgs.

"U.S. Appl. No. 14/408,244, Response to Final Office Action dated Mar. 6, 2019 filed Jun. 6, 2019", 14 pgs.

"U.S. Appl. No. 15/446,999, Examiner Interview Summary dated Mar. 9, 2020", 4 pgs.

"U.S. Appl. No. 15/446,999, Examiner Interview Summary dated Sep. 29, 2020", 3 pgs.

"U.S. Appl. No. 15/446,999, Final Office Action dated Jul. 12, 2019", 15 pgs.

"U.S. Appl. No. 15/446,999, Final Office Action dated Aug. 10, 2020", 15 pgs.

"U.S. Appl. No. 15/446,999, Non Final Office Action dated Mar. 8, 2019", 14 pgs.

"U.S. Appl. No. 15/446,999, Non Final Office Action dated Apr. 7, 2020", 18 pgs.

"U.S. Appl. No. 15/446,999, Non Final Office Action dated Dec. 20, 2019", 21 pgs.

"U.S. Appl. No. 15/446,999, Notice of Allowance dated Nov. 17, 2020", 11 pgs.

"U.S. Appl. No. 15/446,999, PTO Response to Rule 312 Communication dated Feb. 17, 2021", 2 pgs.

"U.S. Appl. No. 15/446,999, Response filed Mar. 20, 2020 to Non Final Office Action dated Dec. 20, 2019", 23 pgs.

"U.S. Appl. No. 15/446,999, Response filed Jun. 10, 2019 to Non Final Office Action dated Mar. 8, 2019", 15 pgs.

"U.S. Appl. No. 15/446,999, Response filed Jul. 24, 2020 to Non Final Office Action dated Apr. 7, 2020", 21 pgs.

"U.S. Appl. No. 15/446,999, Response filed Oct. 12, 2020 to Final Office Action dated Aug. 10, 2020", 18 pgs.

"U.S. Appl. No. 15/446,999, Response filed Nov. 12, 2019 to Final Office Action dated Jul. 12, 2019", 19 pgs.

"U.S. Appl. No. 15/446,999, Response to Restriction Requirement dated Jun. 18, 2018 filed Nov. 2, 2018", 8 pgs.

"U.S. Appl. No. 15/446,999, Restriction Requirement dated Jun. 18, 2018", 9 pgs.

"U.S. Appl. No. 17/163,756 Preliminary Amendment filed Feb. 10, 2021", 5 pgs.

"Australian Application Serial No. 2013273965, Amendment filed Nov. 6, 2017", 5 pgs.

"Australian Application Serial No. 2013273965, Examination Report dated Jun. 1, 2017", 4 pgs.

"Australian Application Serial No. 2013273965, Examination Report dated Nov. 7, 2016", 3 pgs.

"Australian Application Serial No. 2013273965, Response filed Mar. 20, 2017 to Examination Report dated Nov. 7, 2016", 15 pgs.

"Australian Application Serial No. 2013273965, Response filed Nov. 2, 2017 to Examination Report dated Jun. 1, 2017", 15 pgs.

"Canadian Application Serial No. 2,875,227, Office Action dated Jun. 23, 2020", 3 pgs.

"Canadian Application Serial No. 2,875,227, Office Action dated Nov. 18, 2019", 4 pgs.

"Canadian Application Serial No. 2,875,227, Response filed Mar. 18, 2020 to Office Action dated Nov. 18, 2019", 26 pgs.

"Canadian Application Serial No. 2,875,227, Response filed Aug. 20, 2019 to Examiner's Rule 30(2) Requisition dated Feb. 21, 2019", 44 pgs.

"Chinese Application Serial No. 201780027281.1, Office Action dated Oct. 16, 2020", w/ English translation, 8 pgs.

"European Application Serial No. 13733182.3, Communication pursuant to Article 94(3) EPC dated Jul. 11, 2017", 5 pgs.

"European Application Serial No. 13733182.3, Communication pursuant to Article 94(3) EPC dated Sep. 2, 2016", 4 pgs.

"European Application Serial No. 13733182.3, Response filed Jan. 10, 2017 to Communication pursuant to Article 94(3) EPC dated Sep. 2, 2016", 17 pgs.

"European Application Serial No. 13733182.3, Response filed Jan. 22, 2018 to Communication pursuant to Article 94(3) EPC dated Jul. 11, 2017", 70 pgs.

"European Application Serial No. 13733182.3, Response filed Aug. 25, 2015 to Communication pursuant to Rules 161(2) and 162 EPC dated Feb. 26, 2015", 15 pgs.

"European Application Serial No. 17711444.4, Notification Regarding Rule 164 and Article 94(3) EPC dated Dec. 20, 2019", 10 pgs.

"European Application Serial No. 17711444.4, Response filed Apr. 9, 2019 to Communication Pursuant to Rules 161(1) and 162 EPC dated Oct. 16, 2018", 22 pgs.

(56) References Cited

OTHER PUBLICATIONS

"European Application Serial No. 17711444.4, Response filed Apr. 30, 2020 to Notification Regarding Rule 164 and Article 94(3) EPC dated Dec. 20, 2019", 57 pgs.
"European Application Serial No. 19174754.2, Extended European Search Report dated Oct. 21, 2019", 6 pgs.
"European Application Serial No. 19174754.2, Response Filed May 11, 2020 to Extended European Search Report dated Oct. 21, 2019", 8 pgs.
"Indian Application Serial No. 2939/KOLNP/2014, First Examiner Report dated Jan. 7, 2020", 5 pgs.
"International Application Serial No. PCT/US2013/046181, International Preliminary Report on Patentability dated Dec. 16, 2014", 6 pgs.
"International Application Serial No. PCT/US2013/046181, International Preliminary Report on Patentability dated Dec. 24, 2014", 7 pgs.
"International Application Serial No. PCT/US2013/046181, International Search Report dated Aug. 13, 2013", 3 pgs.
"International Application Serial No. PCT/US2013/046181, Written Opinion dated Aug. 13, 2013", 5 pgs.
"International Application Serial No. PCT/US2017/020258, International Preliminary Report on Patentability dated Sep. 13, 2018", 14 pgs.
"International Application Serial No. PCT/US2017/020258, International Search Report dated Jul. 25, 2017", 6 pgs.
"International Application Serial No. PCT/US2017/020258, Written Opinion dated Jul. 25, 2017", 12 pgs.
"International Application Serial No. PCT/US2023/062821, International Search Report dated May 4, 2023", 4 pgs.
"International Application Serial No. PCT/US2023/062821, Written Opinion dated May 4, 2023", 8 pgs.
"Japanese Application Serial No. 2015-517482, Examiners Decision of Final Refusal dated Sep. 11, 2018", w/ English translation, 7 pgs.
"Japanese Application Serial No. 2015-517482, Office Action dated Mar. 10, 2020", w/ English translation, 5 pgs.
"Japanese Application Serial No. 2015-517482, Office Action dated Mar. 14, 2017", w/ English translation, 8 pgs.
"Japanese Application Serial No. 2015-517482, Response filed Jun. 4, 2020 to Office Action dated Mar. 10, 2020", w/ English claims, 8 pgs.
"Japanese Application Serial No. 2019-002286, Notification of Reasons for Refusal dated Nov. 26, 2019", w/ English translation, 10 pgs.
"Korean Application Serial No. 10-2015-7000949, Notice of Preliminary Rejection dated Feb. 27, 2020", w/ English translation, 12 pgs.
"Mexican Application Serial No. MX/a/2014/015365, Office Action dated May 7, 2019", w/ English translation, 7 pgs.
"New Zealand Application Serial No. 702677, Search Report dated Oct. 28, 2015", 2 pgs.
"Singapore Application Serial No. 11201408221Y, Search Report and Written Opinion dated Nov. 19, 2015", 10 pgs.
"Singapore Application Serial No. 11201408221Y, Written Opinion dated May 18, 2017", 6 pgs.
"Singapore Application Serial No. 11201408221Y, Written Opinion dated Jun. 29, 2016", 4 pgs.
Francesko, et al., "Chitin, Chitosan and Derivatives for Wound Healing and Tissue Engineering", Adv Biochem Engin/Biotechnol 125, Springer, (2011), 27 pgs.
Lawton, et al., "Novel Haemostatic Dressings", JR Army Med Corps, (2009), 309-314.
Lee, et al., "ß-Chitin-based wound dressing containing silver sulfurdiazine", Journal of Materials Science: Materials in Medicine; 11(12): 817-823. (Abstract), (2000), 1 pg.
Mahdavi, et al., "A biodegradable and biocompatible gecko-inspired tissue adhesive", Proceedings of the National Academy of Sciences, (2008), 2307-2312.
Rajabi, Mina, et al., "Flexible and Stretchable Microneedle Patches with Integrated Rigid Stainless Steel Microneedles for Transdermal Biointerfacing", PloS one, 11(12), e0166330, (Dec. 9, 2016), 13 pgs.
Sugamori, et al., "Local herostatic effects of microcrystalline partially deacetylated chitin hydrochloride", J Biomed Mater Res 49(2), (2000), 225-232.
Yusof, et al., "Preparation and characterization of chitin beads as a wound dressing precursor", Journal of Biomedica Materials Research, 54(1), (2000), 59-68.
Zhong, et al., "A Chitin Nanofiber Ink for Airbrushing, Replica Molding, and Microcontact Printing of Self-assembled Macro-, Micro-, and Nanostructures", Adv Materials 23(41), (2011), 4776-4781.
Zhong, et al., "A facile bottom-up route to self-assembled biogenic chitin nanofibers", Soft Matter 6(21), (2010), 5298-5301.

\* cited by examiner

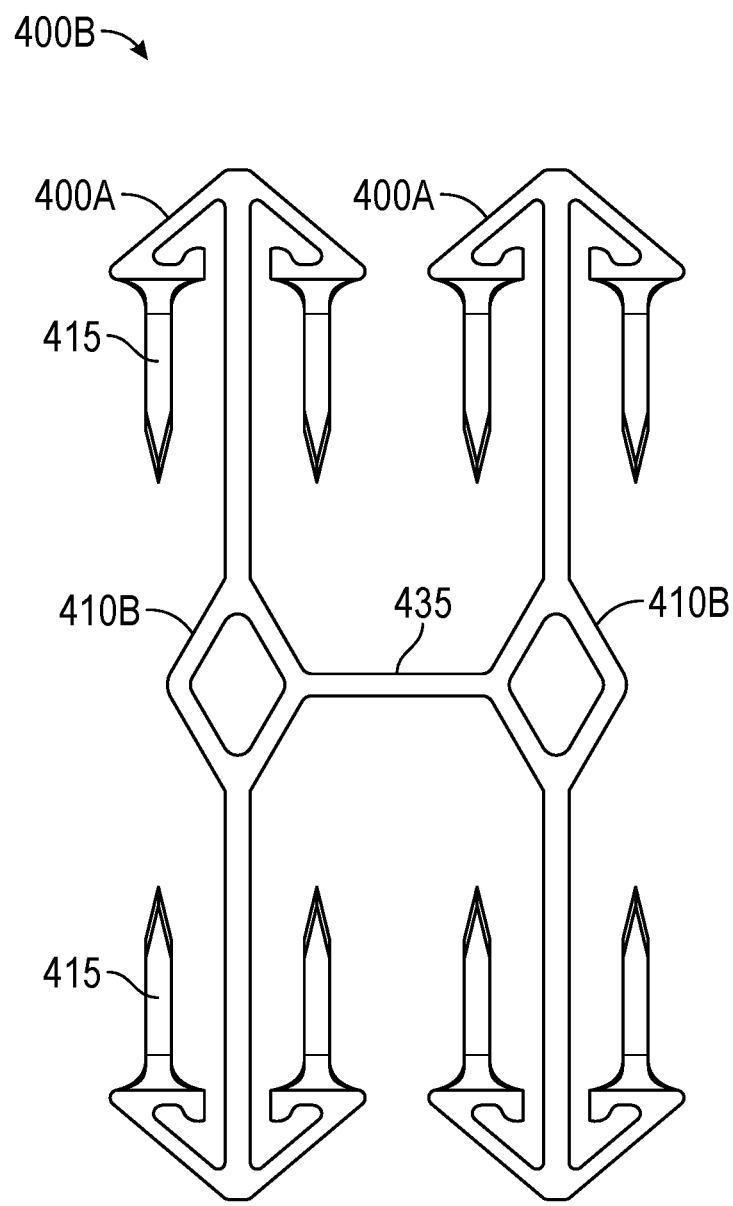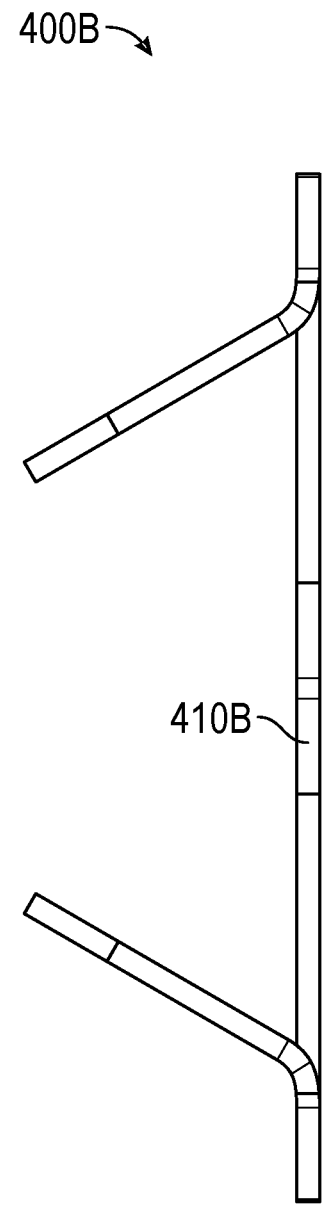
FIG. 4D
FIG. 4E

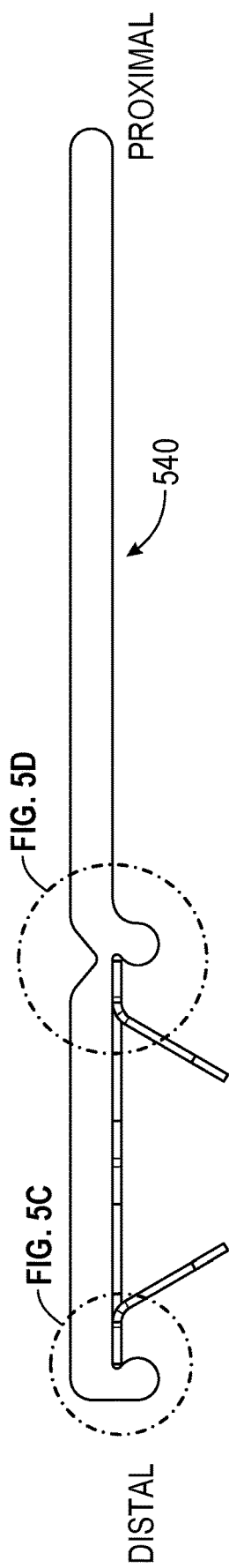
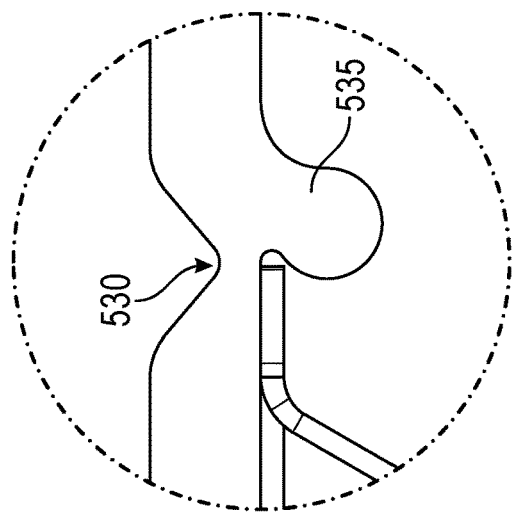
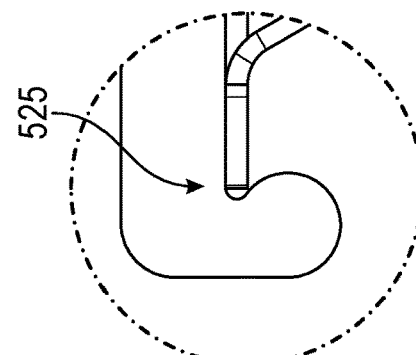
FIG. 5B
FIG. 5C
FIG. 5D

FORCE MODULATING DEEP SKIN STAPLES AND INSTRUMENTS

CROSS REFERENCE TO RELATED APPLICATIONS

This patent application claims the benefit of priority to U.S. Application Ser. No. 63/268,218, filed Feb. 18, 2022, which is incorporated by reference herein in its entirety.

This application includes concepts related to U.S. patent application Ser. No. 14/408,244, filed on Mar. 23, 2015, and now issued as U.S. Pat. No. 10,751,050, and U.S. patent application Ser. No. 15/163,756, filed on Mar. 1, 2017, and now issued as U.S. Pat. No. 10,939,912, each of which is herein incorporated by reference in its entirety.

BACKGROUND

Multiple techniques can be utilized for closing wounds. The techniques can use sutures, staples, and tissue adhesives. Wound closure procedures have primarily utilized sutures and staples for many years. Staples are becoming more frequently used because they are easier and much faster to apply than sutures. Tissue adhesives are relative newcomers to the wound closure world. These products can be difficult to use. In addition, scarring often occurs with all of these wound closure products. Efficient and effective closure that will result in wound healing with minimal scarring is the objective of the closure procedure. Unfortunately, sutures, staples, and tissue adhesives cannot always provide these benefits.

SUMMARY

Embodiments described herein relate generally to systems, apparatus, and methods for reducing scarring during healing of skin wounds including incisions, lacerations, skin tears, and port sites; in particular to using a force modulating deep skin staple ("deep skin staple") designed to prevent or reduce scarring through mechanical force and tension reduction in certain skin layers in the dermis. For the purposes of this disclosure, "deep skin" is defined as describing tissues that include tissue layers down into the papillary dermis and the reticular dermis layers of skin. Another embodiment provides an applicator to apply the deep skin staple. Another embodiment includes an element to measure mechanical force generated by the deep skin staple across the wound so that optimal and uniform tension can be produced to reduce scarring. Another embodiment measures the force generated to apply the deep skin staple to the skin so that optimal insertion of the staple legs and attachment of the deep skin staple occurs. In certain embodiments, the deep skin staples include legs that have maximal surface area in the dermis, and in particular the reticular dermis, after the deep skin staples are inserted into the skin to reduce mechanical force and relieve tension to reduce scarring. Certain embodiments have the widest surface area where the legs are in contact with the reticular dermal layer to provide maximal effects on force and tension. Certain embodiments also have legs that have minimal surface area at the surface of the skin after the deep skin staples are inserted into the skin to reduce the size of insertion holes that can cause scarring and infection. In addition, an embodiment described herein relates generally to systems, apparatus, and methods for safely closing both the upper skin (epidermis and upper dermis) and the deeper dermal layer(s) (e.g., deep skin) in one procedure.

The embodiment of the deep skin staple discussed above can be applied to close a wound using an applicator. In an embodiment described herein is the applicator allows deep skin staples to be inserted into the skin. In certain embodiments, the applicator can include an element to measure the lateral force applied across the wound while applying the deep skin staple to ensure optimal force is applied during wound closure.

Scarring

One of the major issues with wound closure products, such as sutures and conventional surgical skin staples, is that they often cause scarring. The invention described herein is intended to decrease scarring and improve cosmetic outcomes.

Scars arise after injury to the skin. Scars can be disfiguring and aesthetically unpleasant and may cause severe itching, tenderness, pain, sleep disturbance, anxiety, depression, and disruption of daily activities. Other psychosocial sequelae include development of post-traumatic stress reactions, loss of self-esteem, and stigmatization, leading to diminished quality of life. Physical deformity as a result of skin scar contractures can be disabling. Scarring represents a major clinical burden in the United States. There are more than 175,000 scar revision surgeries performed each year. Scars are also responsible for a considerable amount of healthcare resources related to the care of patients with scarring.

Scarring is a pathophysiological process whereby a structural change occurs in the deeper layers of the skin which is perceived as an alteration in the architecture of normal surface features. Scars differ from normal skin aesthetically, functionally, and morphologically. The scar is comprised of poorly structured and densely packed collagen fibers and the hair and glands present in normal skin are missing. Damage to the deeper layer of the skin, the dermis, is required to produce a scar.

Scarring is created by proliferation of fibroblasts which are located in the dermis. They produce collagen which creates a dense matrix that provides the wound strength that is part of the normal healing process. However, this also results in scarring when excess levels of collagen are produced. Fifty percent (50%) of the protein in scar tissue is collagen which forms the dense fibrous tissue characteristic of a scar.

There is a spectrum of scar formation, with scarless regeneration on one end, "normal" scar formation in the center, and pathological scar formation on the other end, including hypertrophic and keloid scarring. Keloid and hypertrophic scarring contribute to much of the morbidity of scarring. Hypertrophic scars can be defined as scars forming after injury that are larger or more raised than usual, or that results in contracture. Keloid scars, on the contrary, represent an abnormally exuberant scarring response that extends beyond the borders of the original injury. Keloids cause symptoms of pruritus and hyperesthesia and tend to recur after excision, as opposed to hypertrophic scars that may not recur if the scar is revised appropriately.

Treatments for scarring include chemical peels, filler injections, laser treatment, dressings, chemical peels, surgical revision, radiation, cryotherapy, pressure and massage, vacuum therapy, and drugs such as corticosteroids and botulinum toxin. All of these treatments are of variable effectiveness and rarely eliminate the scar altogether.

The best way to eliminate scarring is by prevention. Current methods primarily consist of applying sheets to the skin which are made of silicone, polyurethane, or paper tape, and are thought to act by providing a moist wound environment to reduce scar formation. Alternatively, gels or other solutions containing silicone are used to reduce scarring. However, these approaches are only modestly effective and are not able to be used in the early stages of scar formation (first two weeks) when the scar formation process begins. They also require daily therapy over several months which most patients are unwilling to do.

There is thus a strong unmet need for new approaches to prevent and treat scarring.

Mechanotransduction

The skin is comprised of three layers—epidermis, dermis, and subcutaneous layers. The epidermis is the most superficial layer and is about 100-200 microns in depth. It primarily serves as a barrier that prevents entry of bacteria into the body and protects the body from environmental stress and toxic substances. It does not contain collagen or other components that provide tensile strength.

The dermis provides the tensile strength of the skin. It comprises two structurally different layers named the papillary and reticular layers. The papillary layer, which is located closer to the skin surface, reaches a depth of 300-600 microns. The reticular layer of the dermis is beneath the papillary layer and extends 3 mm or more below the skin surface. The cells of the reticular layer produce the vast majority of collagen while the papillary layer produces primarily proteoglycans. Therefore, it is the reticular layer that contains most of the collagen which provides the majority of the tensile strength of the dermis. The bottom layer of the skin is the subcutaneous layer which consists primarily of adipose tissue and has little in the way of components (e.g., collagen) that contribute to tissue strength. They thus contribute minimal holding power for staples and sutures. The subcutaneous tissue is thus unable to exert additional force and tension when staples and sutures enter this layer. Consequently, the dermis provides nearly all of the holding power, mechanical force and tension in the skin and that is required to close wounds.

Fibroblasts are the most abundant cells in the dermis. The ability to synthesize collagen is the main and unifying feature of fibroblasts. Fibroblasts also transform into myofibroblasts, especially during the wound healing process, which produce collagen. The vast majority of fibroblasts and collagen production occurs in the deeper reticular dermal layer. This transformation occurs in part as a result of mechanical forces and tension on the dermis.

During the process of normal wound healing, contraction of the wound occurs which leads to the synthesis of collagen by fibroblasts. This increases wound strength and is important for normal wound healing.

Although the production of collagen plays a critical role in achieving wound strength which is critical for healthy wound healing, collagen is also the major contributor to scarring. It is the excess production of collagen by the dermal reticular layer fibroblasts and myofibroblasts that plays the major role in the scarring process.

Recent studies have demonstrated that fibroblasts are activated to produce excess collagen in the presence of mechanical forces referred to as mechanotransduction. This process results in scarring. Most of the fibroblasts are located in the reticular layer of the dermis. Therefore, therapeutic approaches to reduce or modulate mechanical forces (also referred to as force modulation) or their sequelae that lead to the production of collagen by fibroblasts in the reticular layer should be effective in reducing scarring.

One therapeutic approach is to target one of the many biochemical and genetic pathways of reticular dermal fibroblasts that are affected by mechanotransduction and mechanical loading and contribute to scarring. The first attempt at molecular targeting was using a monoclonal antibody to block the effects of Transforming Growth Factor-$\beta$, which is activated by mechanical force and is a major player in the fibrotic process. This agent failed in clinical studies. Another target that has been evaluated is FAK, where a drug was used to inhibit this enzyme, which is involved in one of the pathways leading to scarring. More recently, a drug that inhibits YAP, another molecule active in the scarring process, has been shown to be effective in animal models of scarring. Clinical studies are planned to test this drug in humans. However, it is unlikely that targeting only one or a few of the dozens of biochemical and genetic pathways affected by mechanotransduction will be effective in ameliorating mechanotransduction-related fibrosis and scarring.

Force Modulating Deep Skin Staples

A strategy that can act upstream to target mechanical forces which activate the many biochemical and genetic pathways that lead to scarring is likely to be more effective. This can be accomplished by a deep skin staple that is able to modulate the mechanical forces and achieve mechanical off-loading and tension relief at the level of the reticular dermis where the majority of the fibroblasts that produce collagen are located.

Consequently, this approach will affect all or most of the pathways downstream of mechanotransduction and thus be more effective than using molecular agents that target one or only a few these pathways. To be most effective, the deep skin staple needs to modulate mechanical forces at the level of the dermis and especially the reticular layer of the dermis, where the majority of fibroblasts and myofibroblasts reside that produce collagen that leads to scarring.

Sutures and conventional surgical staples (e.g., surgical box staples) are the most common products used to close wounds and are able to enter the reticular layer of the dermis and thus are potential candidates for reducing scarring. However, they are inelastic and primarily rigid structures (note: there are some internal staples that have elasticity, but they are for closing internal organs and tissues and not the skin). Consequently, they are unable to decrease mechanical forces and relieve tension and prevent or reduce skin scarring. Tissue adhesives (e.g., Dermabond®, a product of Ethicon US, LLC a division of Johnson & Johnson Surgical Technologies) are sometimes used to close wounds. They consist of polymers such as cyanoacrylates. These polymers are inelastic and thus unable to relieve tension and reduce mechanical forces required to prevent or reduce scarring.

Suture closure requires a procedure to close the upper skin layer (epidermis and papillary layer) and a second procedure to close the deeper skin layer (reticular dermis). Thus, using a suture to close the upper skin layer does not reach the reticular dermis. They are also rigid and inelastic structures and thus cannot modulate force and relieve tension. Consequently, they are unable to be used for force modulation to reduce scarring.

Conventional surgical staples are the other commonly used wound closure product. There are two categories of surgical staples—skin staples and internal staples. Skin staples are used to close the skin, while internal staples are used to close internal tissues and organs. Although there are many designs, shapes, and sizes of internal staples, most if not all skin staples are relatively similar.

Conventional skin staples are usually made out of metal with stainless steel being most common, but sometimes titanium is used (although this is primarily in internal staples). There are some conventional staples that are made out of rigid polymers, such as the INSORB stapler (Cooper Medical, Trumbull, CT), but it is actually deployed underneath the skin, so it is not a true skin staple product. Conventional skin staples are rigid and inflexible and thus unable to modulate mechanical force and relieve tension to reduce scarring.

Conventional skin staples usually come in two sizes, wide staples which are used 80% of the time and regular staples that are used 20% of the time. The sides of the legs of skin staples are typically cylindrical in shape. They usually have uniform diameter throughout the staple legs which range from 0.55 to 0.58 mm and 0.51 to 0.53 mm for wide and regular staples, respectively. The conventional staples have widths that range from 6.4 to 7.1.mm and 5.0 to 5.7 mm for wide and regular staples, respectively. The conventional staple depths range from 3.5 mm to 4.7 mm and 3.5 to 3.9 mm for wide and regular staples, respectively. The conventional staples with these dimensions have been demonstrated to have adequate strength to close wounds. The regular staples are used to close wounds in areas of the body that require less tension such as on the face, while the wide staples are used in most of the other regions of the body.

Conventional skin staples have a length (3.5 mm to 4.7 mm) that allow them to reach through the reticular dermis (~3 mm depth) and thus have the potential to affect mechanical force and tension at the level of skin required to significantly reduce scarring. However, staples are rigid and inelastic structures. Given their lack of elasticity, they do not have the capacity to modulate mechanical force and thus relieve tension along the wound. Therefore, they cannot achieve force modulation to prevent or reduce scarring.

Conventional skin staples also have other challenges in closing wounds. They have relatively large diameters (~0.5-0.6 mm) in order to provide the tensile strength required to close both the upper and lower skin layers. This results in relatively large holes on the skin surface upon the insertion of staples. These holes serve as portals of entry for keratinocytes which lead to "railroad track" scarring and other kinds of scarring that are often observed with staples. In addition, the large holes serve as entry points for bacteria to enter the skin and eventually the wound which may lead to infection. Staples also have other problems and challenges. They can cause significant tissue damage that may cause scarring and lead to infection. In addition, stapling typically requires two operators—one to bring the wound edges together and the other to operate the stapler. The location of staples is variable due to the inconsistent placement of the individual staples by the operators.

Conventional skin staples have a similar design to staples for other uses (e.g., attaching pieces of paper together). They have a boxlike configuration after placement in the skin with the staple legs shaped at a 90-degree angle underneath the skin at the bottom of the staple such that the end of the staple is parallel the skin. A special staple removal device is required to remove these staples from the skin which first straightens out the staple so that it can be pulled out of the skin. This can be difficult to achieve and is often painful. Finally conventional staples require two operators—one to line up the two edges of the wound and the other to use the stapler to close the wound.

New approaches to reduce mechanical forces and tension to prevent or decrease scarring are needed. There are currently several alternative devices that have been developed and marketed designed for this purpose, including TopClosure®, IVT Medical, Ra'anana, Israel; Zipline, Zipline Medical, Inc., Campbell, CA, and Brijjit, Brijjit Medical, Atlanta, GA.

However, the devices described above are only attached to the skin. They do not penetrate the skin and are thus unable to modulate the major cause of scarring during the wound healing process—increased mechanical forces and tension below the skin surface at the level of the dermis. Consequently, these alternative devices are inadequate to target the layer of the skin where force modulation is needed to prevent and reduce scarring.

microMend® Wound Closure Product microMend® (KitoTech Medical, Seattle, WA) incorporates two arrays of miniature staples referred to as Microstaples with a proprietary adhesive backing. Upon the application of microMend®, the Microstaples penetrate the skin. The Microstaples are incorporated into an array that contains cantilever springs. The springs provide elasticity to eliminate the skin irritation that was observed with the original microMend® device that was inelastic and inflexible. The skin irritation and resulting inflammation were caused by the rubbing of the inelastic device against the skin during movement. The incorporation of springs into the device solved this problem.

It is now recognized that the springs provide microMend® with the potential to modulate mechanical forces and reduce tension and thus minimize scarring. However, microMend's Microstaples have a length of 1 mm in vertical height that only allows them to penetrate the upper layers of the skin. This design was to meet the objective of closing the top skin layer. The Microstaples reach little if any of the reticular layer of the dermis. Given that force modulation needs to occur in this dermal layer, microMend is inadequate for significantly reducing scarring via force modulation in deeper layers of the skin. In addition, Microstaples are relatively thin structures—approximately 200 microns in width, since they extend only into the upper skin which has relatively minimal tensile strength and is less thick and dense than the deeper dermis. It thus requires much less force to close a wound. Although Microstaples are wide enough to close the top skin layer, their thin structure makes them suboptimal for closing the thicker and denser dermis. They are thus unable to close a deeper wound in a manner that achieves force modulation at the level of the thicker and denser dermis.

The present invention describes a deep skin staple that contains longer staples than the Microstaples in microMend® extending into and through the reticular dermis. The wider width of the deep skin staple also provides more surface area than Microstaples which is required to close wounds and achieve force modulation in the dermis. In addition to these longer staples, the deep skin staple also contains spring characteristics that are able to modulate mechanical force and offload tension at the reticular layer of the skin. The deep skin staple thus combines force modulation via springs and staple leg design to relieve wound tension with the depth of penetration into the reticular layer to reduce fibroblast production of collagen.

The deeper skin layer, the reticular dermis is made of thick dense tissue, primarily consisting of collagen. It requires considerably more force to close wounds extending into the reticular dermis compared to wounds in the upper skin layers (epidermis and papillary dermal layer). In addition, the reticular layer is typically 3-4 mm in thickness which is much thicker than the upper skin layers (epidermis and papillary dermal layer—600 to 800 microns). Consequently, a much larger volume of tissue must be brought together to close the reticular skin layer. The combination of dense tissue and more tissue requires a deep skin staple with more surface area below the skin than microMend® to close a wound that extends from the superficial skin through the reticular layer. Accordingly, one approach utilized by some of the disclosed deep skin staples is a large surface area with a design such as a shovel or paddle shape on the legs of the deep skin staple. The larger surface area of the shovel or paddle faces the wound in order to maximize forces across the wound. Importantly, the features of the legs of the deep skin staples described herein also provide the level of mechanical force required to relieve tension and prevent or reduce scarring.

Deep skin staples need to have the strength to close the wound and provide sufficient mechanical force to off load tension to reduce scarring. At the same time, the deep skin staples need to reduce opportunities for entry of bacteria that lead to infection of the wound and surface scarring due to the large holes at the skin surface created by conventional staples. Therefore, the deep skin staples need to have decreased cross-sectional area of the legs at the skin surface to reduce the size of these holes. Consequently, in certain examples a deep skin staple with legs that have more surface area at the reticular layer of the dermis and less surface area (or cross-sectional area) at the base of the leg of the staple where it is at the skin surface can be provided. In other examples, deep skin staple legs with a cross-sectional area that is roughly consistent throughout their length are used. Deep skin staples with legs having a consistent cross-sectional area can also be effective in modulating forces at the reticular layer and may have small cross-sectional area at the skin surface.

A deep skin staple with these features is described herein. The legs of the deep skin staple entering the wound are designed to minimize the surface and cross-sectional area that is present at the skin surface, while maximizing the surface area that is present in the reticular layer of the dermis after the deep skin staple is inserted into the skin. The surface area of the staple is maximized where the legs of the staple face the wound which is where the force is needed to close the wound and achieve force modulation. A larger surface area is able to generate more force and tension over a greater volume of the reticular layer which translates into better wound closure and the ability to off load more tension at the wound site which reduces scarring. At the same time, the portion of the staple leg is thin and has a small surface and cross-sectional area on the skin surface which reduces the size of insertion holes after application of the deep skin staples. This reduces risk of bacteria and keratinocytes entering the wound and causing infection and scarring, respectively. Additionally, the shovel or paddle portion of the leg terminates in a sharp tip to provide ease of penetration into the skin with modest force.

In examples of the deep skin staple, the staple leg may be shaped similar to an arrowhead, shovel, paddle, house, or triangle to achieve the features described above in order to allow the wound closure device to close the wound and achieve force modulation while reducing risks of scarring and infection that occur with other wound closure products such as sutures and staples.

During application of other wound closure devices, the tension generated across the device is not known or measured and so the force generated may not be optimal to create force modulation to reduce scarring as well as close the wound. In addition, the force may vary creating uneven tension along the wound and thus inconsistent results with some areas of the wound having too little tension created between wound edges leading to wound gaps that can lead to bacterial entry and scarring. Alternatively, creating too much tension can lead to inflammation and scarring.

Incorporating an element into the deep skin staple that measures tension during wound closure would ensure that optimal mechanical force is being applied across the wound to prevent or reduce scarring and eliminate wound gaps that lead to infection and scarring. This will also enable more uniform tension across the wound which will lead to more consistent results. Finally, it will ensure better wound closure by allowing more optimal force to be used to close a wound.

To achieve this, the deep skin staple may contain two parallel lines along its length that are slightly separated from one another. When optimal tension is generated, the lines overlap, and the wound is closed with optimal forces generated to off load tension and reduce scarring and close the wound. As an alternative, the deep skin staple can incorporate an applicator tab using a material that tears when optimal tension is created. The material could be paper or some other easily tearable material. The material such as paper could incorporate perforations which would separate when optimal tension is created.

To control the application of tension on the wound during closure, an applicator can be designed that provides the force necessary for the deep skin staples to penetrate into the skin, and optimally to the maximum depth possible without causing tissue damage. The applicator can be designed to allow the skin staples to reach into the reticular layer of the dermis. The applicator can be used with deep skin staples or with conventional staples.

An applicator similar to current staplers could be used to attach the staples and their array of legs to the skin. Alternatively, other applicators such as a punch or roller could be used to affix the deep skin staple to the skin. The applicator can be disposable or reusable. The deep skin staple can also be applied manually without an applicator. An example applicator is discussed below in reference to FIGS. 5A-6. The example applicator is designed specifically for application of the discussed deep skin staples and involves a unique application technique. However, a similar applicator could be designed for use with conventional staples. One of the benefits provided by the applicator is the ability to evenly space staples, among other things.

Force is best placed over the deep skin staple in order to ensure that the legs enter the skin and reach the reticular dermal layer. To do so, a mark such as a circle, disk, square, of other figure can be placed on the backing at the locations of each deep skin staple to ensure that force is placed directly over the staple legs. The marks can also be placed on the staple array. Alternatively, the mark can be placed over the staple leg to provide force more precisely over it to ensure that it enters the skin and reaches the dermal layer and in particular the reticular layer. It is also possible to provide marks over the entire staple as well as the legs themselves.

Use of an applicator such as a specialized applicator is envisioned as one method to ensure that the staples penetrate the dermal layer of the dermis, and preferably the reticular dermal layer, to prevent or decrease scarring. This could be either incorporated into the deep skin staple or consist of a separate element that provides the force. The applicator can be disposable or reusable. The example applicator discussed below is disposable.

The amount of force that is used to attach the deep skin staple may vary between and among operators, whether applied manually or using an applicator. To address this issue, the applicator can be designed to provide uniform force for the staples to enter the skin which will reduce the variability that may occur when staples are manually attached to the skin.

Alternatively, an element could be provided that measures the force exerted by pressure on the skin during application of the deep skin staple. These elements can be located at several points along the deep skin staple, such as at the location of each staple leg (or array of legs) or at a few points or one point in the deep skin staple. The elements can also be located on the staples themselves, the staple array, or the backing. The measure could be a pressure sensitive element that releases a visual signal such as a color change or release of a fluid when adequate pressure is placed to insert the deep skin staple into the skin. The element can also be incorporated into an applicator.

The deep skin staples described herein can be used alone or be attached to a backing. A backing helps ensure uniform placement of the staples and arrays along the wound and thus reduces inconsistent results that occur due to variations in operator application of staples. The backing may be permanent or temporary.

A permanent backing can help ensure that the staples remain inserted in the skin. A permanent backing can help provide uniform force along the wound, but also provide a barrier to reduce the risk of infection. A permanent backing can also help provide uniform tension along the wound which reduces scarring. In addition, it can help create a moist environment over several days to weeks while the staples remain on the skin. A moist environment during the process of wound healing can prevent or reduce scarring as demonstrated with silicone, polyurethane, and paper tapes and bandages. A permanent backing could contain other materials or agents to eliminate bacteria, promote wound healing, reduce inflammation, and stop bleeding.

A temporary backing could be removed during or before application. In an example, the backing is removed after application of the deep skin staple to the skin. The temporary backing is only designed to ensure that optimal and uniform tension is achieved along the wound and ensure that deep skin staples are present at uniform distances from one another along the length of the wound (in examples that utilize an array of deep skin staples). With a removable backing, therapeutic agents such as wound dressings, antibacterial agents, wound healing agents, anti-inflammatory agents, hemostatic agents, anti-scarring agents and others can be applied directly on the wound. A removable backing also makes it possible to apply a final cover, dressing or other material after the closure procedure is completed at a time when there is potentially reduced wound drainage and bleeding. This will decrease the risk of the cover detaching from the skin surface which can occur when it is applied on wet surfaces.

Finally, a wound cover could be placed on the skin prior to application of the deep skin staples. In this scenario, the staples would help ensure that the wound cover remained on the skin.

The inventors have recognized and appreciated that systems, apparatus, and methods related to wound closure devices comprising one or more staple-like structures (e.g., deep skin staples) that reach the reticular layer of the dermis would be required for preventing or reducing scarring. In addition, they recognized that force modulation is one key to scar mitigation and thus developed a force modulating deep skin staple, referred herein more generally as a deep skin staple or simply as a staple. The force modulating deep skin staple ("deep skin staple") can achieve wound force modulation at the deep skin level required to prevent or reduce scarring.

In some embodiments, the deep skin staple includes one or more staple-like structures that each include a bridge portion, leg portions, and tip portions. In some embodiments, the deep skin staples each include a central spring structure coupling each of the legs to the central structure (e.g., bridge). Each of the legs include a shovel or paddle portion that terminates in a tip structure. One of the key features of the deep skin staple to enable force modulation is the individual spring arms connecting each staple leg to the central bridge portion of the deep skin staple.

In some examples, the deep skin staples are formed in a shape to create optimal force modulation and reduction of tension. In one such embodiment, the legs of the staple are angled to point toward the center of the wound to promote wound closure and eversion of the wound. In some examples, the staples are formed in a shape to prevent their premature detachment from the skin. In one such embodiment, the legs of the staple are pointed in a direction that is parallel to the length of the wound. In one embodiment, the deep skin staples are formed in a shape to both create force modulation and prevent their premature detachment from the skin. In one such embodiment, the legs of the staple are both pointed toward the center of the wound and parallel the length of the wound.

In some examples, the deep skin staples can be arranged in an array on a common backing. The array of deep skin staples can be cut to any size to match the length of the wound or desired treatment length. The array of deep skin staples on a common backing can be interconnected via connection members or held in relative position only by the backing. The array of deep skin staples can include a plurality of deep skin staples on a backing or applicator to form a repeating pattern of individual staples at regular or irregular intervals. Regular intervals ensure uniform tension along the wound thus reducing scarring that occurs at points of high tension that occur at insertion points that vary along the wound with inconsistent placement and tension that occurs with using sutures and staples.

More deep skin staples in the array may achieve increased mechanical force with potentially better off loading of tension further reducing scarring. More deep skin staples may also allow thinner staples to be used to generate equivalent force to that generated by fewer staples in the array. Thinner staples (staple legs) at more frequent intervals along the wound will create more uniform tension resulting in less scarring. The thinner staples will also create smaller holes on the skin surface and thus reduce the risks of entry of keratinocytes and bacteria that can result in scarring and infection, respectively. Thinner staples may also cause less trauma which leads to inflammation and scarring. The deep skin staples may also be attached to a removable or detachable backing. The backing can be removed, and a wound cover applied at a more optimal time after wound closure when there is reduced bleeding or drainage that could negatively affect the ability of a backing to attach to the skin. Alternatively, the backing can be non-detachable which can provide more uniform tension along the wound, more consistent placement of the staples, protect the wound from infection, and create a moister environment to prevent or reduce scarring.

In some embodiments, an application instrument (applicator) is provided with the deep skin staples to facilitate wound closure using the deep skin staples. The applicator can be configured to apply a single deep skin staple or an array of deep skin staples. In an example, the applicator includes an elongate handle extending proximally from a deep skin staple retention section. The deep skin staple retention section can include a pair of opposing retention wedges that hold the deep skin staple in the applicator during application. The applicator can also include a release notch that allows for release of the deep skin staple after application. In certain examples, the applicator can include a force measurement feature as well as a wound visualization feature. The force measurement feature assists the operator in applying the optimal application force during wound closure while the wound visualization feature assists in properly positioning of the deep skin staple relative to the wound during application.

The deep skin staples can be removed with an instrument, such as a conventional skin staple remover, a staple extractor, forceps, tweezers, or other instruments that are able to firmly attach the staples to enable their removal while pulling the staples out of the skin. The instrument can be disposable or reusable.

Deep Skin Staple:

The following examples focus on the design, capability, and structure of the force modulating deep skin staple, which are also referenced herein as staples or deep skin staples more generally. In this context, a deep skin staple can refer to an individual staple, an individual array of staples, more than one array of staples, staples with a backing, an array of staples with a backing, an individual array of interconnected staples, or more than one array of interconnected staples. Further each deep skin staple can include multiple staple legs in multiple opposing arrays coupled by a bridge portion with or without a spring structure. The following also includes examples related to arrays of deep skin staples. Multiple arrays of staples can be interconnected by a backing. The deep skin staples (referenced in these examples as a "staple") disclosed herein can include the following characteristics and capabilities (outlined below as numbered examples that are applicable to all examples discussed in reference to FIGS. 1A-4I and 8A-11E):

1. The staple may be formed to close skin.
2. The staple may be formed to close a skin wound.
3. The staple may be used to close the skin comprising the epidermis and dermis.
4. The staple may be used to close the skin comprising the epidermis, papillary dermis, and reticular dermis.
5. The staple may be used to close an acute skin wound.
6. The staple may be formed so they can close wounds that include lacerations, skin tears, surgical incisions, insertion sites associated with catheters, tubing, and surgical drains, port sites associated with minimally invasive surgeries (laparoscopic and robotic), and others.
7. The staple may be used to close a chronic skin wound.
8. The staple may be used to close a pressure ulcer, venous ulcer, arterial ulcer, or diabetic ulcer.
9. The staple may reach through a portion of or the entire reticular layer of the skin.
10. The widest portion of the staple (e.g., shovel portion) may extend through the reticular dermis.
11. The tip of the staple may extend into the subcutaneous tissue.
12. The staple may be designed in a variety of shapes, including pyramids, triangles, cones, arrowheads, paddles, shovels, houses, and rectangles.
13. The staple may contain a tip that is a blade.
14. The staple may be designed with a sharp tip that facilitates penetration through the skin.
15. The staple may be designed so that they can be inserted manually or using an applicator.
16. The staple may be designed so that they can be inserted manually or using a specialized applicator.
17. The staple may be designed to facilitate painless penetration through the skin.
18. The staple may be absorbable.
19. The staple may be non-absorbable.
20. The staple may be made out of metal.
21. The staple may be made out of metal that can include stainless steel, titanium, tungsten, nitinol, or other suitable metallic materials.
22. The staple may be made out of other polymers that can include polymethyl methacrylate (PMMA), polycarbonate, silicone, chitin, chitosan, eco-flex, glass, silk, catgut, chromic catgut, polyglycolic acid, polydioxanone, polytrimethulene, carbonate, nylon, polypropylene, polyester, elastin, resilin, collagen, cellulose, and any combination thereof
23. The staple may be made of natural material, or a mixture of natural materials; while in other embodiments it is a synthetic material, or a mixture of synthetic materials. In some embodiments, the staples are comprised of nontoxic, biodegradable, bioresorbable, or biocompatible materials, or combinations thereof
24. The staple may incorporate structures such as microbarbs, microneedles, microblades, microanchors, microhooks, microfishscale, micropillars, microhairs, and combinations thereof.
25. The staple may contain barbs.
26. The staple may include a central structure incorporated into the deep skin staple that contain one or more springs that are able to relieve tension.
27. The staple may be formed so that it can provide secure attachment to the skin or through a depth of skin associated with a wound.
28. The staple may be formed so that it can provide relief of tension to the skin or through a depth of skin to prevent or reduce scarring of a wound.
29. The staple may be formed so that it can provide force modulation, reduce mechanical force, or relieve tension on the wound by reaching a depth of skin to prevent or reduce scarring of a wound.
30. The staple may be formed so that it can decrease mechanical forces on the wound by reaching a depth of skin to prevent or reduce scarring of a wound.
31. The staple may be formed so that it can reach a depth of skin to prevent or reduce scarring.
32. The staple may be able to reach the depth of skin required to achieve force modulation and prevent or reduce scarring.
33. The staple may be formed so that they provide the tensile strength required to close wounds.
34. The staple can be removed with an instrument, such as a conventional skin staple remover, a staple extractor, forceps, tweezers, or other instruments that are able to firmly attach the staples to enable their removal while pulling the staples out of the skin.
35. The instrument in example 31 can be disposable or reusable.
36. The staple legs surface facing the wound may be of a shape and surface area that is needed to provide the tensile strength required to close a wound.
37. The sides around the leg of the staple may be in the form of a circle.
38. The sides around the leg of the staple may be in the form of a square.

39. The sides around the leg of the staple may be in the form of a rectangle.
40. The sides around the leg of the staple may be in the form of an oval.
41. The sides around the leg of the staple may be in more than one form.
42. The staple legs may be of a thickness or width (e.g., have a surface area presented to the wound-transverse to a longitudinal axis running through a bridge portion) that is able to bring the dermal portion of the wound edges together.
43. The staple legs may be formed so that their thickness/width reduces mechanical force.
44. The staple legs may be formed so that their thickness/width enables force modulation.
45. The staple legs may be formed so that their thickness/width allows relief of wound tension.
46. The staple legs may be of a thickness from 0.1 to 4 mm, preferably 0.1 to 1 mm, and most preferably 0.1 to 0.5 mm.
47. The sides of the legs of the staple may have a curved surface.
48. The sides of the legs of the staple entering the wound may be a flat surface.
49. The sides of the legs of the staple may be a combination of flat and curved surfaces.
50. The sides of the legs of the staples entering the wound may all be of equivalent width.
51. The width of the sides of the legs of the staple may vary along its length.
52. The sides of the legs of the staple entering the wound may be of different widths.
53. The side of the leg of the staple facing the wound may be wider than the side perpendicular to the wound.
54. The shape of the legs may vary along its length.
55. The legs of the staple in example 54 may be curved.
56. The legs of the staple in example 54 may be straight.
57. The legs of the staple in example 54 may be curved and straight.
58. The angles of the legs may vary along its length to reduce mechanical force and achieve force modulation.
59. The legs of the staple may be at less than 90-degree angle with respect to the portion of the staple that is on the skin surface.
60. The surface of the legs of the staple facing the wound may be at an angle of 10-90 degrees, preferably 30-60 degrees, and more preferably at 60-degree angle with respect to the portion of the staple that extends along the surface of the skin (e.g., relative to the bridge portion).
61. The bottom portion of the legs of the staple are not at a 90-degree angle.
62. The angles of the legs may vary along its length to increase attachment to the deep skin.
63. The angles of the legs of the staple may vary along its length to prevent its detachment from the skin.
64. The surface of the legs of the staple in example 63 facing parallel to the wound length may be at an angle of 10-90 degrees, preferably 30-60 degrees, and more preferably 60-degrees relative to the bridge portion.
65. The staple in example 64 may also contain legs that may be facing in a direction that is along the wound length.
66. The legs may have different angles between portions of them along their length.
67. The staple is thinner than a conventional skin staple.
68. The staple is wider than a conventional skin staple.
69. The thickness or width of the legs may vary along the length of the staple.
70. The mid-portion of the staple may be the widest portion in the staple.
71. The widest portion of the staple leg may be 0.1 mm to 2 mm, preferably 0.3 to 1 mm, and more preferably 0.4 to 0.6 mm.
72. The widest portion of the deep skin staple may be in the staple legs where they are in the reticular dermis after application of the deep skin staple.
73. The maximal surface area of the staple legs facing the wound may be in the reticular dermis after application of the deep skin staple.
74. The thinnest portion above the wide portion of the staple legs may be at the level of the epidermis after application of the deep skin staple.
75. The narrowest portion of the staple may be in the legs where they are at the level of the epidermis after application of the deep skin staple.
76. The narrowest portion of the staple leg may extend from the superior surface of the staple to 50 microns to 1 mm, 100 to 600 microns, and more preferably 100 to 300 microns along its length.
77. The narrowest portion of the staple leg may extend from the skin entry point to 50 microns to 1 mm, 100 to 600 microns, and more preferably 100 to 300 microns along its length.
78. The cross-sectional area of the narrowest portion of the staple legs may be preferably 2,000 microns$^2$ to 1 mm$^2$, more preferably 10,000 to 360,000 microns$^2$, and most preferably 10,000 to 160,000 microns$^2$, which creates a smaller cross-sectional area than other parts of the staple leg such as the paddle or shovel section.
79. The staple legs may be in the shape of a paddle or shovel.
80. The staple legs may be in the shape of an arrowhead.
81. The staple legs may be in the shape of a house or triangle.
82. The staple legs include a tip area in the range of 1,000 to 100,000 microns$^2$, preferably 2,000 to 40,000 microns$^2$, and more preferably 3,000 to 10,000 microns$^2$, with other size tips within the scope of the invention.
83. The staple legs may have uniform width throughout their length.
84. The staple legs may have a non-uniform width throughout their length.
85. The staple may include a distance between opposing staple legs in a range from 1 to 30 mm, preferably 5 to 25 mm preferably, and most preferably 10 to 20 mm.
86. The length of the legs of the staples may range from 1 to 10 mm, preferably 2 to 8 mm, and more preferably 3 to 6 mm.
87. The vertical height of the deep skin staple is in a range from 1 mm to 10 mm, preferably 2 mm to 7 mm, and more preferably 3 mm to 6 mm. In an example, the vertical height of the deep skin staple is 5 mm.
88. The staple legs are designed to reduce pain upon application.
89. The staple legs are designed to reduce pain upon removal.
90. The staple legs have tips that reduce pain upon application.
91. The staple legs have tips that reduce pain removal.
92. The staple can include an array of legs that may contain more than one leg on each side of the array that is distal to the bridge.

93. The staple can include an array of legs that may contain two or more legs on each side of the array that is distal to the bridge.
94. The staple can include an array of legs that may contain three or more legs on each side of the array that is distal to the bridge.
95. The tips of individual legs in an array on a deep skin staple may be at distances from 1 to 15 mm apart, preferably 3 to 10 mm apart, and more preferably 6 to 8 mm apart.
96. The staple can be designed for use to close a wound of a certain wound depth.
97. The staple can be designed for use to close an entire wound of a certain wound depth.
98. The staple can be designed for use to close a portion of a wound of a certain wound depth.
99. The wound depth in example 97 can be 1 to 7 mm, preferably 2 to 5 mm, and most preferably 3 to 4 mm.
100. The staple can be designed for use on a certain part of the body.
101. The staple can be designed for use on the face.
102. The staple can be designed for use on the digits such as fingers or toes.
103. The staple can be designed for use on the extremities.
104. The staple can be designed for use on the back.
105. The staple can be designed for use on the abdomen or pelvis.
106. The staple can be designed for use on the chest.
107. The array of staples may incorporate multiple deep skin staples with legs that are described in examples 1-106.
108. The bridge of the staple may be elastic.
109. The bridge of the staple may be inelastic.
110. The bridge of the staple may contain a spring.
111. The bridge of the staple may contain two or more springs.
112. The array of staples may be formed into an array of interconnected staples.
113. The array of staples may be of any length or width.
114. The length of the bridge of the staple between the two ends of the array of legs may be 3 to 30 mm, preferably 5 to 25 mm, and more preferably 10 to 20 mm.
115. The deep skin staple may contain one array of legs.
116. The deep skin staple may contain an array of legs with one staple leg at each end.
117. The deep skin staple may contain an array of legs with two staple legs at each end.
118. The deep skin staple may contain an array of legs with multiple staple legs at each end.
119. The deep skin staple may contain two or more arrays of legs.
120. The deep skin staple containing multiple arrays of staple legs may contain an interconnector between two arrays (or between two deep skin staples coupled by an interconnector).
121. An array of deep skin staples may include a backing to interconnect each of the multiple deep skin staples in the array.
122. The deep skin staple can include an array of legs that may be at a distance along the length of the deep skin staple of 1 mm to 1 cm from one another, and preferably 2 mm to 15 mm from one another, and more preferably 3 to 10 mm from one another.
123. The deep skin staple can contain a variety of staples, staple legs, and arrays of different shapes, lengths, distances from one another.
124. The deep skin staple can contain a variety of staples of different shapes, lengths, and distances from one another.
125. The deep skin staple can contain a variety of staple legs of different shapes, lengths, distances from one another.
126. The deep skin staple can be incorporated into a variety of arrays of different shapes, lengths, and distances from one another.
127. The individual deep skin staples may be separated from each other along the wound length by 1 to 10 mm, preferably 2 to 8 mm, and more preferably 3 to 6 mm.
128. The deep skin staple can contain a variety of springs.
129. The backing may be removable or detachable.
130. The deep skin staple may be attached to the backing.
131. The deep skin staple may not be attached to the backing.
132. The backing may not be removable or detachable.
133. The backing may contain an opening.
134. The backing may contain one opening.
135. The backing may contain two or more openings.
136. The backing may not contain openings.
137. The backing may made of a material that enhances wound healing.
138. The backing may be made of a material that prevents or treats infection.
139. The backing may be made of a material that prevents or reduces scarring.
140. The backing may be made of a material that creates a moist wound environment.
141. The backing may contain an agent that enhances wound healing.
142. The backing may contain an agent that prevents or treats infection.
143. The backing may contain an agent that prevents or reduces scarring.
144. The backing may contain an agent that creates a moist wound environment.
145. The backing may be made of silicone, polyurethane or paper.
146. The backing may encompass one deep skin staple.
147. The backing may encompass two or more deep skin staples.
148. The backing may encompass all of the deep skin staples closing the wound.
149. An array of deep skin staples may contain one or more interconnectors that link individual deep skin staples into an array or multiple arrays of staples together.
150. The deep skin staple may contain one or more detachable interconnectors.
151. The spring structures used in connecting the staple legs or within the bridge portion between staple leg arrays may be sinusoidal, rectangular, circular, U-shaped, Z-shaped, or other shapes.
152. The staple may include legs of any vertical height, but preferably at a height that enables their insertion into or through the reticular skin layer or through a depth of tissue or organ associated with a wound or incision.
153. The staple may include legs of any vertical height, but preferably at a height that enables closure of the epidermis and dermis.
154. The staple may include legs of any vertical height, but preferably at a height that enables closure of all of the skin layers from the epidermis through the dermis.

155. The range of vertical heights can be anywhere from 1 to 10 mm with example deep skin staples including a height of 2-8 mm and 3-6 mm.
156. The range of vertical depths of the staple legs when applied to a wound range from 1 mm to 6 mm deep.
157. The deep skin staple may be formed to prevent or reduce scarring.
158. The deep skin staple may be formed to prevent scarring.
159. The deep skin staple may be formed to reduce scarring.
160. The deep skin staple in example 157 may prevent or reduce keloids or hypertrophic scars.
161. The deep skin staple in example 157 may prevent or reduce keloids.
162. The deep skin staple in example 157 may prevent or reduce hypertrophic scars.
163. An array of interconnected deep skin staples may be cut to the appropriate length to close the wound.
164. The array of interconnected deep skin staples may be cut to a length to match the size of the wound.
165. The deep skin staple may contain perforations in the backing so that its size can be reduced to close the wound.
166. The deep skin staple may be applied by one operator.
167. One deep skin staple may be applied to a wound.
168. Two or more deep skin staples may be applied to a wound.
169. The deep skin staple may be inflexible or inelastic.
170. The deep skin staple may be flexible or elastic.
171. Portions of the deep skin staple may be inflexible or inelastic.
172. Portions of deep skin staple may be flexible or elastic.
173. The deep skin staple may create wound eversion.
174. The deep skin staple may create uniform wound tension.
175. The deep skin staple may relieve wound tension.
176. The deep skin staple may off load wound tension.
177. The deep skin staple may reduce the wound's mechanical forces.
178. The deep skin staple may achieve force modulation of the wound.
179. The legs of the deep skin staple may be linear.
180. The legs of the deep skin staple may be non-linear, such as formed into a curved or jagged shape.
181. The shape of the legs of the deep skin staple may vary along its length.
182. The shape of the legs of the deep skin staple may facilitate penetration through the skin.
183. The shape of the legs of the deep skin staple may reduce pain upon insertion.
184. The shape of the legs of the deep skin staple may have an inward curvature from the tip to a portion of the legs above the tip.
185. The shape of the legs of the deep skin staple may have an inward curvature from the tip to a portion that is 0.5-3 mm, 1-2 mm, and preferably 0.5-1.5 mm above the tip.
186. The shapes of the legs may vary in individual deep skin staples in an array.
187. The legs of the deep skin staple may be designed to facilitate its removal.
188. The deep skin staple may be designed to facilitate its removal.
189. The array of staples may be designed to facilitate its removal.
190. The legs of the deep skin staple may be designed to reduce pain upon removal.
191. The deep skin staple may be designed to reduce pain upon removal.
192. The array of staples may be designed to reduce pain upon removal.
193. The wound closure device may be optimally formed to include an array of deep skin staples in which the staples are interconnected at a bridge of each staple. This will create more uniform closure since the individual staples will be at fixed distances from one another. It will also reduce costs of manufacturing since only one device needs to be made rather than several to close a longer wound.
194. The arrays of deep skin staples may be interconnected to one another such that they form one device. This will create more uniform closure since the individual staples or arrays of staples will be at fixed distances from one another. It will also reduce costs of manufacturing since only one device needs to be made rather than several to close a longer wound.
195. A first array of staples may be connected to a second array of staples via a backing.
196. A first array of staples may be connected to a second array of staples via an adhesive backing.
197. More than two arrays of staples may be connected to one another via a backing.
198. More than two arrays of staples may be connected to one another via an adhesive backing.
199. The staple may be designed such that they can reach into or through the entire reticular layer of the skin associated with a wound.
200. The staple may be designed such that they can reach into or through the entire reticular layer of the skin associated with an incision.
201. The staple may be designed such that they can reach into or through the entire reticular layer of the skin associated with a laceration.
202. The staple may be at a height that enables their insertion into or through the reticular skin layer associated with an incision that is able to prevent or reduce scarring.
203. The staple may be of a shape and surface area that is needed to relieve tension in the reticular layer of the skin associated with a wound to prevent or reduce collagen formation and fibrosis.
204. The staple may be of a shape and surface area that is needed to relieve tension in the reticular layer of the skin associated with an incision to prevent or reduce scarring.
205. The staple may be able to reach the depth of skin required to prevent or reduce scarring.
206. The staple may be able to reach the depth of skin required to relieve tension and prevent or reduce scarring.
207. The staple may be able to reach the depth of skin required to reduce mechanical force and prevent or reduce scarring.
208. The staple may be able to reach the depth of skin required to achieve force modulation and prevent or reduce scarring.
209. The staples may be at a distance from one another along the wound that provide the tensile strength required to close a wound.
210. The staples may be at a distance from one another along the wound that they reduce inflammation associated with movement of the skin.

211. The staples are optimally at sufficient distance from one another along the wound edges that they create uniform force modulation along the wound to prevent or reduce scarring.
212. The staple may be located 1 to 10 mm, preferably 2 to 8 mm, and more preferably 3 to 5 mm from one another along the wound edges.
213. The staples are optimally at sufficient distance from one another along the wound to prevent gaps.
214. The staples are optimally at sufficient distance from one another to prevent skin irritation.
215. The deep skin staple may incorporate a spring structure.
216. The deep skin staple may incorporate two or more spring structures.
217. The deep skin staple may incorporate one or more cantilever springs.
218. The deep skin staple may incorporate a spring structure to prevent or reduce scarring or fibrosis of a wound in the skin.
219. The deep skin staple may incorporate a spring structure to prevent or reduce scarring or fibrosis of an incision in the skin.
220. The deep skin staple may incorporate a spring structure to reduce skin irritation or inflammation.
221. The spring structure may be in the shape of a rectangle, square, circle, triangle, diamond, oval, sinusoid, or curve.
222. Each individual staple leg in a deep skin staple may connect to a spring structure.
223. Each individual staple leg in a staple may connect to one spring structure.
224. Each individual staple leg in a staple may connect to two or more spring structures.
225. Each individual staple leg in a staple may connect to one spring structure at each proximal end.
226. Each individual leg in a staple may connect to more than one spring structure at each proximal end.
227. The springs are incorporated into the leg of a staple such that they relieve tension or mechanical forces on the wound.
228. The springs may be incorporated into the legs of a staple such that they allow force modulation on the wound.
229. The springs may be incorporated into the legs of a staple such that they enable the overall deep skin staple to achieve adequate mechanical force to enable closure of the wound.
230. The springs may be incorporated into the legs of a staple such that they prevent or reduce scarring.
231. The springs may be incorporated into the legs of a staple to allow its movement with the skin that minimizes skin irritation.
232. The spring may be a cantilever spring.
233. The deep skin staple may contain one or more staple legs and one or more springs that prevent or reduce scarring.
234. The deep skin staple may contain staple legs that penetrate the skin in addition to springs that prevent or reduce scarring.
235. The deep skin staple may contain staple legs that penetrate the dermal layer in addition to springs that prevent or reduce scarring.
236. The deep skin staple may contain staple legs that penetrate the reticular layer of the dermis in addition to springs that prevent or reduce scarring.
237. The deep skin staple may contain staple legs that penetrate through the reticular layer of the dermis in addition to springs that prevent or reduce scarring.
238. The deep skin staple may be able to close a wound and reduce scarring.
239. The deep skin staple may be able to reduce mechanical force and prevent or reduce scarring.
240. The deep skin staple may be able to relieve tension and prevent or reduce scarring.
241. The deep skin staple may be able to achieve force modulation and prevent or reduce scarring.
242. The deep skin staple may be able to close a wound extending from the skin surface to the deep skin layer in one procedure.
243. The deep skin staple may be able to close a wound extending from the skin surface to the reticular dermis in one procedure.
244. The deep skin staple may be able to close a wound that extends into the deep skin layer in one procedure.
245. The deep skin staple may be able to close a wound that extends into the dermal skin layer in one procedure.
246. The deep skin staple may be able to close a wound that extends into the reticular dermal skin layer in one procedure.
247. The deep skin staple may be able to close a wound that extends into the majority of the reticular dermal skin layer in one procedure.
248. The deep skin staple may be able to close a wound that extends into the dermal skin layer in one procedure and prevents or reduces scarring.

Application Instrument:

Providing an applicator for applying the deep skin staples has a number of advantages. An applicator may help generate more force than manual application of the deep skin staple to reach the reticular layer of the dermis which is required for force modulation to be effective in preventing or reducing scarring. Deeper penetration of the skin using an applicator will allow the deep skin staple to close deeper layers of skin including the dermis and in particular the reticular dermis. The applicator may also provide more consistent forces that will allow more uniform depth of penetration of the legs of the deep skin staples in the skin, and optimally in the reticular dermal layer of the skin. An applicator may provide more consistent application than can be achieved with manual application in terms of the location along the wound surface—both distance of the staples from the wound edges and also distance of the staple from one another along the length of the wound. An applicator may also provide more consistent tension to be applied to close the wound with the device which may vary when performed manually. In addition, it can be designed to optimize wound eversion, which may help improve cosmetic results as described below.

The applicator may contain materials that allow it to be elastic or deformable. An elastic applicator allows it to insert staples over skin surfaces that may not be flat such as curved or variable shaped surfaces. This could include skin over joints as well as abdominal or pelvic skin, especially in obese patients.

The applicator can be designed as a specialized element to operate in a manner which is similar to staplers that are routinely used by physicians to close wounds so should require minimal training and expertise to utilize. Alternatively, the applicator can be an alternative instrument that achieves uniform application of the staples and insertion into the reticular dermal layer of the skin. The applicator could be a roller or punch. The applicator could incorporate an element that provides force to insert the staples into the skin. The application instrument can be delivered with a deep skin staple, or an array of deep skin staples attached for manual application.

The following examples relate to application instruments for use in applying deep skin staples, such as those illustrated in FIGS. 1A-4I and 8A-11E. The application instrument discussed in the following examples is illustrated below in FIGS. 5A-6. However, not all of the examples below relate to the illustrated application instrument.

The applicator can be used to insert conventional staples such as wide or regular staples. This would have the same advantages as those described above for use of the applicator with deep skin staples.

1. The applicator may be used to insert deep skin staples.
2. The applicator may be used to insert conventional staples.
3. The applicator may be disposable.
4. The applicator may be reusable.
5. The applicator may insert one deep skin staple into the skin.
6. The applicator may insert two or more deep skin staples into the skin.
7. The applicator may be transparent.
8. The applicator may be opaque.
9. The applicator may be made out of metal.
10. The metal in example 9 may consist of titanium, aluminum, or stainless steel, or other metals commonly used in medical device manufacturing.
11. The applicator may be made out of a polymer.
12. The polymer in example 11 may consist of polymethylmethacrylate, polycarbonate, acrylic, polyethylene, acetal (Delrin), nylon, PVC, ABS, polypropylene, polyester, polystyrene, PTFE, PEEK, or others.
13. The applicator may be wider than the deep skin staple array.
14. The applicator may be narrower than the deep skin staple array.
15. The applicator may vary in width or length.
16. The applicator may be in the shape of a rectangle.
17. The applicator may in the shape of a square.
18. The applicator may incorporate a handle.
19. An applicator may include marks on it to help locate the staples.
20. An applicator may include marks on it to help locate the staple array.
21. The applicator may be removable.
22. The applicator may be permanent and remain attached to the deep skin staple or deep skin staple array.
23. The applicator may contain two components that detach from one another after the device (e.g., deep skin staple or deep skin staple array) is applied to the skin.
24. The applicator may be a single component that is permanently deformed after the device is applied to the skin.
25. The permanent deformation described in example 24 may be due to local yielding of its materials due to local geometry.
26. The applicator and staple may be pre-assembled.
27. The applicator and staple may be sterile.
28. The applicator may include warnings and/or instructions on alignment and application of the staple.
29. The instructions mentioned in example 28 may be a feature of the applicator.
30. The instructions mentioned in example 28 may be a separate component of the applicator and/or staple.
31. The applicator's width may be cut to length depending on the size of the wound.
32. The material of the applicator may allow turning or adjustment of staple locations during application.
33. The applicator may be incorporated into the device or be a separate instrument.
34. The applicator may be able to provide the force required to reach the depth of skin (deep skin as defined herein), sufficient to prevent or reduce scarring.
35. The applicator may be able to provide the force required to insert the staples into the dermis of the skin or through a depth of skin sufficient to prevent or reduce scarring.
36. The applicator may be able to provide the force required to insert the staples into the reticular layer of the skin sufficient to prevent or reduce scarring.
37. The applicator may be formed so that the staples can be applied with manual force.
38. The applicator may contain a feature that allows it to provide force to insert the staples into the skin.
39. The applicator may contain a feature that allows it to provide force to insert the staples into the dermal layer of the skin.
40. The applicator may contain a feature that allows it to provide force to insert the staples into the reticular layer of the dermis.
41. The applicator may contain a feature that allows it to consistently provide force on the skin.
42. The applicator may contain a feature that allows it to provide uniform force on the skin.
43. The applicator may be able to provide the force required to reach the depth of skin (deep skin as defined herein), sufficient to close a deep wound.
44. The applicator may be able to provide the force required to reach the depth of skin (deep skin as defined herein), sufficient to close a dermal wound.
45. The applicator may be able to provide the force required to reach the depth of skin (deep skin as defined herein), sufficient to close a wound that extends into the reticular dermis.
46. The applicator may contain a feature that enable the generation of force to close a dermal wound.
47. The applicator may contain a feature that enable the generation of force to close a wound that extends into the reticular dermis.
48. The applicator may consist of a stapler.
49. The applicator may consist of a punch.
50. The applicator may consist of a roller.
51. The applicator may consist of an elongate body including a handle opposite a pair of features to secure a deep skin staple.
52. The applicator of example 46 can include a release notch to enable release of the deep skin staple after application.
53. The applicator of example 46 can include the pair of features being opposing rounded wedge structures that create a friction fit with opposing ends of a deep skin staple or array of deep skin staples.
54. The applicator is made of a clear and rigid material.
55. The applicator may have an optional alignment guide for creating even tension and for staple placement.
56. The applicator together with the staples are packaged as a sterile device.
57. The applicator may be able to apply the staples through a depth of skin sufficient to close a wound.

58. The applicator may be able to apply the staples through a depth of skin sufficient to close a wound extending into the dermis.
59. The applicator may be able to apply the staples through a depth of skin sufficient to close a wound extending into the reticular dermis.
60. The applicator may be able to apply the staples through a depth of skin sufficient to close a wound extending through the reticular dermis.
61. The applicator may be able to apply the staples into the reticular layer of the skin or through a depth of skin sufficient to reduce tension on the wound.
62. The applicator may be able to apply the staples into the reticular layer of the skin.
63. The applicator may be able to apply the staples through a depth of skin sufficient to reduce tension on the wound.
64. The applicator that may be able to apply the staples into the reticular layer of the skin or through a depth of skin sufficient to reduce mechanical force on the wound.
65. The applicator may be able to apply the staples through a depth of skin sufficient to reduce mechanical force on the wound.
66. The applicator that may be able to apply the staples into the reticular layer of the skin or through a depth of skin sufficient to achieve force modulation on the wound.
67. The applicator may be able to apply the staples through a depth of skin sufficient to achieve force modulation on the wound.
68. The applicator may include a wedged geometry to hold the deep skin staple or staple array via friction until applied.
69. The applicator may include a geometry that creates a pivot for releasing the deep skin staple or staple array when rotated.
70. The applicator can be a tab coupled directly to the deep skin staple or attached to a backing adhered to the deep skin staple.
71. The applicator including a tab can be used to pull to close the wound.
72. The applicator may be used to apply deep skin staples into skin surfaces that are not flat.
73. The applicator may be used to apply deep skin staples into skin surfaces that are curved.
74. The applicator may be used to apply deep skin staples into variable skin surfaces.
75. The applicator may be used to apply deep skin staples into the skin over joints.
76. The applicator may be used to apply deep skin staples into the skin in the abdominal and pelvic areas.
77. The applicator may be elastic.
78. The applicator may be deformable.
79. The applicator may contain components that are both inelastic and elastic.
80. The applicator may contain components that are both non-deformable and deformable.
81. The applicator may contain a deformable material.
82. The applicator may contain an elastic material.
83. The applicator may be made of a rubber material.
84. The applicator may be made of a solid rubber material.
85. The applicator may be made of a foam rubber material.
86. The applicator may be made of rubber material such as Aflas, Buna-N, Vinyl Rubber, Butyl, EPDM, Fluorosilicone, Silicone, Kalrez, Natural rubber, Neoprene, Polyurethane, Santoprene, SBR, Viton Fluoroelastomer.
87. The applicator may be clear/transparent.
88. The applicator may be opaque.
89. The applicator may be manufactured by molding.
90. The applicator may be manufactured by casting.
91. The applicator may be manufactured by machining.
92. The applicator may be manufactured by extrusion.
93. The applicator may be made of materials that is flexible and can conform over skin surfaces.
94. The applicator may be flexible yet rigid enough to allow staple placement and application across the wound.
95. The applicator may hold the staple by mechanical means.
96. The applicator may release the staple after applying across the wound by mechanical means.
97. The applicator may utilize adhesives to hold the staple.
98. The applicator may allow applying of multiple staples at a time.
99. The applicator may allow local turning of staples to accommodate a non-straight wound.
100. The applicator may create even spacing between staple legs.

Eversion Examples:

There is a natural tendency for wounds closed with sutures or staples to form depressed scars. This results from contractile forces that occur during wound healing. Eversion of the wound counteracts this tendency and thus reduces scarring. Thus, the act of eversion allows the final wound to lay flat, rather than further contracting from a flat plane to eventually become depressed at the center (inverted). To overcome this tendency during stapling of wounds, a second operator is required to bring the wound edges together in an attempt to evert the wound as the first operator staples the wound closed. This is only somewhat effective and subject to large variability depending on the operators. There is thus a need for stapling procedures that are able to achieve more uniform and consistent eversion and ideally without the need for a second operator to evert the wound that requires additional resources. Finally, the deep skin staples are designed to promote eversion by forming them so that the legs extending from the surface of the skin to the tips of the legs angle towards the center of the wound Within the following examples, the term "staple" is intended to be interpreted as a deep skin staple or an array of deep skin staples.

1. The deep skin staple can be applied by one operator.
2. The staples are designed to evert the wound.
3. The staples are structured so that the legs extending from the surface of the skin to the tips of the legs angle towards the center of the wound.
4. The vertical portion of the staple leg facing the wound is at a less than 90-degree angle with respect to the surface of the deep skin staple that is on the surface of the skin.
5. The staple can include straight or substantially straight legs.
6. The deep skin staple may achieve eversion of the wound.
7. The applicator may achieve eversion of the wound.
8. The applicator used together with the deep skin staple may evert the wound.

Backing or Cover Examples:

The device containing a single deep skin staple or an array of deep skin staples (where an array includes a series of connected or non-connected deep skin staples aligned on a backing to close a longer wound) may contain a backing or cover. In this example, the backing allows more consistent and uniform placement of the staples.

The backing may be detachable or removable or the backing may not be detachable or removable also referred to as permanent.

A permanent backing or cover provides additional securement of the deep skin staple to the skin. This backing or cover also provides a seal of the wound to prevent bacterial entry. This backing or cover also provides more uniform tension along the edges of the wound which further reduces scarring. A permanent backing may ensure more uniform tension along the wound to reduce scarring. It will also provide a barrier that prevents bacterial entry and resulting infections. A permanent backing could be made out of materials that can be used to treat wounds. These include agents or materials that prevent infection or promote wound healing. It also includes materials or agents that prevent or reduce scarring such as silicone, polyurethane, or paper.

A removable backing makes it possible to provide another cover or backing after the wound has been closed. This may be advantageous because there will be less drainage and bleeding which can cause the skin or backing or cover to get wet risking detachment of the deep skin staple. This also makes it feasible to apply another cover directly over the wound (e.g., Tegaderm™, 3M™, Saint Paul, MN) that may be preferred by physicians or medical personnel. A detachable backing also makes it possible to directly apply products on the wound. This may be helpful since these products will directly interact with the wound rather than be separated from the wound with a non-detachable backing. These products include wound care products (e.g., wound dressings) and those that promote wound healing, hemostatic agents, tissue adhesives, anti-bacterial agents, and products that reduce scarring (e.g., silicone sheets and gels). Within the following examples, the term "staple" is intended to be interpreted as a deep skin staple or an array of deep skin staples.

In another example, a wound covering can be applied to the wound in advance of application of one or more deep skin staples. The deep skin staples can then be applied across the wound through the wound covering. The deep skin staples would operate to keep the wound covering in place during the healing process and still provide the other scar reduction characteristics discussed throughout this specification. A wound covering applied in this matter could include additional scar reduction properties as discussed above.

1. The backing may be detachable.
2. The backing may be non-detachable or removable.
3. The staple may be attached to the backing.
4. The staple may not be attached to the backing.
5. The backing may enable more uniform wound tension that prevents or reduces scarring.
6. The deep skin staple may contain a backing that reduces scarring, such as paper tape, polyurethane sheets, or silicone sheets or gels.
7. The material for the backing may be elastic and flexible.
8. The material for the backing may be non-elastic and inflexible.
9. The material for the backing may contain an adhesive.
10. The adhesive may be any medical adhesive material including acrylic, silicone, hydrocolloid, rubber, or hybrids of these.
11. The material for the backing may not contain an adhesive.
12. The backing may comprise a portion that contains adhesive and a portion with no adhesive.
13. The backing may contain adhesive around its periphery and no adhesive elsewhere.
14. The backing may contain adhesive around its periphery and no adhesive in its center.
15. The material for the backing may comprise silicone, paper, or polyurethane, or another polymer.
16. The backing may contain one or more openings.
17. The openings may be in the form of slits.
18. The backing may not contain openings.
19. The backing may be designed to be able to be cut to reduce its size.
20. The backing may contain perforations to reduce its size.
21. The material may have sufficient elasticity to enable relief of wound tension.
22. The material may have sufficient elasticity to reduce mechanical force.
23. The backing may be attached to the deep skin staple.
24. The backing may be incorporated into the deep skin staple.
25. The backing may not be incorporated into the deep skin staple.
26. The backing may be a cover that is not attached to the deep skin staple prior to application.
27. One backing or cover may be applied over the deep skin staple.
28. More than one backing or cover may be applied over the deep skin staple.
29. The backing may connect multiple arrays of staples into a single deep skin staple.
30. The backing or cover may be removed followed by treating the wound with dressings, hemostatic agents, tissue adhesives, anti-bacterial agents, wound healing agents, or anti-scarring products (e.g., silicone gel or sheets).

Monitoring Tension Concept:

The application instrument (e.g., applicator) may contain an element that allows the force across the wound to be measured. This enables optimal tension to be determined to close the wound and reduce scarring. It also enables optimal force to be determined to close the wound. Within the following examples, the term "staple" is intended to be interpreted as a deep skin staple or an array of deep skin staples.

1. The applicator may contain a feature that measures the tension or mechanical force across the wound.
2. The applicator may contain a feature that indicates when optimal tension is generated across the wound.
3. The applicator may contain a feature that indicates when optimal mechanical force is generated across the wound.
4. The applicator may contain a feature that indicates when optimal force is generated to close the wound.
5. The applicator may contain a feature that contains two lines that overlap when optimal tension is generated across the wound.
6. The applicator may contain a feature that contains paper that tears when optimal tension is generated across the wound.

7. The applicator may contain a feature that contains paper with perforations that tear when optimal tension is generated across the wound.
8. The features of items 1-7 may be attached to the backing.
9. The features of items 1-7 may be incorporated into the backing.

Measuring Attachment Pressure Concept:

There may be an element that measures the force exerted to insert the staples into the skin in general and at various levels to obtain optimal wound closure and force modulation. Within the following examples, the term "staple" is intended to be interpreted as a deep skin staple or an array of deep skin staples. The term "feature" is intended to be interpreted as the measurement device that can be incorporated into various structures, such as an applicator, a backing, the deep skin staple, or the staple array.

1. The deep skin staple may contain a feature that measures the force generated by pressing on the deep skin staple to attach it to the skin.
2. The deep skin staple may contain a feature that measures the force generated by manually pressing on the deep skin staple to attach it to the skin.
3. The deep skin staple may contain a feature that measures the force generated by pressing an applicator on the deep skin staple to attach it to the skin.
4. The deep skin staple may contain a feature that measures the force required to insert the staple into the skin.
5. The deep skin staple may contain a feature that measures the force required to insert the legs of the staple to their maximum length.
6. The deep skin staple may contain a feature that measures the force required to insert the legs of the staple into the dermis
7. The deep skin staple may contain a feature that measures the force required to insert the legs of the staple into the reticular layer of the dermis
8. The feature may be incorporated into the backing.
9. The feature may be attached to the backing.
10. The feature may be attached to the staple.
11. The feature may be attached to the staple array.
12. The feature may be incorporated into the deep skin staple.
13. The feature may be attached to the staple array.
14. The feature may consist of a visual signal.
15. The visual signal may be a color change incorporated into part or all of the deep skin staple.
16. The visual signal may be release of a fluid incorporated into part or all of the deep skin staple.

Feature to Locate Staples for Applying Pressure to Insert them in the Skin:

Identifying where pressure should be applied is essential to achieve proper insertion of the deep skin staples into the skin. A marker to identify where the staples and legs are located provides a method to find and provide the optimal locations of where force should be applied in areas containing deep staples. Within the following examples, the term "staple" is intended to be interpreted as a deep skin staple or an array of deep skin staples. The term "mark" is intended to be interpreted as a feature or mechanism to assist in locating an application location for a deep skin staple.

1. A deep skin staple with marks over staples.
2. A deep skin staple with marks on staples.
3. A deep skin staple with a mark on the staple array.
4. A deep skin staple with a mark over the staple array.
5. A deep skin staple with a mark on the backing over staples.
6. A deep skin staple with a mark on the backing over staple legs.
7. A deep skin staple with a mark on the backing over the staple array.
8. A deep skin staple with a mark over staples to identify where force should be applied to insert the staples into the skin.
9. A deep skin staple with a mark over staple legs to identify where force should be applied to insert the staple legs into the skin.
10. A mark that contains a color.
11. A mark that is a line, square, rectangle, circle, oval, or star shape.
12. A line that extends along the staples.
13. A line that extends along the staple legs.
14. A line the extends along the staples along with a mark that identifies the location of the staples.
15. A line the extends along the staple legs along with a mark that identifies the location of the staple legs.

Kit Concepts:

The following concepts are focused on how a kit may be packaged for use. A kit can include all of the elements needed for a particular procedure using the backing, staples and/or staple applicator. Deep skin staple refers to either an individual staple, multiple individual staples, an individual array of interconnected staples, more than one array of interconnected staples, or an array of non-interconnected staples on a common backing. Within the following examples, the term "staple" is intended to be interpreted as a deep skin staple or an array of deep skin staples. The term "deep skin staple" is intended to be interpreted as a deep skin staple or an array of deep skin staples. Kits can also be designed to be used by certain specialties, in different types of surgeries, or different locations on the body. In the examples below, kit also refers to a package.

1. The deep skin staple and applicator may be formed into a kit.
2. The kit may contain instructions on how to use its contents.
3. The deep skin staple may be provided as a kit that includes one or more individual deep skin staples or array of interconnected deep skin staples.
4. The kit may contain different sizes of staples.
5. The kit in example 3 may contain conventional and deep staples.
6. An array of staples and a backing or cover may be provided separately as a kit.
7. The deep skin staple and cover or backing may be provided as a kit.
8. The deep skin staple and agents or materials that are hemostatic, promote wound healing, eliminate bacteria, prevent or reduce scarring, are wound dressings, or are wound covers may be provided as a kit.
9. The anti-scarring treatments may contain silicone and be incorporated into sheets or gels.
10. The deep skin staple, applicator, and cover or backing may be provided as a kit.
11. The deep skin staple, applicator, and cover or backing may be provided as a kit.
12. The kits may contain different sizes of staples, different sizes of arrays, different number of deep skin staples, different applicators, different backings for different types of procedures, regions of the body, or specialties.
13. The kit may be designed for closing acute wounds.
14. The kit may be designed for closing lacerations.
15. The kit may be designed for closing skin tears.

16. The kit may be designed for surgery.
17. The kit may be designed for closing incisions.
18. The kit may be designed for closing port sites.
19. The kit may be designed for emergency medicine.
20. The kit may be designed for trauma.
21. The kit may be designed for closing chronic wounds.
22. The kit may be designed for closing pressure ulcers, diabetic ulcers, venous ulcers, or arterial ulcers.
23. The kit may be designed for plastic surgery.
24. The kit may be designed for orthopedics.
25. The kit may be designed for joint surgery.
26. The kit may be designed for dermatology.
27. The kit may be designed for use on the face.
28. The kit may be designed for use on the digits such as the fingers or toes.
29. The kit may be designed for use on the extremities.
30. The kit may be designed for in the abdomen or pelvis.
31. The kit may be designed for use on the back.
32. The kit may be designed for use on the chest.
33. The kit may incorporate agents or materials to stop bleeding, promote wound healing, prevent or treat infection, or reduce or prevent scarring.

Clinical Use Concepts:

The following concepts focus on application of the deep skin staple and/or an array of deep skin staple devices within a surgical or other clinical setting, including method of use, treatment focus, and other related concepts. Deep skin staple refers to either an individual staple, an individual array of interconnected staples, an individual array of non-interconnected staples on a backing, more than one array of interconnected staples, an individual array with a backing or cover, or multiple arrays with a backing or cover. Within the following examples, the term "staple" is intended to be interpreted as a deep skin staple or an array of deep skin staples.

1. The deep skin staple may be used to close the skin.
2. The deep skin staple may be applied by one operator.
3. The deep skin staple may be applied by two or more operators.
4. The deep skin staple may be applied with an applicator.
5. The deep skin staple may be applied manually.
6. The deep skin staple may be applied by pressing down on it to affix the deep skin staple to the skin.
7. The deep skin staple may be applied by pressing down on the entire deep skin staple to affix the deep skin staple to the skin.
8. The deep skin staple may be applied by affixing one side of the deep skin staple to the skin and then closing the wound by pulling on the other side of the deep skin staple and then affixing it to the skin.
9. The deep skin staple may be applied by affixing one side of the deep skin staple to the skin and then closing the wound by sliding a finger across the deep skin staple to close the wound.
10. The deep skin staple may be applied manually by pressing down on it to affix the deep skin staple to the skin.
11. The deep skin staple may be applied manually by pressing down on the entire deep skin staple to affix the deep skin staple to the skin.
12. The deep skin staple may be applied manually by affixing one side of the deep skin staple to the skin and then closing the wound by pulling on the other side of the deep skin staple and then affixing it to the skin.
13. The deep skin staple may be applied manually by affixing one side of the deep skin staple to the skin and then closing the wound by sliding a finger across the deep skin staple to close the wound.
14. The deep skin staple may be applied using an applicator to press down on it to affix the deep skin staple to the skin.
15. The deep skin staple may be applied using an applicator to press down on the entire deep skin staple to affix the deep skin staple to the skin.
16. The deep skin staple may be applied using an applicator to affix one side of the deep skin staple to the skin and then closing the wound by pulling on the other side of the deep skin staple and then affixing it to the skin.
17. The deep skin staple may be applied using an applicator to affix one side of the deep skin staple to the skin and then closing the wound by sliding a finger across the deep skin staple to close the wound.
18. The deep skin staple may be applied on the wound.
19. The deep skin staple may be applied on an acute wound.
20. The deep skin staple may be applied on a chronic wound.
21. The deep skin staple may be applied to prevent or reduce scarring.
22. The deep skin staple may be applied to prevent scarring.
23. The deep skin staple may be applied to reduce scarring.
24. The deep skin staple may be applied to prevent or reduce scarring of an acute wound.
25. The deep skin staple may be applied to prevent or reduce scarring of a chronic wound.
26. The deep skin staple may be applied to close a wound.
27. The deep skin staple may be applied to close an acute wound.
28. The deep skin staple may be applied to close a chronic wound.
29. The deep skin staple may be applied to prevent or reduce keloid scarring.
30. The deep skin staple may be applied to prevent or reduce hypertrophic scarring.
31. Two or more deep skin staples may be applied over the wound.
32. Two or more deep skin staples may be applied to prevent or reduce scarring.
33. The deep skin staple may be used to reduce or prevent scarring associated with irritation or inflammation.
34. The deep skin staple may be used to reduce or prevent scarring in the skin due to trauma, an iatrogenic cause such as an insertion site for a catheter or surgical drain, surgical incision or port site related to laparoscopic and robotic surgeries, insertion sites associated with surgical drains, catheters, and tubing as well as burns, inflammation, irritation, or skin ulcers.
35. The deep skin staple may be used to reduce or prevent scarring due to an injury to the skin caused by scrapes, lacerations, skin tears, abrasion, surgical procedures (e.g., caused by minimally invasive surgery, laparoscopic surgery, robotic surgery, incisional biopsies, general surgery, and cosmetic surgery), trauma, denuded skin, burns, ulcers (e.g., diabetic ulcers, ulcers from vascular insufficiency, skin ulcers such as pressure ulcers, diabetic ulcers venous ulcers, arterial ulcers), or burns, or other skin problems (e.g., allergies)).
36. The deep skin staple may be used to reduce or prevent scarring that is due to wounds that are superficial (e.g., affecting merely the epidermis or surface of tissue or organ) or deeper (e.g., lesions which affect layers of skin or tissue at depths which are beneath the epidermis) or surface of the skin extending to the dermis.

37. The deep skin staple may be used to prevent or reduce scarring or fibrosis of wounds of any length or shape, e.g., in some embodiments, wounds are straight, jagged, or curved.
38. The deep skin staple may be used to prevent or treat scarring or fibrosis in various layers of the skin.
39. The deep skin staple may be used to prevent or reduce scarring or fibrosis in the skin.
40. The deep skin staple may be used to reduce or prevent scarring of the skin.
41. The deep skin staple may be used to reduce or prevent scarring associated with associated with acute wounds.
42. The deep skin staple may be used to reduce or prevent scarring associated with surgical incisions.
43. The deep skin staple may be used to reduce or prevent scarring associated with lacerations.
44. The deep skin staple may be used to reduce or prevent scarring associated with skin tears.
45. The deep skin staple may be used to reduce or prevent scarring associated with port sites.
46. The deep skin staple may be used to reduce scarring associated with insertion or port sites due to surgery, arthroscopy, arthroscopic surgery, laparoscopy, or insertions of tubing, catheters, surgical drains, or other apparatus.
47. The deep skin staple may be used to reduce or prevent scarring associated with Caesarean sections.
48. The deep skin staple may be used to prevent or reduce scarring associated with surgery.
49. The deep skin staple may be used to prevent or reduce scarring associated with plastic surgery.
50. The deep skin staple may be used to prevent or reduce scarring associated with cosmetic surgery.
51. The deep skin staple may be used to prevent or reduce scarring associated with liposuction.
52. The deep skin staple may be used to prevent or reduce scarring associated with breast reconstructive surgery.
53. The deep skin staple may be used to prevent or reduce scarring associated with breast augmentation surgery.
54. The deep skin staple may be used to prevent or reduce scarring associated with breast reduction surgery.
55. The deep skin staple may be used to prevent or reduce scarring associated with abdominoplasty.
56. The deep skin staple may be used to prevent or reduce scarring associated with a facial lift surgery.
57. The deep skin staple may be used to prevent or reduce scarring associated with body, buttocks, arm and leg lift surgeries.
58. The deep skin staple may be used to prevent or reduce scarring associated with dermatologic surgery.
59. The deep skin staple may be used to prevent or treat scarring associated with open surgery.
60. The deep skin staple may be used to prevent or treat scarring associated with laparoscopic or robotic surgery.
61. The deep skin staple may be used to prevent or treat scarring associated with cardiothoracic surgery.
62. The deep skin staple may be used to prevent or treat scarring associated with spine surgery.
63. The deep skin staple may be used to prevent or treat scarring associated with orthopedic surgery.
64. The deep skin staple may be used to prevent or treat scarring associated with joint surgery, including knee, hip, and shoulder arthroplasties.
65. The deep skin staple may be used to prevent or treat scarring associated with foot and ankle surgeries.
66. The deep skin staple may be used to prevent or treat scarring associated with vascular surgery.
67. The deep skin staple may be used to prevent or reduce scarring associated with trauma.
68. The deep skin staple may be used to prevent or reduce scarring associated with chronic wounds.
69. The deep skin staple may be used to prevent or reduce scarring associated with pressure ulcers, diabetic ulcers, venous ulcers, or arterial ulcers.
70. The deep skin staple may be used to prevent or reduce scarring associated with insertion sites associated with chest tubes, other tubing, catheters, or surgical drains.
71. The deep skin staple may be used to prevent or treat scarring on the head.
72. The deep skin staple may be used to prevent or treat scarring on the face.
73. The deep skin staple may be used to prevent or treat scarring on the neck.
74. The deep skin staple may be used to prevent or treat scarring on the trunk.
75. The deep skin staple may be used to prevent or treat scarring on the abdomen.
76. The deep skin staple may be used to prevent or treat scarring on the pelvis.
77. The deep skin staple be used to prevent or treat scarring on the chest.
78. The deep skin staple may be used to prevent or treat scarring on the back.
79. The deep skin staple may be used to prevent or treat scarring on the extremities.
80. The deep skin staple may be used to prevent or treat scarring on the hands.
81. The deep skin staple may be used to prevent or treat scarring on the foot and ankle.
82. The deep skin staple may be used to prevent or treat scarring on the digits such as fingers and toes.
83. The deep skin staple may be used to reduce or prevent a keloid scar.
84. The deep skin staple may be used to reduce or prevent a hypertrophic scar.
85. The deep skin staple may be used to reduce or prevent an atrophic scar.
86. The deep skin staple may be used to reduce or prevent contractures.
87. The deep skin staple may be used to reduce or prevent contractures in the skin.
88. The deep skin staple may be used to reduce or prevent contractures in the skin over joints.
89. The deep skin staple may be used with other products to treat wounds.
31. The deep skin staple may be used with dressings, hemostatic agents, tissue adhesives, anti-bacterial agents, or wound healing agents.
90. The deep skin staple may be used with other products to close wounds.
91. The deep skin staple may be used with other wound closure products to prevent or reduce scarring.
92. The deep skin staple may be used with adhesive bandages, SteriStrips, tissue adhesive, conventional medical staples, sutures, Zipline®, BandGrip®, Clozex®, and DermaClip®.
93. The deep skin staple may be used with other products or procedures to prevent or reduce scarring including corticosteroids, dressings, laser therapy, cryotherapy, other tension-relieving deep skin staples, scar treatment surgery, dermabrasion, chemical peels, vacuum therapy, vacuum massage therapy, pressure, silicone sheets or gels, polyurethane sheets, and paper tape.
94. The deep skin staple may be used with other products or procedures that affect one or more biochemical pathways that produce scarring.
95. The deep skin staple may be used with products that inhibit FAK to prevent or reduce scarring.
96. The deep skin staple may be used with products that inhibit YAP to prevent or reduce scarring.
97. The deep skin staple may be used with wound care deep skin staples, such as dressings, biosimilar skin products, skin grafts, or negative pressure wound therapy products.
98. The deep skin staple may be used with agents that promote wound healing.
99. The deep skin staple may be used with microMend®.
100. The deep skin staple may be used with an antibiotic.
101. The deep skin staple may be used with an antiseptic.
102. The deep skin staple may be used with a hemostatic agent.
103. The deep skin staple may be used with an anti-scarring agent.
104. The deep skin staple may be used with an anti-scarring agent containing silicone incorporated into sheets or gels.
105. The deep skin staple may be applied immediately after the occurrence of the wound.
106. The deep skin staple may be applied within one minute to three years, 30 minutes to one hour, one hour to four hours, four hours to 12 hours, 12 hours to one day, one day to one week, one week to two weeks, two weeks to one month, one month to two months, two months to four months, four months to eight months, eight months to two years, two years to three years, or more than three years after the occurrence of the wound.
107. The deep skin staples may be applied to the skin for a time sufficient to prevent or treat scarring.
108. The deep skin staples may be applied serially to the skin for any time sufficient to prevent or treat scarring ranging from 5 days to one year, which is optimally 4 weeks to nine months and more specifically, 8 weeks to 6 months.
109. Deep skin staples may be applied to the skin for a period of two days to four weeks, and preferably 7 to 14 days. Use exceeding 14 days may require application of a new deep skin staple or deep skin staples.
110. More than one of the deep skin staples may be applied to prevent or reduce scarring or fibrosis.
111. The deep skin staples may be applied in a linear fashion, such as a linear array of staples. In this example, linear can refer to one or more staples forming a straight or nearly straight line, where the individual staples may be interconnected along the central spring structure.
112. The deep skin staples may be applied in a non-linear fashion. In this example, non-linear refers to one or more staples applied to a wound in a non-uniform manner that does not form a straight or nearly straight line. The staples may or may not be interconnected when applied in a non-linear fashion.
113. The deep skin staples may be applied in a curvilinear fashion.
114. A single deep skin staple may be applied in a linear fashion.
115. A single deep skin staple may be applied in a non-linear fashion.
116. The deep skin staple may be removed manually.
117. The deep skin staple may be removed with an instrument.
118. The deep skin staple that may be used to treat humans
119. The deep skin staple that may be used to treat animals.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements). The figures illustrate various aspects of example force modulating tissue staples and applicator concepts.

FIGS. 4A-4I are various views of a deep skin staple structure according to multiple embodiments of the present invention.

FIGS. 5A-5D are various views of a deep skin staple application instrument according to one embodiment of the present invention.

DETAILED DESCRIPTION OF THE DRAWINGS

The embodiments of the present disclosure relate to improved devices for closing skin wounds including incisions, lacerations, skin tears and port sites. The devices discussed herein include deep skin force modulating staples ("deep skin staples") that include a central bridge structure with multiple staple legs connected via spring arms. Each staple leg includes a tip, a shovel, and an angled connection to the spring arm. The spring arms in each embodiment are designed to provide reversible expansion upon the application of a force that modulates tension on different portions of a wound. In some examples, the spring arm structure in combination with the staple leg operates to modulate tension within various layers of skin involved in the wound. In some examples, the deep skin staple is designed to reduce or modulate tension within the reticular layer of the dermis, which results in a reduction in collagen formation and fibrosis. Reducing collagen formation and fibrosis has been linked to a reduction in scarring during wound healing. In some examples, the deep skin staples and applicator (e.g., applicator instrument) are designed to generate wound eversion, which is also known to reduce scarring during the healing process. In certain examples, an additional spring structure is added into the bridge portion to further enhance the ability for the deep skin staple to modulate forces across the wound.

Figure 1A:
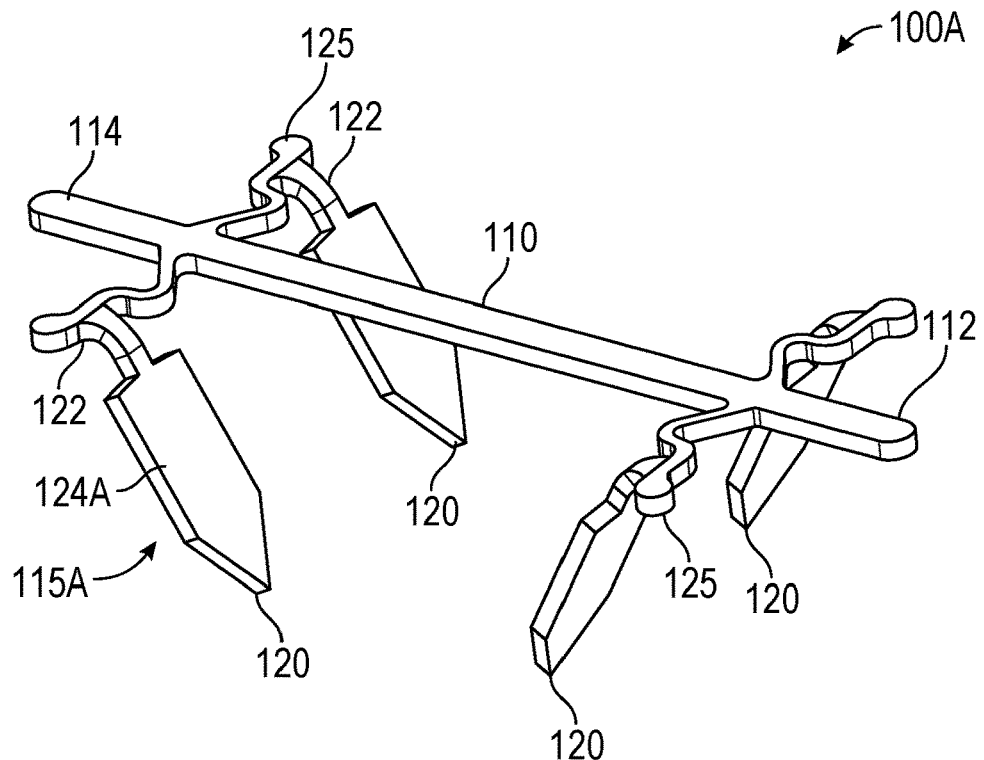
FIGS. 1A-1F are various views of a deep skin staple structure according to multiple embodiments of the present invention.
Figure 1B:
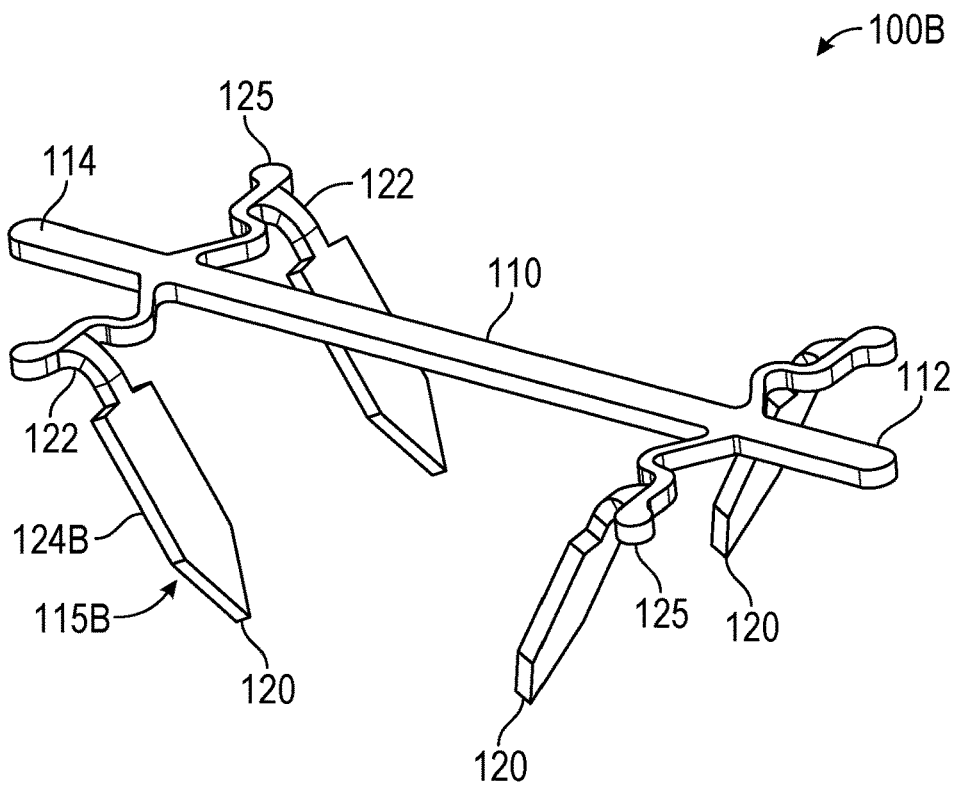
Figure 1C:
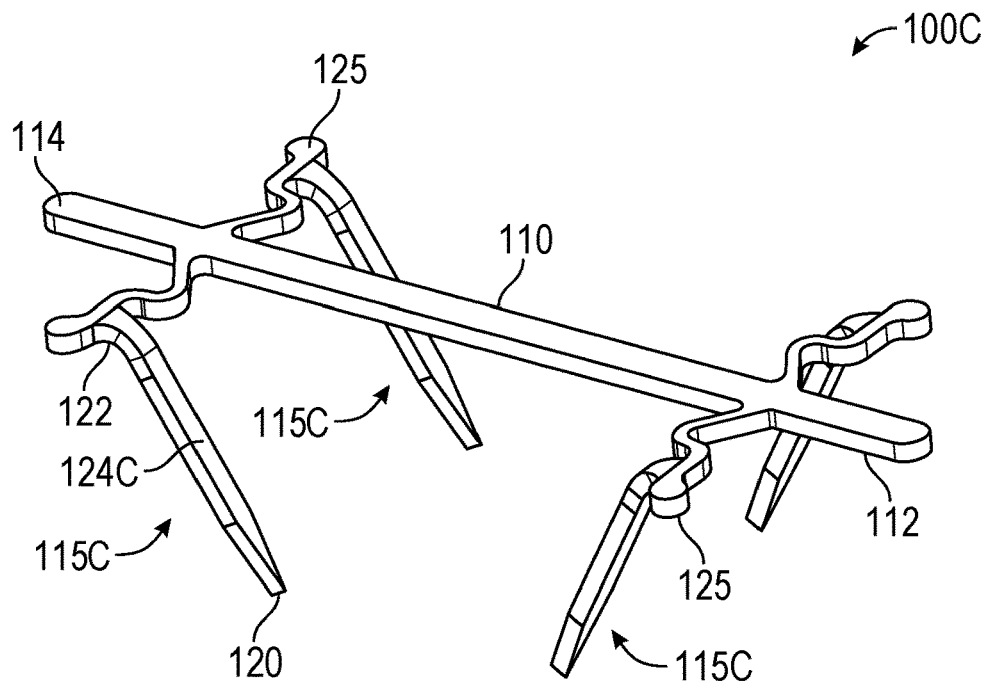

FIGS. 1A-1F are various views of a deep skin staple (100A, 100B, 100C) structure according to multiple embodiments of the present invention. These figures illustrate three different versions of a deep skin staple, 100A, 100B, and 100C, which can be collectively referred to as deep skin staple 100. The three illustrated versions include legs 115A, 115B, 115C with different width shovel portions 124A, 124B, 124C. While each of the embodiments illustrated includes a single common size shovel portion, the inventors anticipate deep skin staples that utilize multiple different sized shovel portions within a single device. FIG. 1A is an isometric view of the deep skin staple 100A with a wide leg 115A that includes a wide shovel portion 124A. FIG. 1B is an isometric view of the staple 100B with a medium leg 115B that includes a medium shovel portion 124B. Finally, FIG. 1C is an isometric view of the deep skin staple 100C with a narrow leg 115C that includes a narrow shovel portion 124C. The deep skin staples 100A, 100B, and 100C are representative of a range of leg widths envisioned but are not intended to be exhaustive. Deep skin staples with wider or narrower legs and shovel portions are within the scope of the inventions discussed herein. In these examples, the shovel portion 124A is 2 mm, the shovel portion 124B is 1.5 mm, and the shovel portion 124C is 0.5 mm. Legs 115 can include shovel portions in ranges from approximately 5 mm down to 0.25 mm.

Each of the deep skin staples 100 includes structures such as a bridge portion 110, a proximal extension 112, a distal extension 114, and legs 115 attached to the bridge portion 110 via spring arms 125. In an example, the deep skin staple 100A has wide legs 115A that include a wide shovel portion 124A that terminates in a pointed tip 120. In this example, the legs 115A also included an angled connection 122 that couples the leg 115A to the spring arm 125. The angled connection 122 includes a reduced cross-sectional area to allow for smaller holes at the skin surface as discussed above. The spring arm 125 is designed to provide for force modulation by allowing for flex between the bridge portion 110 and each leg 115A individually to allow independent movements of the legs with reduced effect on other nearby legs, but at the same time provide enough tension to keep a wound closed.

Figure 1D:
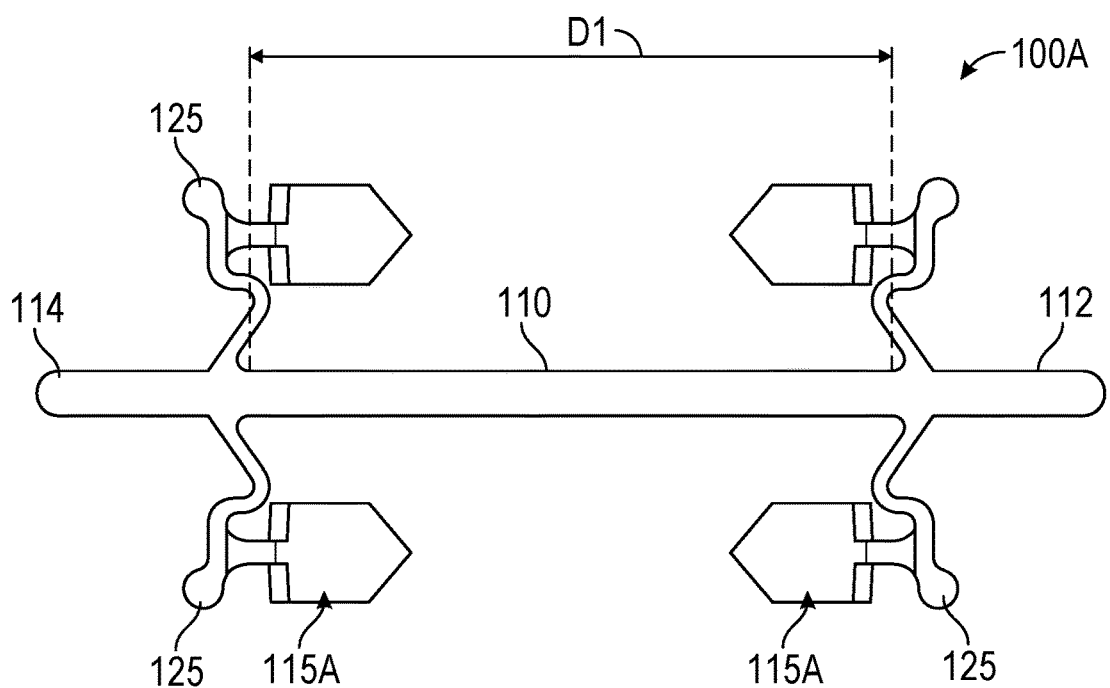
Figure 1E:
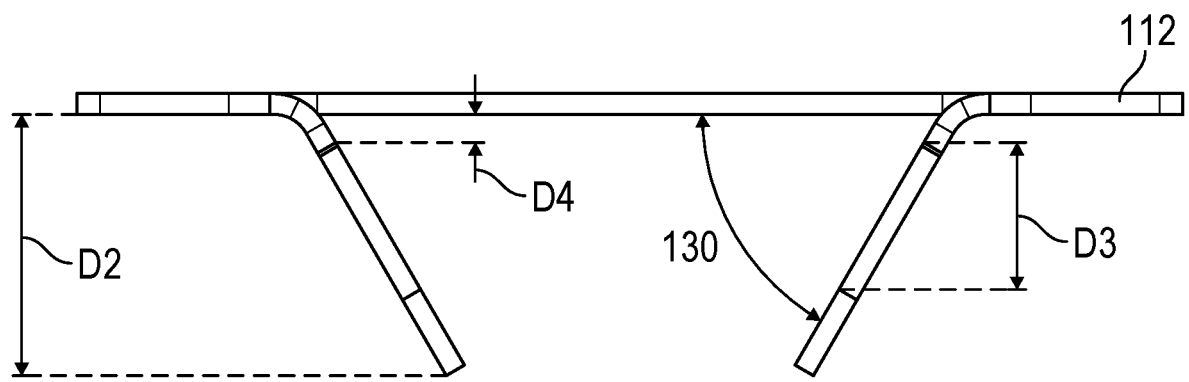
Figure 1F:
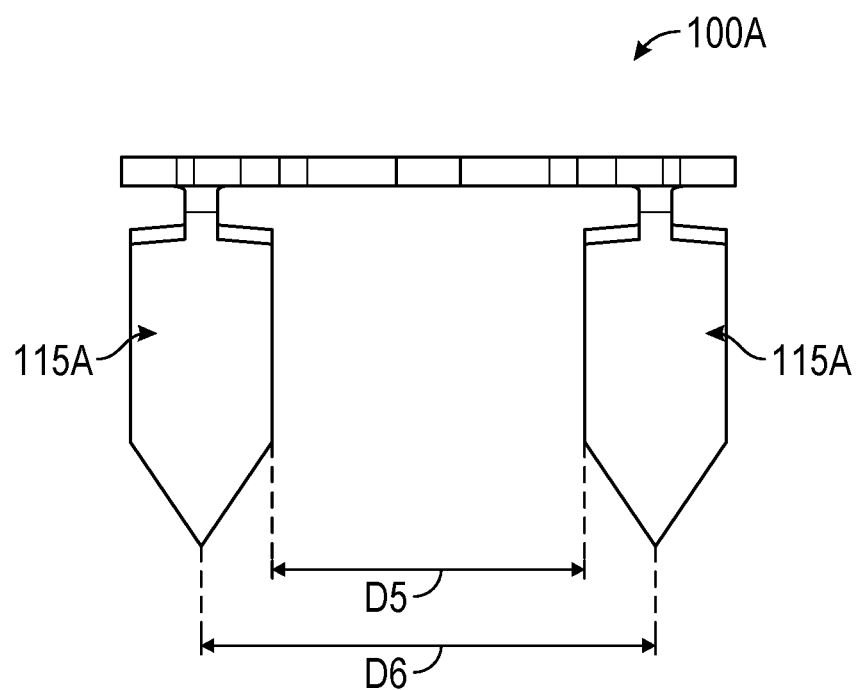

FIGS. 1D-1F include a number of distance references to illustrate different distances that can be adjusted for any particular deep skin staple. D1 is the arm spread distance, which is the distance between sets of spring arms 125 across bridge portion 110. In an example, distance D1 can be in a range between 5 mm to 20 mm, with 12.9 mm being an example length. The distance D1 controls how far apart opposing sets of legs 115 are in a particular deep skin staple design. D2 is the vertical staple depth, which can range from 1 mm to 10 mm, with 5.1 mm being an example length illustrated in FIGS. 1A-1F. Note, the vertical staple depth, D2, is impacted by the actual length of leg 115 and the leg angle 130, which is 60 degrees in these examples. D3 is the shovel vertical depth which can range from 1 mm to 6 mm and is impacted by the length of the shovel portion 124 and the leg angle 130. D4 is the connection depth which is reflective of the depth into the skin the reduced cross-section angled connection 122 extends. In this example D4 is approximately 0.5 mm. D5 is the shovel spacing distance (spacing between the closest edges of two shovels) which varies based on the length and configuration of the spring arms 125 connecting the legs 115 to the bridge portion 110. In this example, D5 is approximately 4.4 mm, but can vary between 1 mm and 10 mm. D6 is the tip spacing distance which varies based on a combination of D5 and shovel portion 124 width. In this example, D6 measures approximately 6.4 mm and can range between 1 mm and 10 mm. As noted below, the spacings D5 and D6 discussed here are applicable to all variations of the deep skin staples discussed herein.

In another example, the spacing of D6 can be increased to splay the staple legs 115 outward laterally. As D6 increases, without a similar increase is the lateral distance between the connection point of the staple leg 115 to spring arm 125, the tips 120 of each staple leg 115 are directed outward (splayed outward). A benefit of splaying the staple legs 115 outward can include better retention of the deep skin staple within the skin. In the illustrate example, the tip spacing D6 can be increased to 8 mm to 12 mm (or greater) to create a set of splayed staple legs 115. The concept of staple leg splay is further illustrated and discussed in reference to FIGS. 9A-10C.

FIG. 1D is a top view of deep skin staple 100A and illustrates the opposing legs 115A that are each coupled to the bridge portion 110 via spring arms 125. FIG. 1E is a side view of deep skin staple 100A and illustrates the leg angle 130 of the opposing legs 115A. In this example, the leg angle 130 is set at 60 degrees, other angles are contemplated such as 45 degrees shown in FIG. 2C. Finally, FIG. 1F is an end view of deep skin staple 100A and illustrates spacing between adjacent legs 115A. FIGS. 1E and 1F also illustrate the planar nature of the bridge portion 110, proximal extension, 112, distal extension 114, and spring arms 125.

Figure 2A:
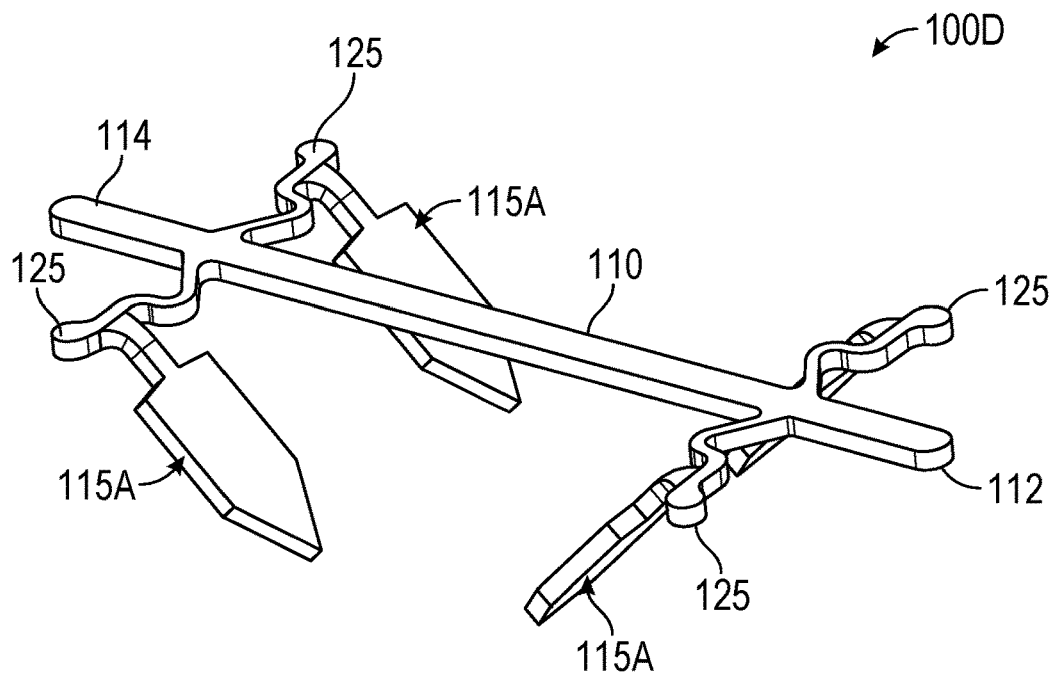
FIGS. 2A-2D are various views of a deep skin staple according to one embodiment of the present invention.
Figure 2B:
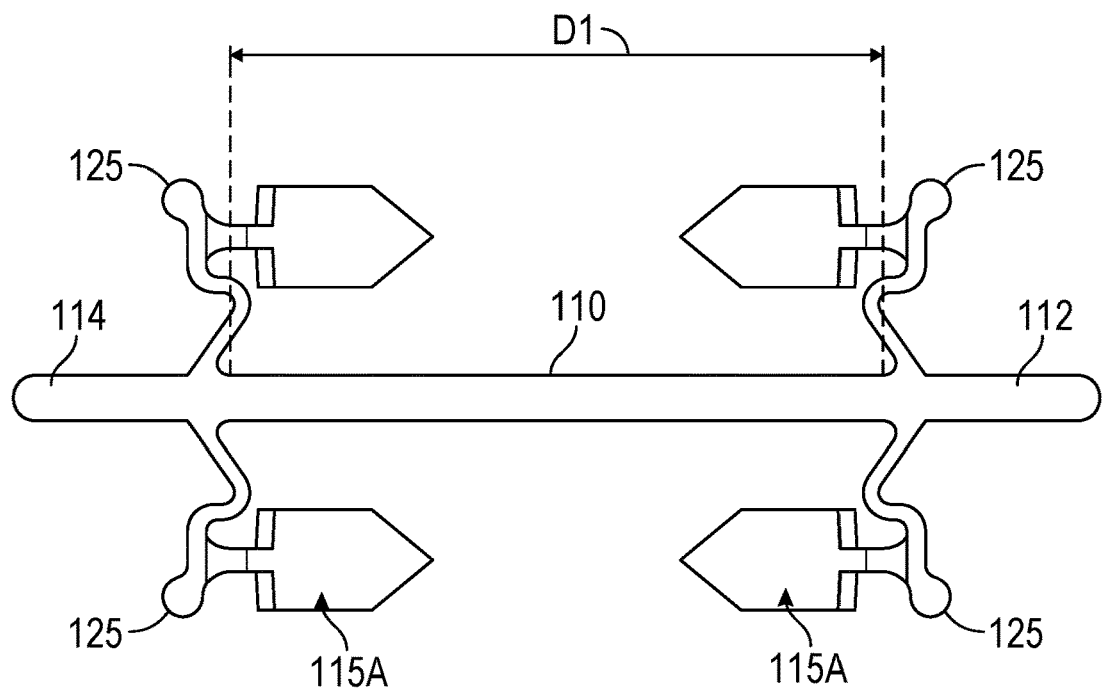
Figure 2C:
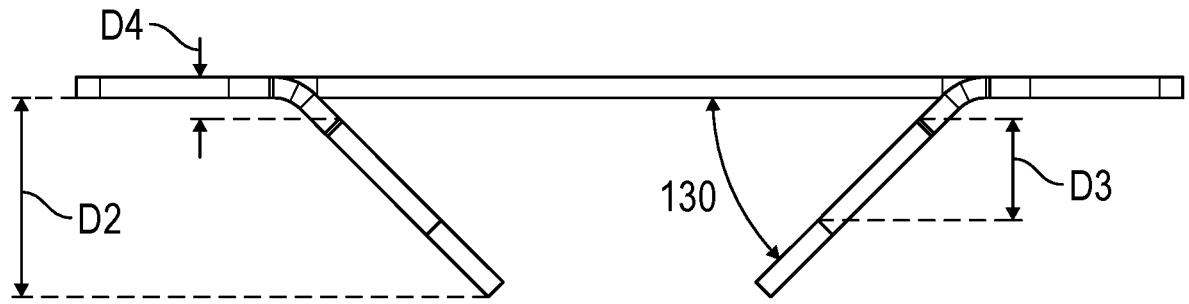
Figure 2D:
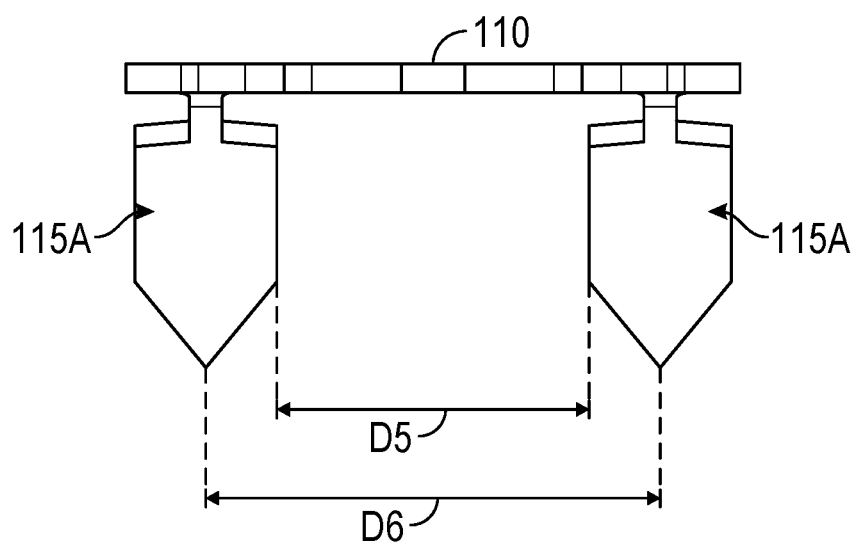

FIGS. 2A-2D are various views of a deep skin staple 100D according to one embodiment of the present invention. In this example, the deep skin staple 100D includes a bridge portion 110 and wide legs 115A coupled via spring arms 125 to the bridge portion 110. In these examples, the bridge portion 110 is does not include any spring characteristics and is designed to be a fixed solid connection between the opposing legs 115A with the spring arms 125 providing the force modulating spring characteristics. The spring arms 125 allow for individual legs in an array of legs on a deep skin staple to provide modulation for each leg individually. The spring arms 125 operate to allow independent and isolated movements of individual legs within the same array of legs on a deep skin staple, and not to reference force modulation to the bridge, as the bridge is not fixed at a location. From a force perspective, the bridge is for the purpose of maintaining tension to close a wound, while movements of individual legs relative to each other create the force modulation because of the existence of the spring arms. FIG. 2A is an isometric view of a four-legged deep skin staple 100D. The deep skin staple 100D includes four wide legs 115A positioned on either side of the bridge portion 110. FIG. 2B is a top view of the deep skin staple 100D, which clearly illustrates the arrangement of the four wide legs 115A. As shown, the spring arms 125 extend roughly perpendicular from the bridge portion 110 just inside of the proximal extension 112 and distal extension 114. In this example, the spring arms 125 include an initial angled section that angle towards the middle of the bridge portion 110. The spring arms 125 also include a curved portion roughly in the shape of an 'S' that connects the angled portion to the straight extension portion where the angled connection of the wide leg 115A connects to the spring arm 125. FIGS. 2C and 2D are side and end views of deep skin staple 100D that illustrate the different distances (D1, D2, D3, D4, D5 and D6) discussed above. One of the differences with the deep skin staple 100D is the leg angle 130, which is approximately 45 degrees in this example.

FIGS. 3A-3D are various views of a deep skin staple 300 structure according to one embodiment of the present invention. In this example, the deep skin staple 300 includes an additional set of opposing legs 315 that are attached via outer connections 316. On one side of the deep skin staple 300, the leg 315 is coupled to the proximal extension 312 via an outer connection 316. While an opposing leg 315 is coupled to the distal extension 314 via another outer connection 316. The outer connections 316 are bent extensions of the proximal extension 312 or distal extension 314. In this example, each leg 315 includes a tip 320 and a shovel portion 324. The shovel portion 324, in this example, is similar to the wide shovel 124B discussed above. Each of the middle legs 315 are coupled to a spring arm 325 via an angled connection 322. In this example, either the angled connection 322 or the outer connection 316 determines the angle of the respective leg 315 with respect to the longitudinal axis running through the spring bridge 310 from the proximal extension 112 to the distal extension 114. The legs in this example are at leg angle 330, which is illustrated as being 60 degrees but can vary between 20 degrees and 90 degrees. Preferably, the leg angle 330 is varied between 20 degrees and 89 degrees, as the inventors have found a benefit in the legs not being perpendicular to the wound.

The deep skin staple 300 also integrates another concept that can be include in any of the deep skin staples discussed herein, which is a spring bridge 310. The spring bridge 310 is illustrated in the form of a circular portion in the center of the bridge portion of the deep skin staple 300. Other structures with spring characteristics could also be used in place of the circular structure shown, such as an oval, an S-shape, a Z-shape, a W-shape, a diamond shape, or a box shape. The circular shape of spring bridge 310 is intended to cover circular and oval shaped structures. The spring bridge 310 provides additional force modulation characteristics to the overall deep skin staple 300 as well as providing spring characteristics to the opposing legs 315 extending from the proximal extension 312 and the distal extension 314. The outer connections 316 also can provide some amount of spring characteristics due to flex in the bent structure.

Figure 3A:
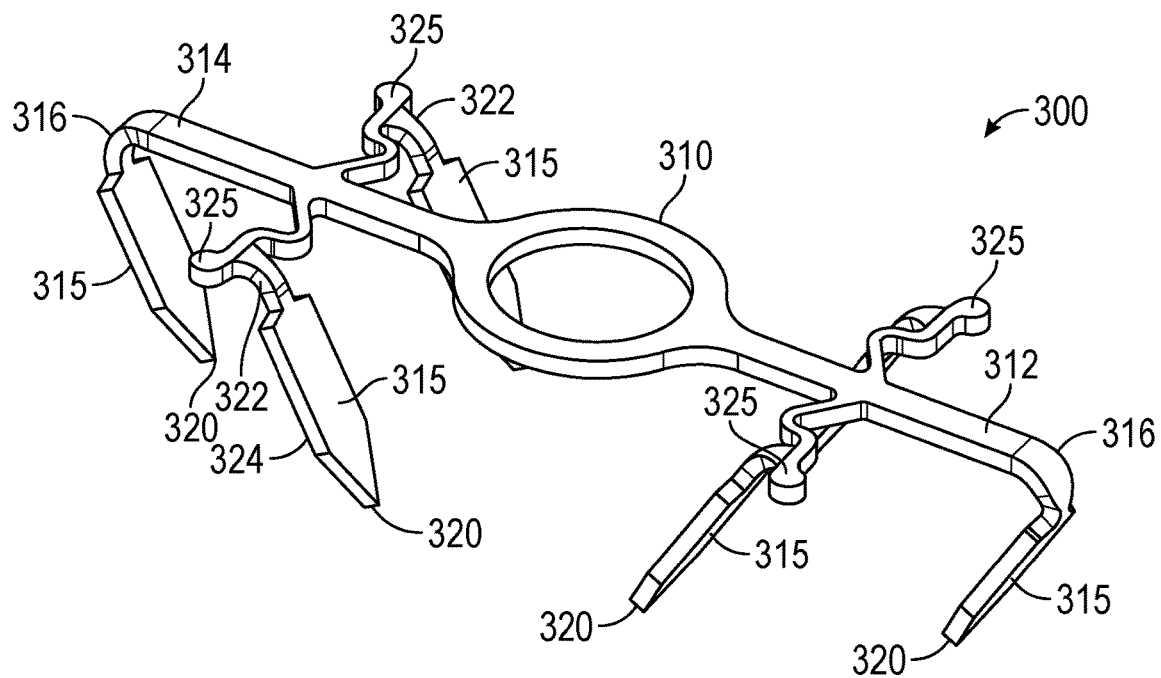
FIGS. 3A-3D are various views of a deep skin staple structure according to one embodiment of the present invention.
Figure 3B:
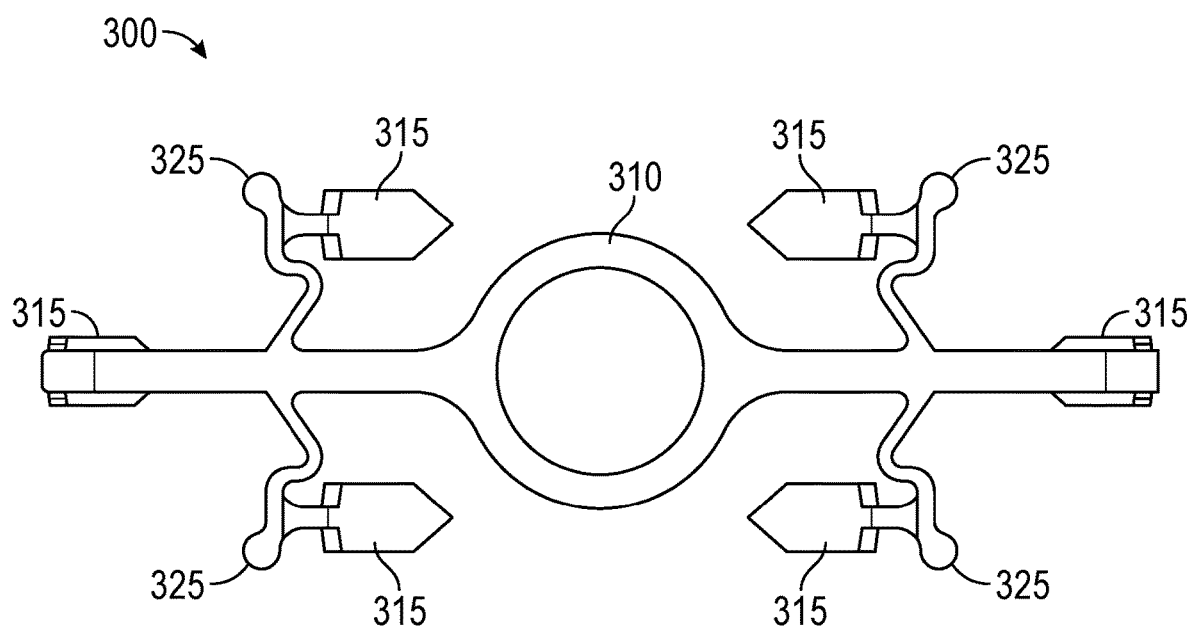

FIG. 3B is a top view of deep skin staple 300 that provides additional illustration of features such as the spring bridge 310 and the six opposing legs 315. The six legs 315 are arranged with three on each side of the spring bridge 310. The legs include two opposing sets of legs 315 coupled to the spring bridge 310 via spring arms 325. The opposing sets of legs 315 include one leg 315 on each side of the spring bridge 310. The structure of the middle portion of the deep skin staple 300 is similar to the previously discussed deep skin staples with the introduction of the circular spring structure in the center of the bridge portion.

Figure 3C:
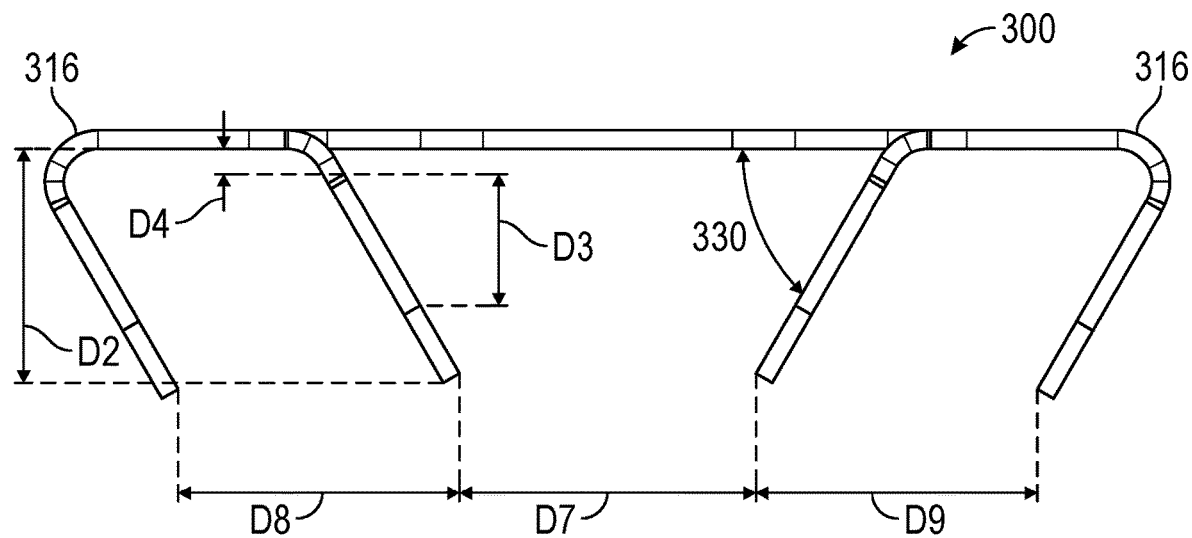
Figure 3D:
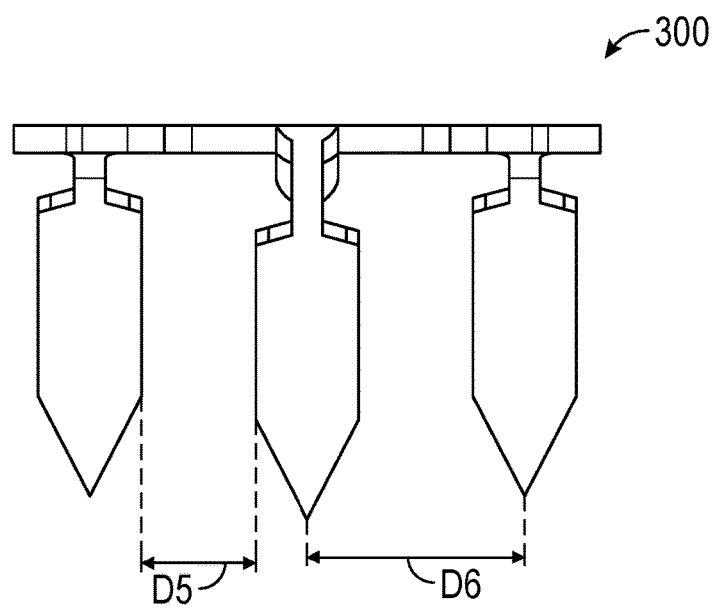

FIG. 3C is a side view of the deep skin staple 300 that illustrates the angles of the legs 315, as well as the outer connections 316 on either end of the deep skin staple 300. Distances D7, D8, and D9 measure the different longitudinal tip to tip distances between various legs 315. D7 measures the distance between the middle opposing sets of legs 315. In this example, D7 is approximately 6.4 mm and can vary from 1 mm to 10 mm. D8 and D9 measure the distance from one of the middle sets of legs 315 to the outer leg 315 on each end. In this example, D8 and D9 are approximately 6.1 mm and can vary from 2 mm to 20 mm. While D8 and D9 are illustrated as being equal distances, D8 and D9 can be different with one side of the deep skin staple 300 being longer in such a configuration. FIG. 3D is an end view of deep skin staple 300 that illustrates the arrangement and spacing of the legs 315. In this example, D5 is the leg to leg spacing along the plane of the diagram and D6 is the tip to tip spacing along the plane of the diagram The spring incorporated into the bridge enhances the elasticity and flexibility of the device in all directions. It can either be the only spring in the staple or be combined with other springs in the device (e.g., FIGS. 3A-3D). Each spring allows independent and isolated movements of the staple relative other staples in the same array while the connected bridge allowing tension to sustain on keeping the wound closed.

Figure 8C:
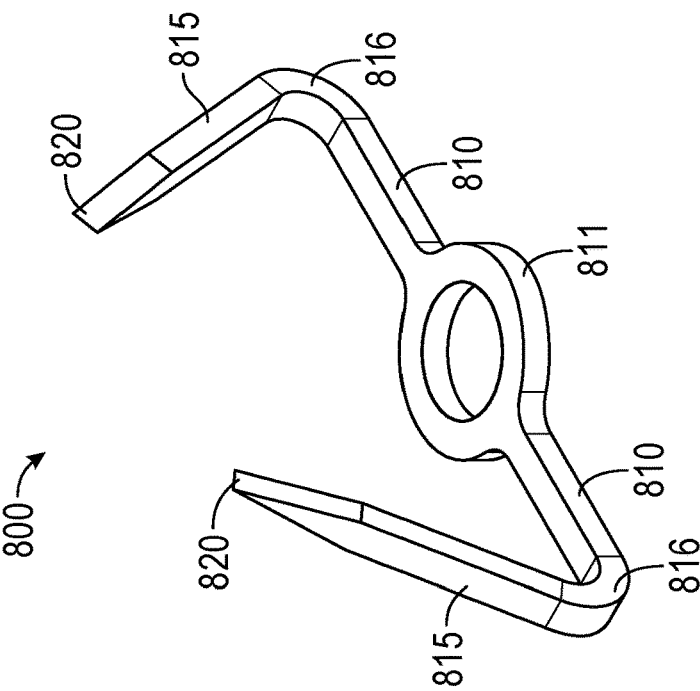
FIGS. 8A-8C are various views of a deep skin staple structure according to one embodiment of the present invention.
Figure 8B:
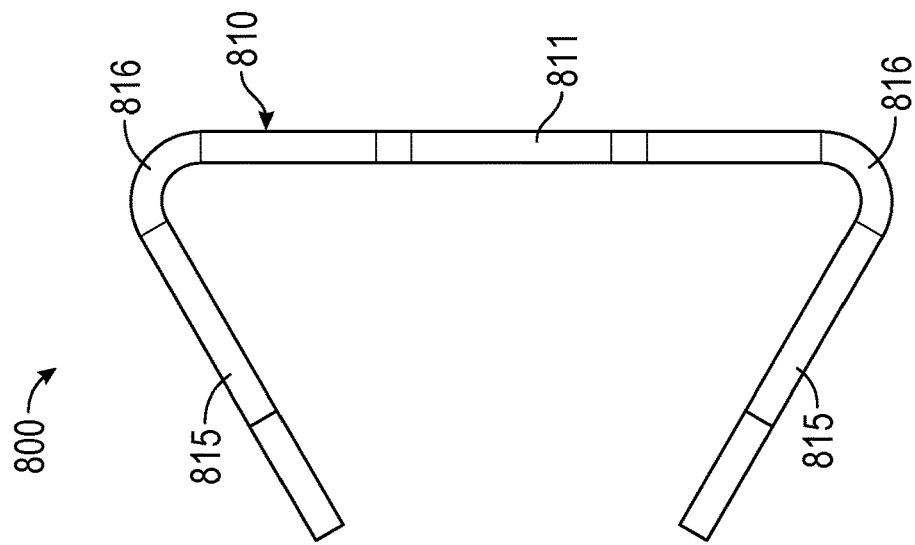
Figure 8A:
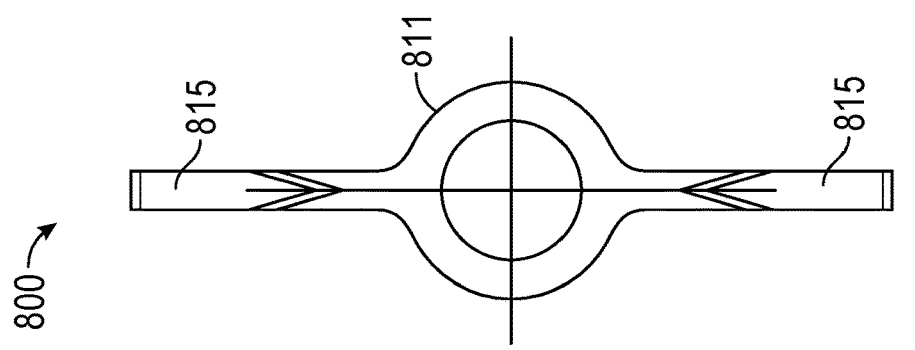

The example illustrated in FIGS. 3A-3D can be modified to eliminate spring arms 325 and the connected staple legs 315, which would leave just the spring bridge 310 with opposing sets of staple legs 315 extending from the proximal extension 312 and the distal extension 314. The remaining two staple legs couple to the proximal extension 312 and distal extension 314 via outer connections 316. The resulting deep skin staple would include only two opposing staple legs on outer ends of the device. FIGS. 8A-8C, discussed below, illustrate an example of a deep skin staple with only two opposing staple legs couple to proximal and distal ends of a spring bridge structure.

Figure 4A:
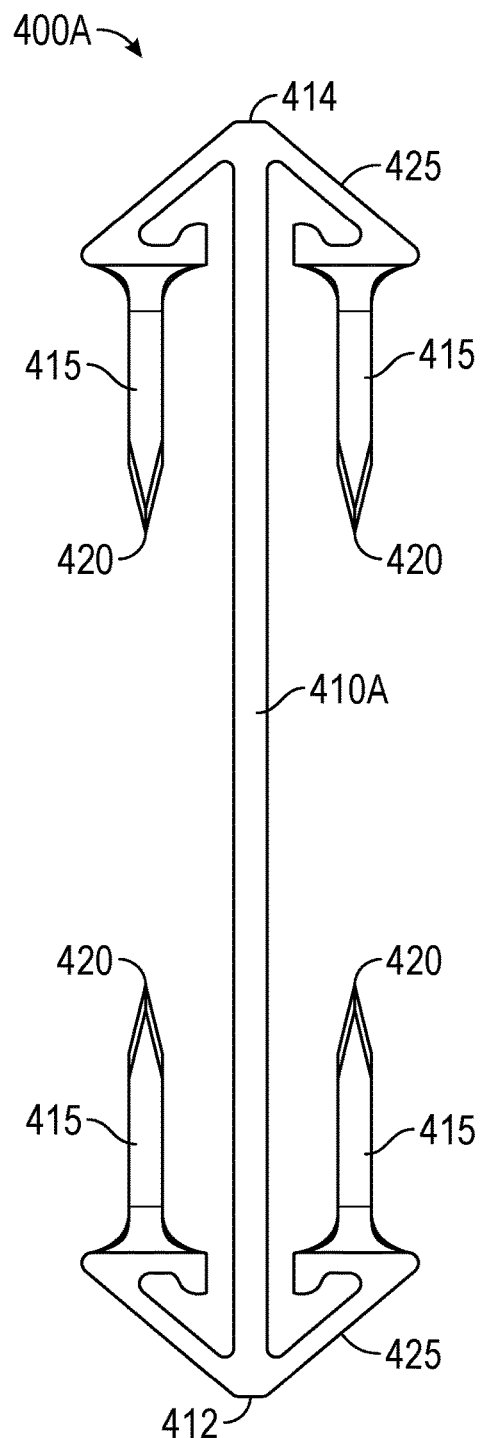
Figure 4B:
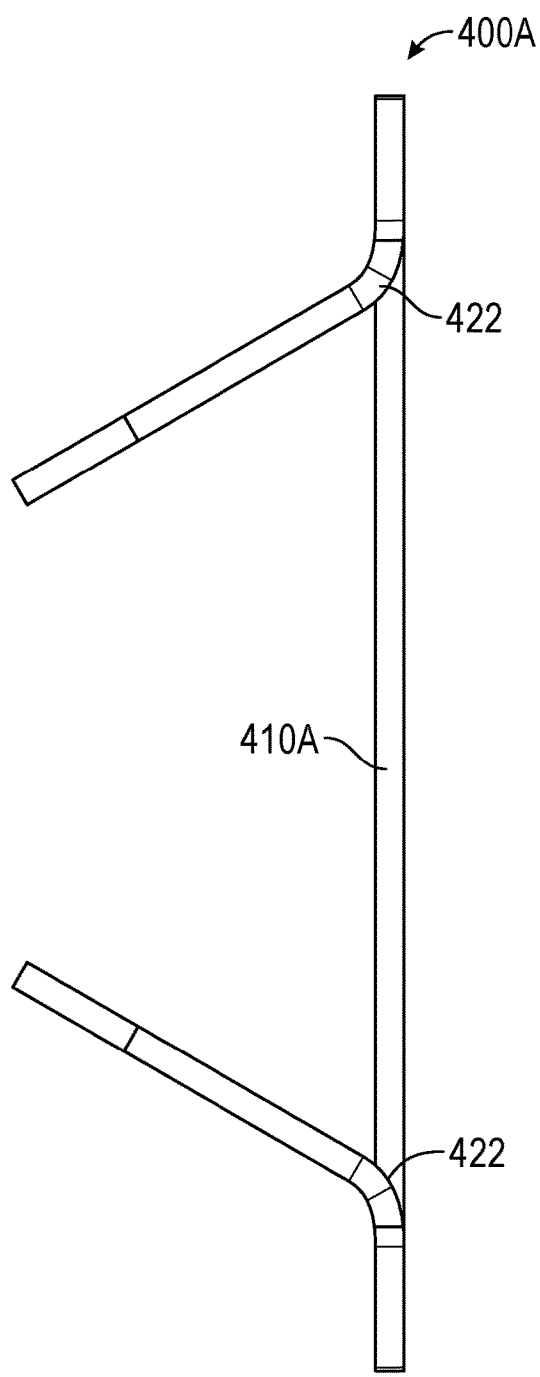
Figure 4C:
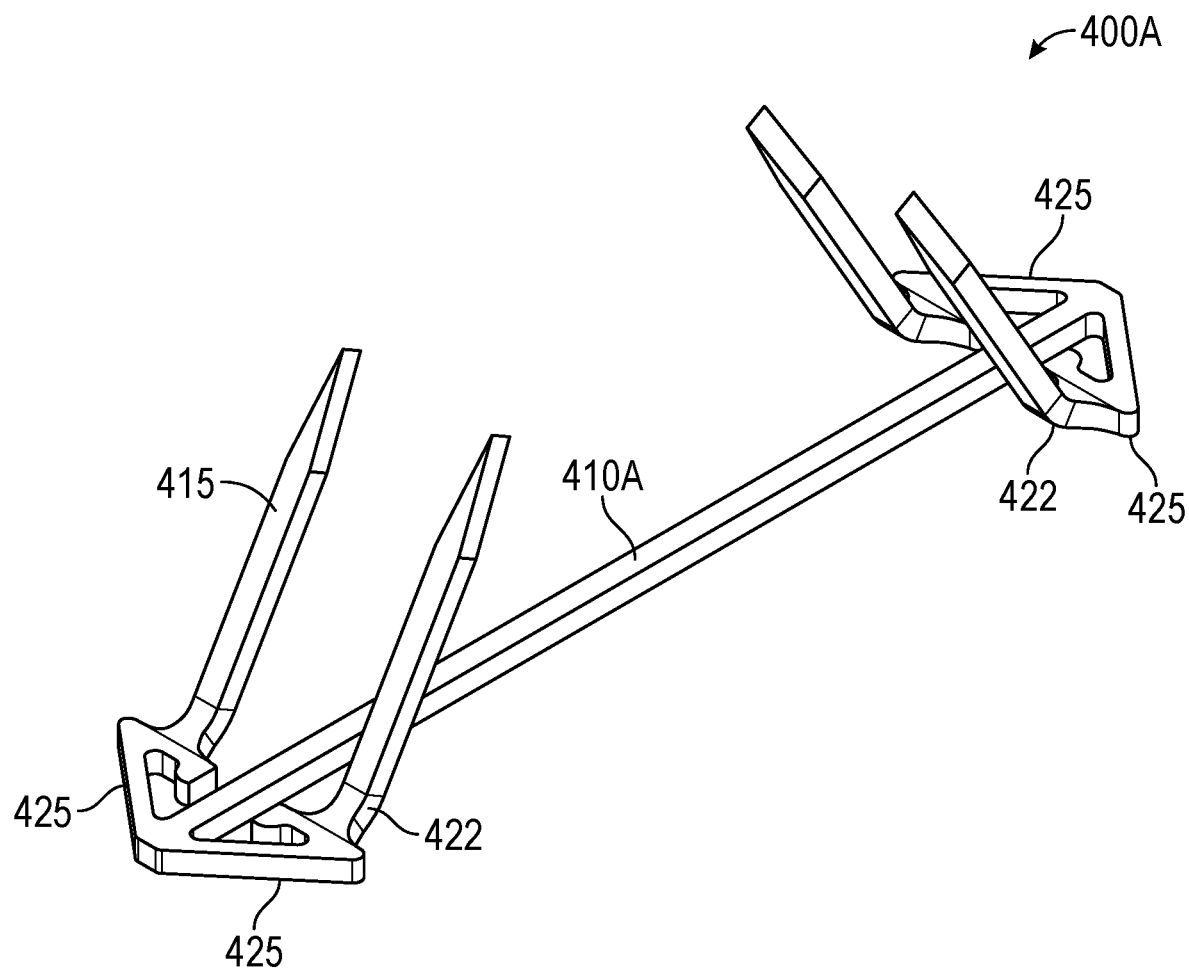
Figure 4F:
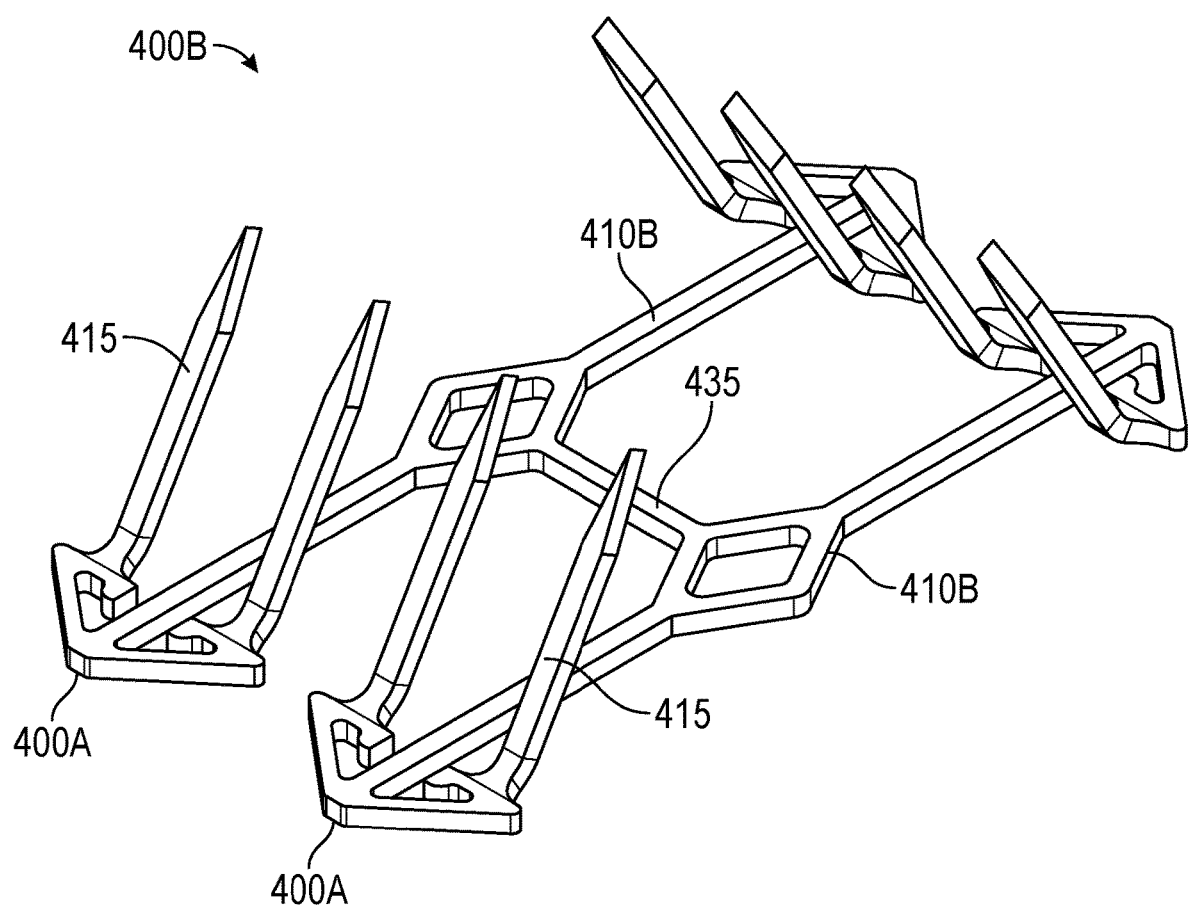
Figure 4H:
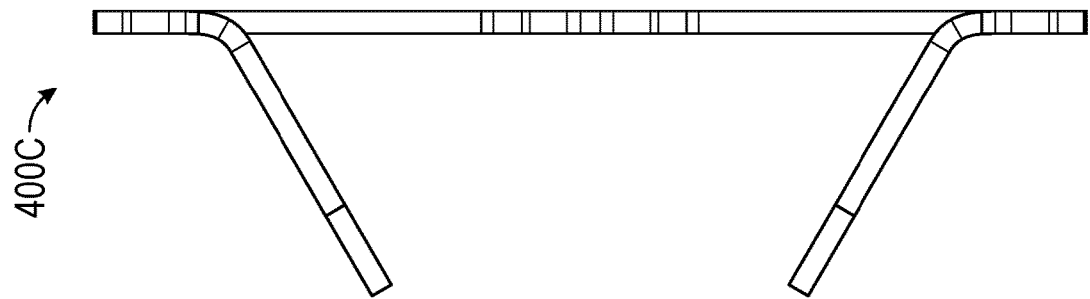
Figure 4G:
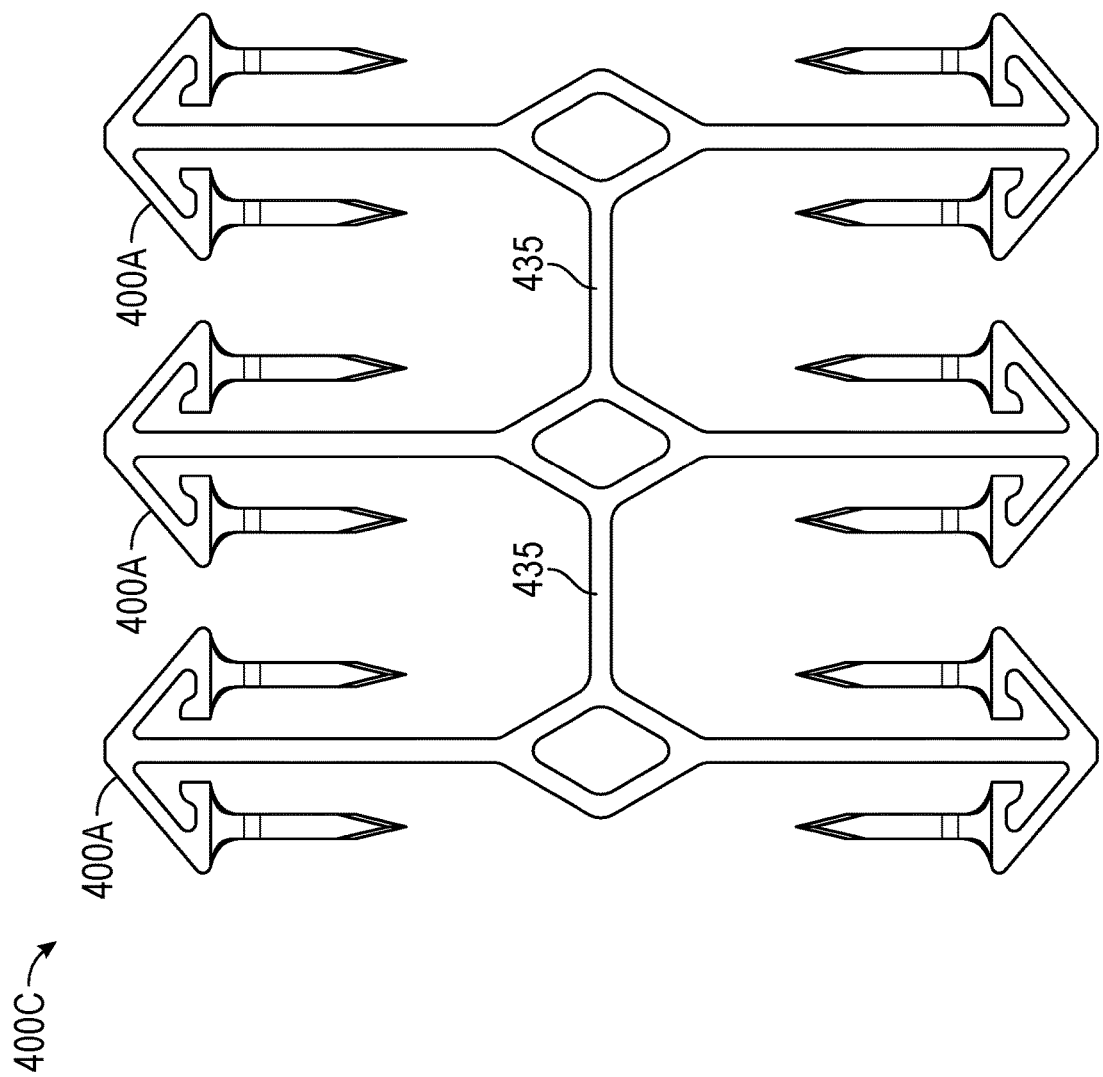
Figure 4I:
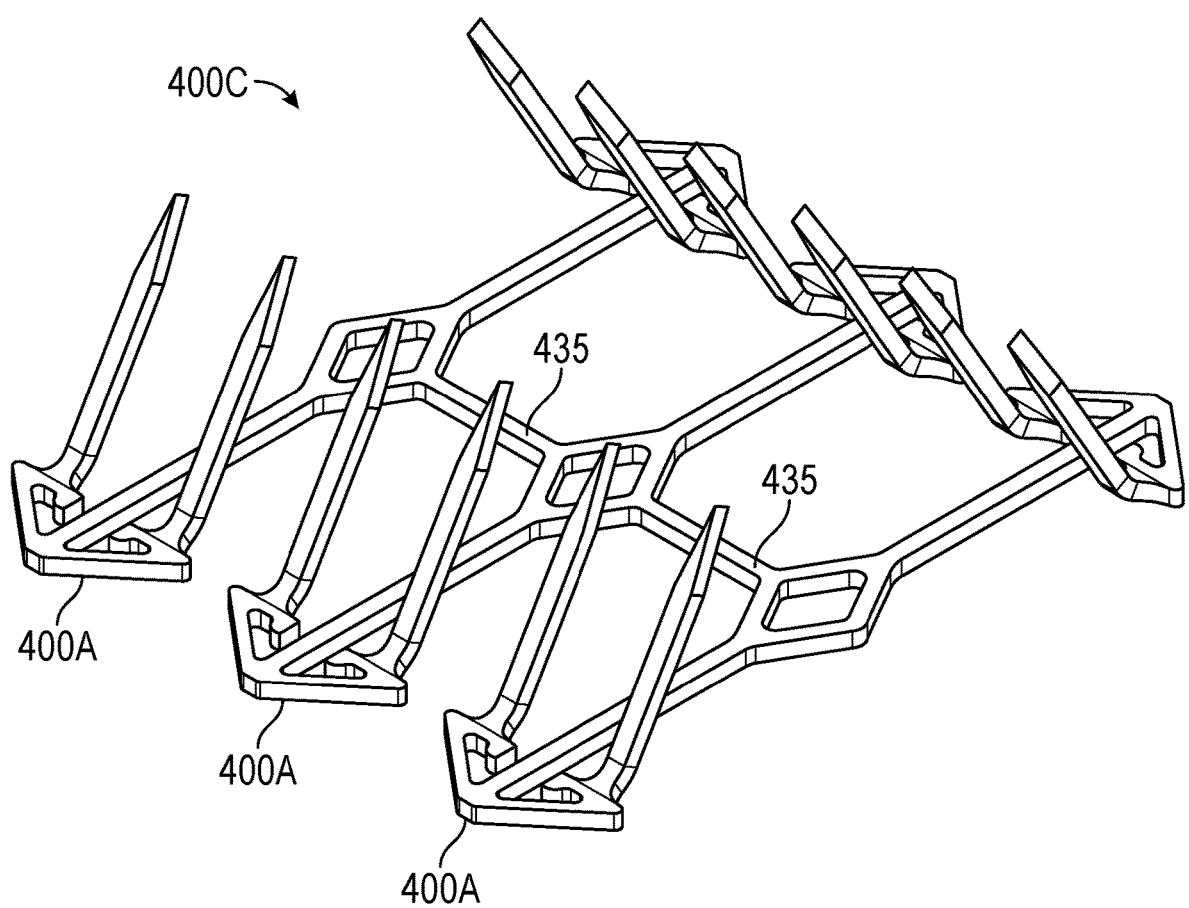

FIGS. 4A-4I are various views of a deep skin staple (400A, 400B, 400C) structure according to multiple embodiments of the present invention. These figures illustrate three different versions of a deep skin staple, 400A, 400B, and 400C, which can collectively be referred to as deep skin staple 400. FIGS. 4A-4C illustrate a single deep skin staple structure 400A with a solid bridge portion 410A. FIGS. 4D-4F illustrate two single deep skin staple structures 400A coupled together with a connector portion 435. The deep skin staple 400B also includes bridge portions 410B that include a spring structure, similar to those discussed above in reference to FIGS. 3A-3D (but in a diamond configuration versus the round (circular or oval shaped) spring structure discussed above). FIGS. 4G-4I illustrate deep skin staple 400C, which is three single deep skin staple structures 400A coupled together by multiple connector portions 435. In this example, each deep skin staple 400A includes a spring bridge portion 410B that has a diamond spring structure in the middle between the opposing staple legs 415.

Returning to FIGS. 4A-4C, the deep skin staple 400A includes a bridge portion 410A running through a longitudinal axis of the device from a proximal end 412 to a distal end 414 (which are essentially arbitrary as the device is symmetrical along an axis transverse to the longitudinal axis). On each end of the deep skin staple 400A are a pair of opposing spring arms 425 that each couple a staple leg 415 to the bridge portion 410A. The staple legs 415 bend outward at angled connection 422 from a device plane defined by the bridge portion 410A and the spring arms 425.

The angled connection 422 can form an angle of between 45 and 60 degrees from the device plane. In certain examples, the angled connection 422 can vary from 30 degrees to 89 degrees. In the illustrated example, the angled connection 422 forms a 60-degree angle for the staple legs 415. Each staple leg 415 terminates in a pointed tip 420. In this example, the pointed tip 420 is chiseled, but other skin penetration shapes can be implemented. Distances between staple legs 415 can be similar to those discussed above in reference to deep skin staples 100A, 100B, and 100C. In this example, the spring arms 425 and the angled staple legs 415 cooperate to provide spring characteristics that are able to modulate mechanical force and off load tension at the reticular layer of the skin. The staple legs 415 are sized to extend into the reticular layer of skin and function in conjunction with the spring arms 425 to modulate forces on the wound from the skin surface down into the reticular layer of the skin.

In this example, each spring arm 425 extends from a proximal or distal end of the bridge portion 410A. Each spring arm 425 extends in a roughly 45 degree angle towards a central portion of the deep skin staple 400A, the angle can vary between 20 degrees to 80 degrees as measured from an axis transverse to the longitudinal axis running the length of the bridge portion 410A. The spring arm 425 further includes a leg portion that runs along the traverse axis and couples to the angled connection 422 to the staple leg 415. The shape of the spring arm 425 can be described as an open triangle with hypotenuse of the open triangle coupled to the bridge portion and the other side of the open triangle coupled to the staple leg 415 via the angled connection 422. The deep skin staple 400A includes opposing open triangle spring arms affixed to each of the proximal end and the distal end, which support two opposing staple legs 415 on each end.

FIGS. 4D-4F illustrate deep skin staple 400B, which can also be considered a staple array (e.g., an array of deep skin staples 400A with a modified bridge portion 410B). In these examples, the deep skin staple 400B can include two deep skin staples 400A coupled together with a connector portion 435. The deep skin staple 400B also adds a spring bridge portion 410B to the deep skin staple 400A. In another example, an array of deep skin staples 400A can be similarly created that does not include the spring bridge portion, but rather retains the solid bridge portion 410A. The spring bridge portion 410B in these examples includes a diamond shaped spring structure and the connector portion 435 couples between two opposing corners of the diamond spring structure. The deep skin staple 400A includes spring arms 425 that couple the staple legs 415 to the spring bridge portion 410B. Each spring arm 425 provides for force modulation within each staple leg 415. The diamond spring structure forming the spring bridge portion 410B can provide additional force modulation across the length of the device. In this example, the spring bridge portion 410B adds to the force modulation characteristics discussed above of the spring arms 425 and staple legs 415. The angle of the staple legs 415 is selected to direct additional wound closing forces down into the reticular layer of the skin where the tissue is denser and requires more force to close wounds.

FIGS. 4G-4I illustrate deep skin staple 400C, which can also be considered a three-staple array (e.g., an array of three deep skin staples 400A with spring bridge portions 410B (as illustrated in FIGS. 4D-4F)). The deep skin staple 400C includes three deep skin staples (similar to deep skin staple 400A) coupled together via connector portions 435 that extend from corners of the diamond spring structure in the center of the bridge portions (spring bridge 410B). The diamond spring structure within bridge portion 410B is the primary difference in the deep skin staple as compared with deep skin staple 400A, as the reminder of the structure is the same. The deep skin staple arrays 400B, 400C also differ from deep skin staple 400A in the addition of the connector portions 435, which are in this example solid material connectors similar to the solid bridge portions. In certain examples, the deep skin staple arrays 400B, 400C can be delivered affixed to a backing materials and exclude the connector portions 435.

Figure 5A:
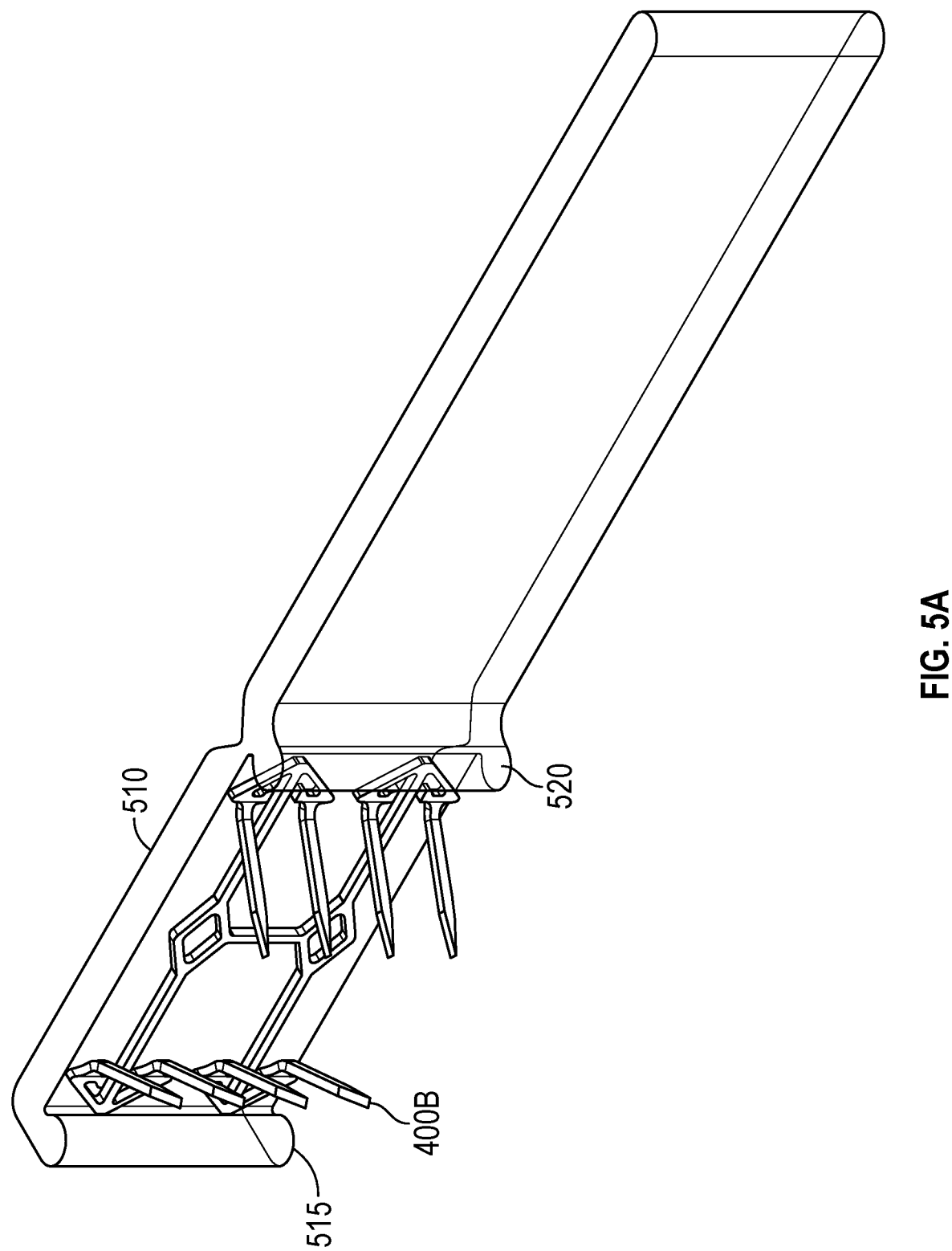
Figure 6:
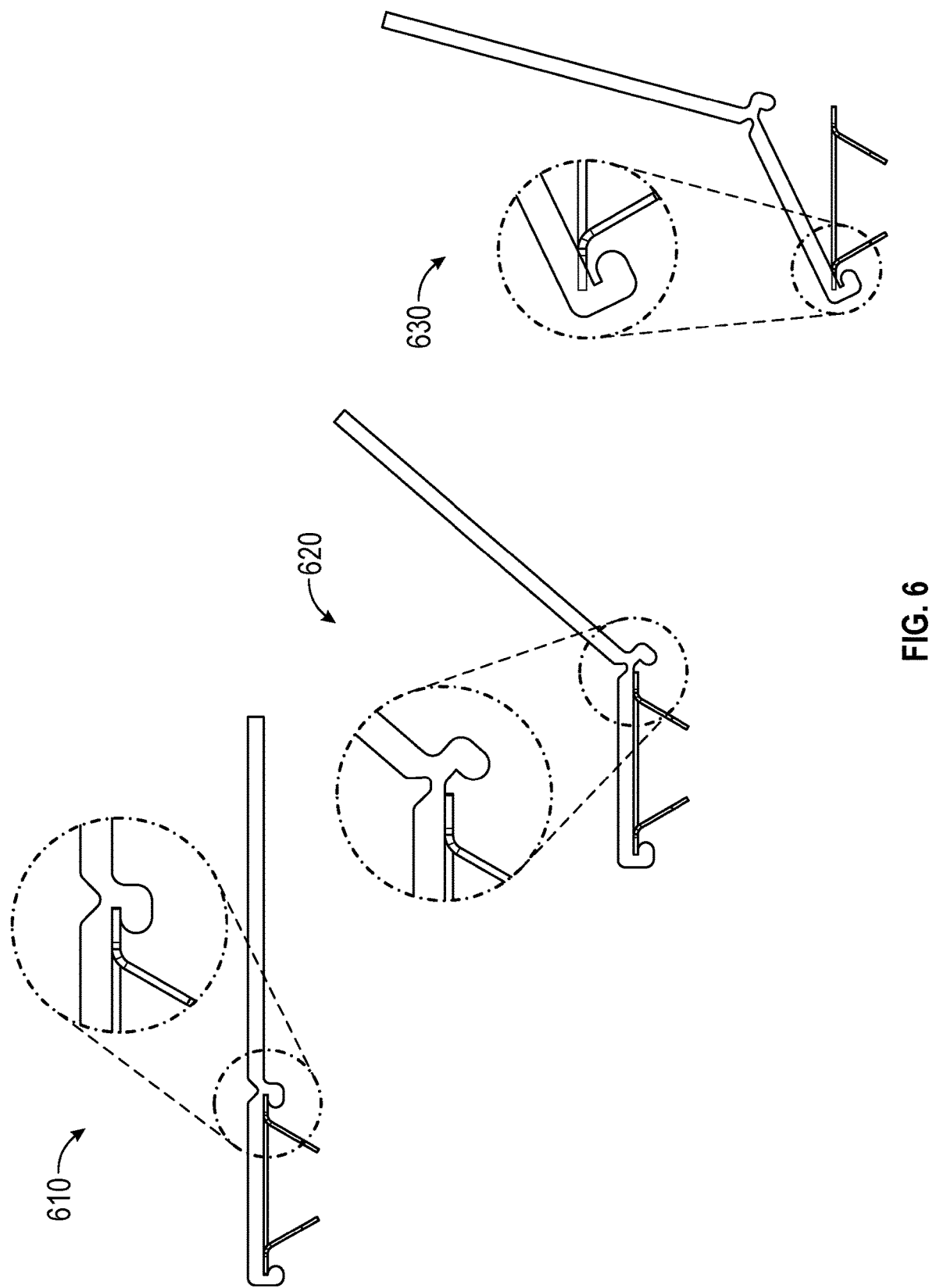
FIG. 6 is an illustration of an application technique using the application instrument according to one embodiment of the present invention.

FIGS. 5A-5D are various views of a deep skin staple application instrument 510 according to one embodiment of the present invention. In this example, a deep skin staple 400B is held by opposing staple wedges 515 and 520. The staple wedges 515, 520 hold the distal and proximal ends of the deep skin staple within the application instrument 510. As shown in detail in FIGS. 5C and 5D, each of the staple wedges 515, 520 include recesses 525, 535 that capture the deep skin staple to assist in applying the deep skin staple to a wound (as illustrated in FIG. 6). In this example, the staple wedges 515, 520 include a semi-circular protrusion that forms recesses 525 and 535. Recesses 525 and 535 are rounded pockets sized to receive proximal and distal ends of a deep skin staple. As illustrated in FIG. 5B, the application instrument 510 also includes a handle 540 that is used to assist in application. A portion of the application technique involves pivoting the handle 540 at the notch 530, which facilitates release of the deep skin staple from the application instrument 510.

In an example, the application instrument 510 can be a clear plastic structure that assists in visualizing the wound during application of the deep skin staple. In other examples, the application instrument 510 can be made from a solid rubber material or a foam rubber material. The rubber material may be selected from materials such as Aflas, Buna-N, Vinyl Rubber, Butyl, EPDM, Flourosilicone, Silicone, Kalrez, Natural Rubber, Neoprene, Polyurethane, Santoprene, SBR, or Viton Fluoroelastomer, among others. The application instrument 510 may be molded, casted, machined, or extruded. A tension indicator can also be included along the superior surface (surface opposite the deep skin staple) that can provide an indication of tension applied to the deep skin staple during application. In an example, the tension indicator is printed on the superior surface. The application instrument 510 can be provided in widths that match the deep skin staple or deep skin staple array.

FIG. 6 is an illustration of an application technique using the application instrument according to one embodiment of the present invention. The illustrated application technique includes three illustrated operations: application 610, pivot 620, and release 630. The application process using application instrument 510 can begin at operation 610 with application of the deep skin staple. During application the deep skin staple is held within the application instruction 510 by the staple wedges 515, 520. Application of the deep skin staple can include pressing a distal end of the deep skin staple into skin on a first side of the wound. Then the application instrument 510 is used to pull the deep skin staple across the wound (which will also operate to close the wound) and completed by pressing the proximal side of the deep skin staple in a second side of the wound. Pressing the proximal side of the deep skin staple is performed immediately distal of the notch 530. Once the deep skin staple is applied across the wound (and the wound is closed), removal of the application instrument 510 can begin with pivoting of the handle 540 about the notch 530 to release the proximal side of the deep skin staple. Finally, the application technique using the application instrument 510 can complete with rotation of the distal end away from the distal end of the deep skin staple (as shown in operation 630).

Figure 7:
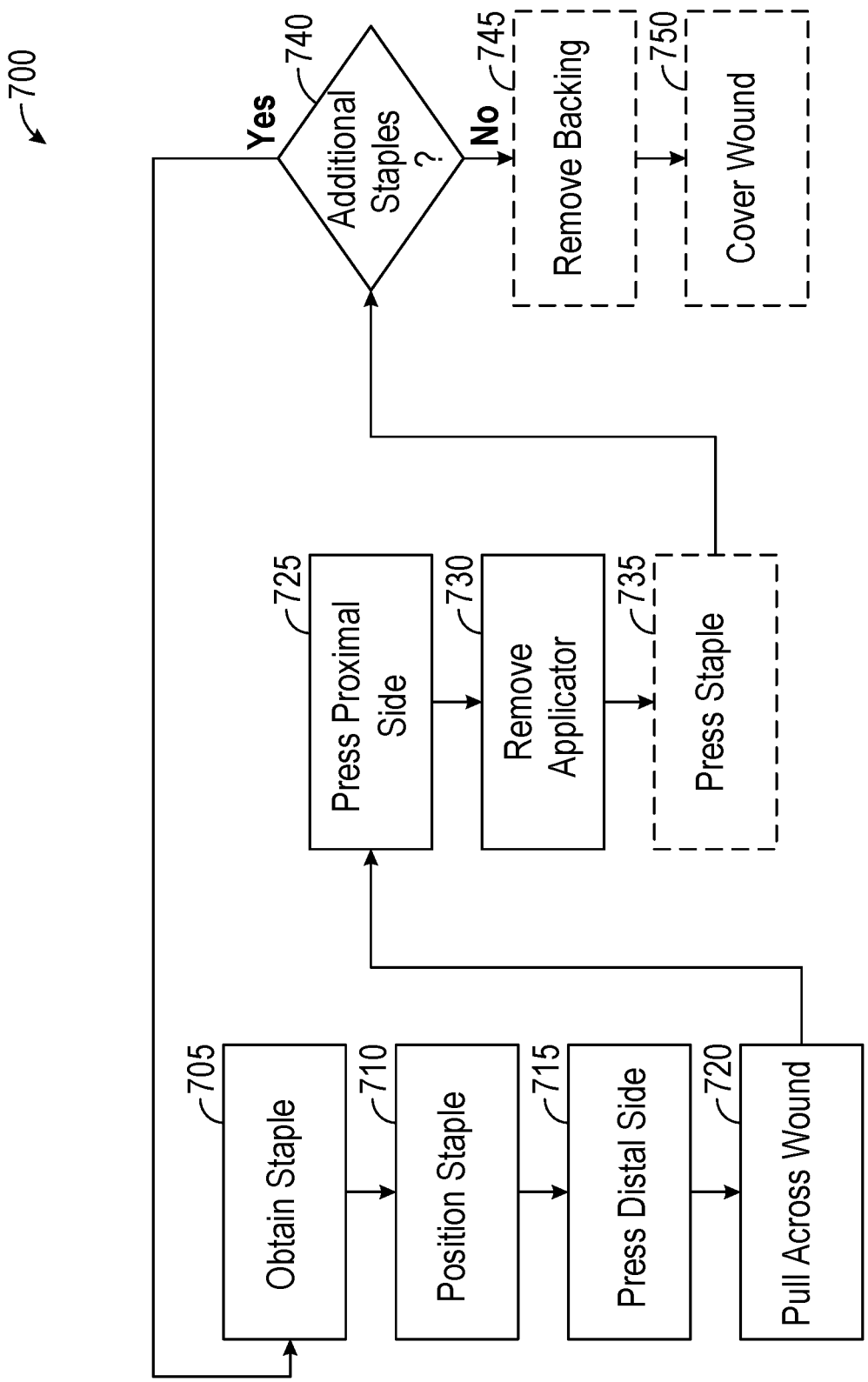
FIG. 7 is a flowchart illustrating an application technique for applying one of the disclosed deep skin staples in accordance with an embodiment of the present invention.

FIG. 7 is a flowchart illustrating an application technique 700 for applying a deep skin staple to close a wound or incision. The technique 700 includes discussion of a "tab" applicator, which extends across the deep skin staple, an array of deep skin staples, or multiple arrays of deep skin staples as a temporary backing for applying the staples. The "tab" can be adhesively coupled to the deep skin staple or a backing holding the deep skin staples to assist in handling and applying the staples to close a wound. The tab applicator can be an integral portion of the backing or a separate element. The technique 700 is also generally applicable to the application instrument 510 discussed above in reference to FIGS. 5A-6. Within FIG. 7, the deep skin staples are referenced as DS staple(s).

In this example, the technique 700 includes operations such as obtaining a deep skin staple (e.g., removing deep skin staple from packaging) at 705, positioning deep skin staple over the center of the wound at 710, pressing distal side (side opposite the tab or applicator handle) of deep skin staple into skin at 715, pulling proximal side (side to which tab attached or adjacent the applicator handle) of deep skin staple laterally across the wound at 720, pressing proximal side of deep skin staple into the skin at 725, and removing applicator tab (or application instrument) at 730. The technique 700 can optionally include additional operations such as pressing the deep skin staple into skin over wound at 735, pressing over the entire device, removing any optional backing from deep skin staple at 745, and covering the wound and deep skin staples at 750. Additional devices can be applied along the wound to close longer wounds, as indicated within the flowchart at operation 740. Further, the operations for removing the application instrument 510 discussed above in reference to FIG. 6 (e.g., operations 620 and 630) can also be optionally included in place of operations such as removing the application tab at 730. Operations 710 through 725 align with operation 610 discussed above in reference to FIG. 6.

In this example, the technique 700 can begin at 705 with the operator (e.g., physician, surgeon, nurse practitioner, physician's assistant, surgery technician, nurse, etc. . . . ) obtaining a deep skin staple or array of deep skin staples, such as by removing the deep skin staple from the packaging. In an example, the deep skin staples can be delivered in a foam or similar carrier. In this example, the deep skin staples are individually applied and include a backing with an applicator tab. Optionally, instead of a backing with an applicator tab, the deep skin staples can be delivered within the application instrument 510. At 710, the technique 700 continues with the operator positioning the deep skin staple over the center of the wound. In this example, the deep skin staple can be positioned using only the applicator tab or application instrument 510. The technique 700 can continue at 715 with the operator pressing the distal side of the deep skin staple into the skin adjacent the distal side of the wound. The distal side of the deep skin staple is opposite the side with the applicator tab or handle 540 of the application instrument 510. In discussion of the technique 700 "distal" and "proximal" are used in reference to the operator applying the deep skin staples. The distal side of the deep skin staple is opposite the side with the applicator tab or handle 540. At 720, the technique 700 continues with the operator pulling the proximal side of the deep skin staple across the wound laterally using the applicator tab or application instrument 510. Pulling the deep skin staple across the wound laterally operates to approximate the edges of the wound together. At 725, the technique 700 continues with the operator pressing the proximal side of the deep skin staple into the skin. At 730, the technique 700 continues with the operator removing the applicator tab. Alternatively, at 730, the technique 700 can optionally include operations 620 and 630 discussed above to facilitate removal of the application instrument 510. In certain examples, the operation 730 and the optional operation 745 can be combined, as the backing can be removed along with the applicator tab. In this example, operation 730 can include the operator pressing down over the deep skin staple while pulling the applicator tab in a direction transverse to the longitudinal axis of the deep skin staple to remove it.

At 735, the technique 700 optionally continues with the operator pressing over the entire deep skin staple device to ensure the legs are appropriately inserted to the desire depth on either side of the wound. At 740, the technique 700 continues with the operator determining whether additional staples are needed to properly close the wound or incision. If additional deep skin staples are needed, the technique 700 loops back to operation 705 for application of another device containing deep skin staple. If wound/incision closure is complete, the technique 700 optionally continues at 740 with the operator removing the backing from the deep skin staples. In this example, the backing is a flexible adhesive material that can be pulled off the skin and deep skin staples leaving behind just the deep skin staples. At 745, the technique 700 can optionally conclude with the operator applying a wound/incision cover of choice to protect the wound and deep skin staples during the healing process.

FIGS. 8A-8C are various views of a deep skin staple 800. In this example, the deep skin staple 800 includes two opposing staple legs 815 each affixed to an opposite end of the bridge portion 810 that includes a central spring 811. The staple legs 815 are angled at approximately 60 degrees and can include angles similar to the deep skin staples discussed above (the angle of the staple legs 815 is measured from a plane generated by an inferior surface of the bridge portion 810 and central spring 811). The staple leg angle is dictated by the degree of bend in the angled connection 816. In this example, the central spring 811 is illustrated as a circular spring but could be produced in other shapes such as ovals, diamonds, a Z-shape, an S-shape, or a W-shape, among others. The deep skin staple 800 can be readily modified to use staple legs and spring structures similar to those discussed above in reference to other deep skin staples. In an example, the two opposing staple legs 815 can each be coupled to the bridge portion 810 by spring arms. In an example, the angled connections 816 can function as spring arms. Alternatively, in another example, the angled connections 816 can be modified to include additional spring structures, such as an S-shape structure similar to those illustrated above.

Figure 9C:
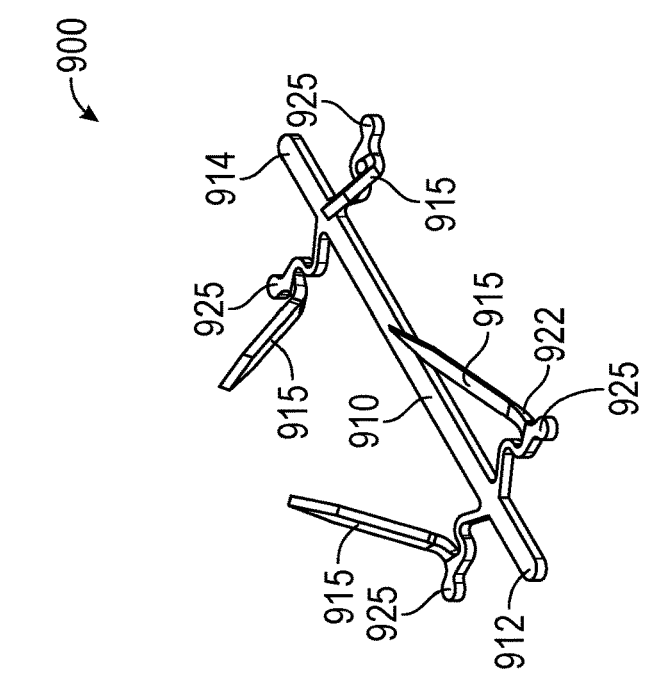
FIGS. 9A-9C are various views of a deep skin staple structure according to one embodiment of the present invention.
Figure 9B:
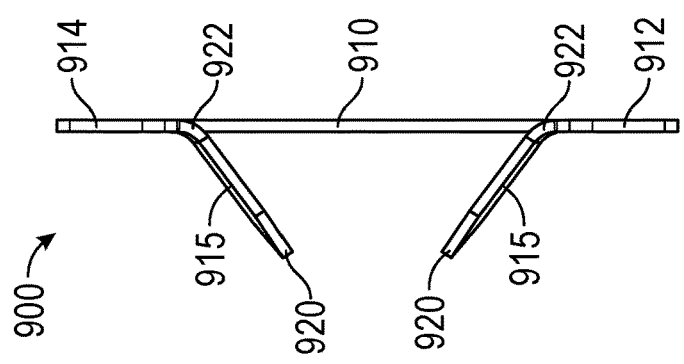
Figure 9A:
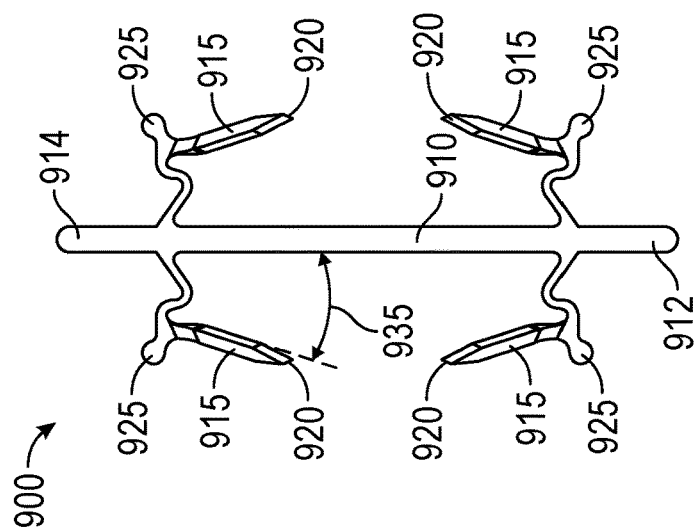

FIGS. 9A-9C are various views of a deep skin staple 900 with splayed staple legs. This example includes a deep skin staple similar to deep skin staple 100C illustrated in FIG. 1C with staple legs 915 splayed outward at an 18 degree angle from the longitudinal axis running through the bridge portion 910. The splayed laterally outward staple legs 915 can assist with retention of the deep skin staple 900 in the applied location.

In this example, the deep skin staple 900 can include a bridge portion 910 connecting opposing groups of staple legs 915 coupled to the bridge portion 910 via spring arms 925. In this example, the spring arms 925 include an s-shaped spring structure and couple to the staple legs 915 via angled connection 922 (similar to angled connection 122, but with an additional twist or bend to generate leg splay angle 935). In this example, the angled connection can be twisted or bend laterally to achieve the 18 degree splay of the staple legs 915. The staple leg splay angle 935 can be varied between 5 degrees and 25 degrees, with the example illustrated at 18 degrees. Each staple leg 915 terminates with a pointed staple tip 920. Different staple tip structures are discussed above, any of which could be incorporated into staple legs 915. The bridge portion 910 terminates on the proximal end with the proximal extension 914 and on the distal end with the distal extension 912.

Figure 10C:
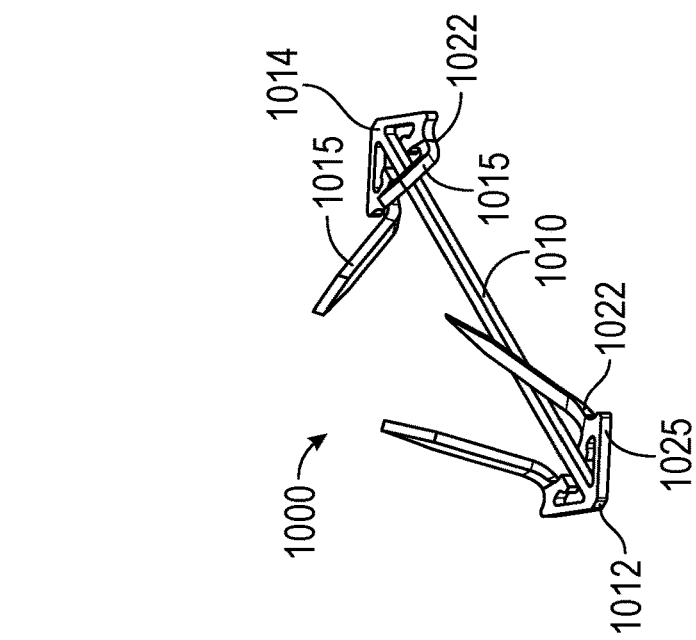
FIGS. 10A-10C are various views of a deep skin staple structure according to one embodiment of the present invention.
Figure 10B:
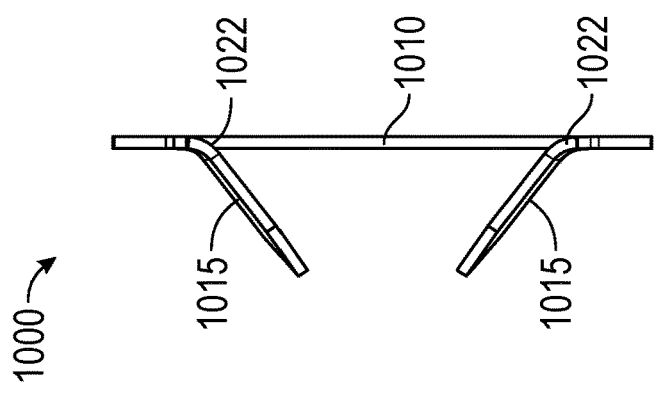
Figure 10A:
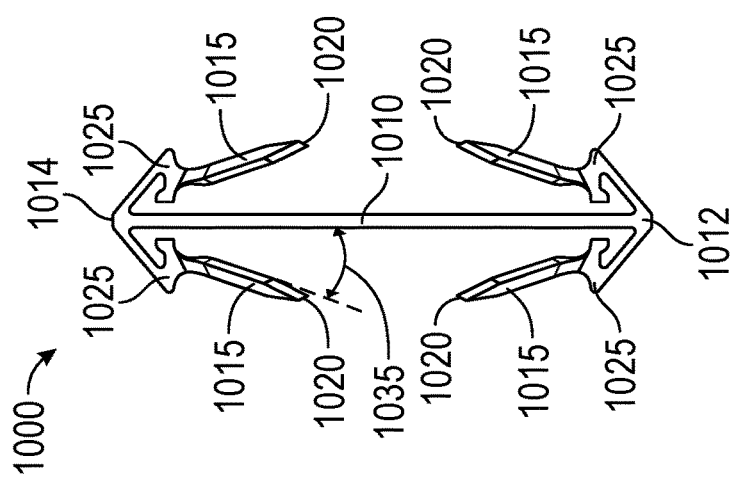

FIGS. 10A-10C are various views of a deep skin staple 1000 with a splayed staple leg structure similar to deep skin staple 900 (discussed above). In this example, the deep skin staple 400A has been modified to include staple legs splayed laterally outward at an angle 1035. The deep skin staple 1000 includes a solid bridge portion 1010 extending from a distal end 1012 to a proximal end 1014 creating a longitudinal axis of the deep skin staple 1000. In other examples, the solid bridge portion 1010 can include a spring structure, such as any of the spring structures discussed above (e.g., circular, oval, diamond, s-shaped, etc. . . . ). The bridge portion 1010 connect two opposing groups of staple legs 1015, with each staple leg 1015 coupled to a spring arm 1025 via an angled connection 1022. The spring arms 1025 form an open triangular shape with the hypotenuse extending from an end of the bridge portion 1010 and the staple leg 1015 extending from the closed side (adjacent leg of the open right triangle). Similar to deep skin staple 400A, the staple legs 1015 terminate in a pointed tip 1020. The angled connection 1022 can be twisted or bent to splay staple legs 1015 laterally outward at splay angle 1035. The splay angle 1035, similar to leg splay angle 935, is measured in a projected top view two-dimensional plane from the longitudinal axis running through the bridge portion 1010. The staple legs 1015 are also angled in a projected lateral view plane from the longitudinal axis (as illustrated in FIG. 10B).

FIGS. 11A-11E are various views of a deep skin staple 1100. In this example, the deep skin staple 1100 includes a closed frame configuration where the bridge portions are moved to the outside to form a frame around the staple legs. The deep skin staple 1100 includes bridge structures 1110A and 1110B along with central spring structures 1111A and 1111B. The proximal bridge structures 1110A run longitudinally from a proximal end 1114 to central springs 1111A and 1111B on either lateral side of the deep skin staple 1100. Continuing distally from the central springs 1111A and 1111B are distal bridge structures 1110B terminating on the distal end 1112. On either end of deep skin staple 1100 are spring arms 1125A and 1125B that hold staple legs 1115. An additional spring arm 1130 is sandwiched between spring arm 1125A and 1125B and holds a third staple leg 1115. The staple legs are coupled to the various spring arms via angled connections 1122. The central staple leg on each end extends from an M-shaped structure formed by spring arms 1125A, 1125B, and 1130. The bridge portions (1110A, 1110B) couple to spring arms 1125A, 1125B via rounded sections forming corners of deep skin staple 1100.

Figure 11B:
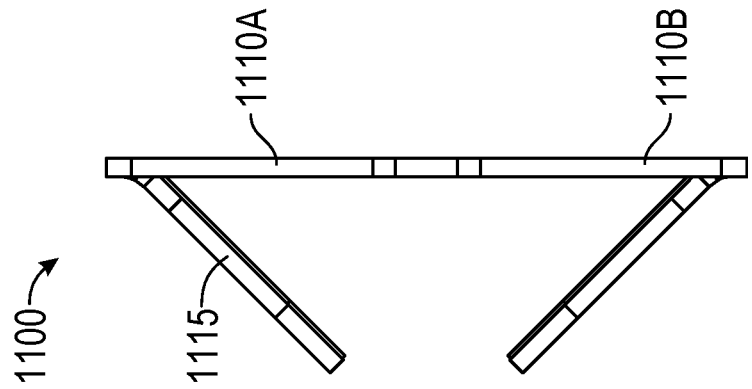
FIGS. 11A-11E are various views of a deep skin staple structure according to one embodiment of the present invention.
Figure 11A:
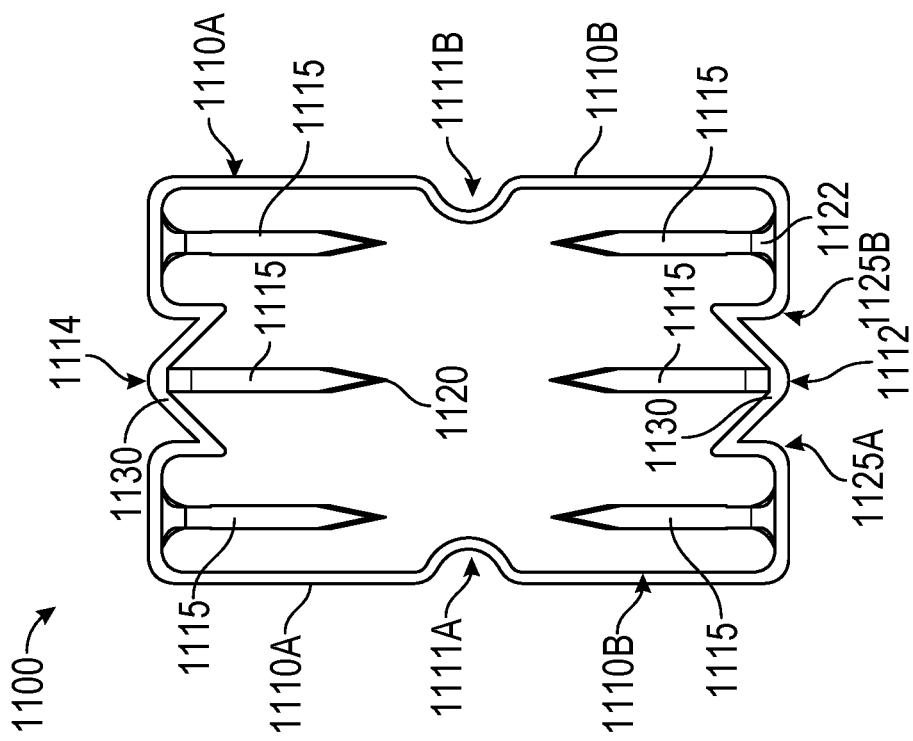
Figure 11D:
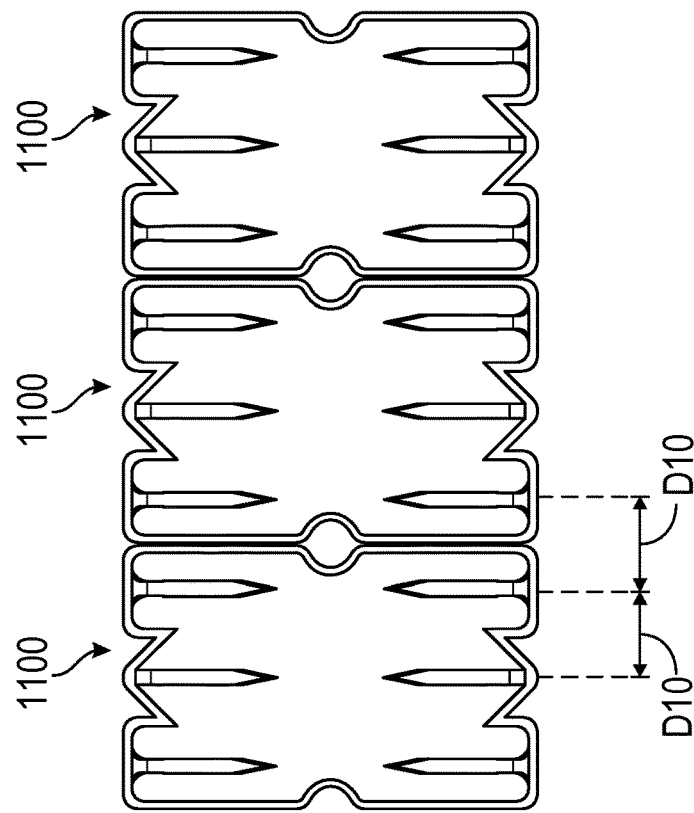
Figure 11C:
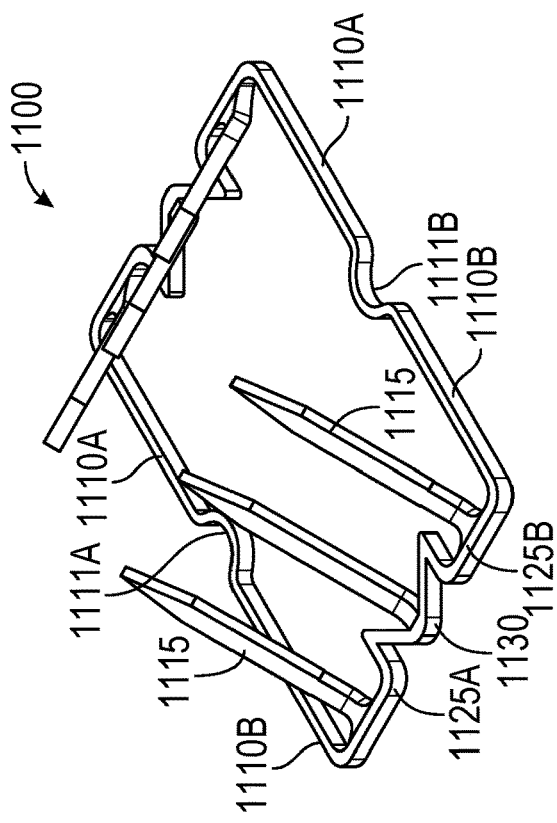
Figure 11E:
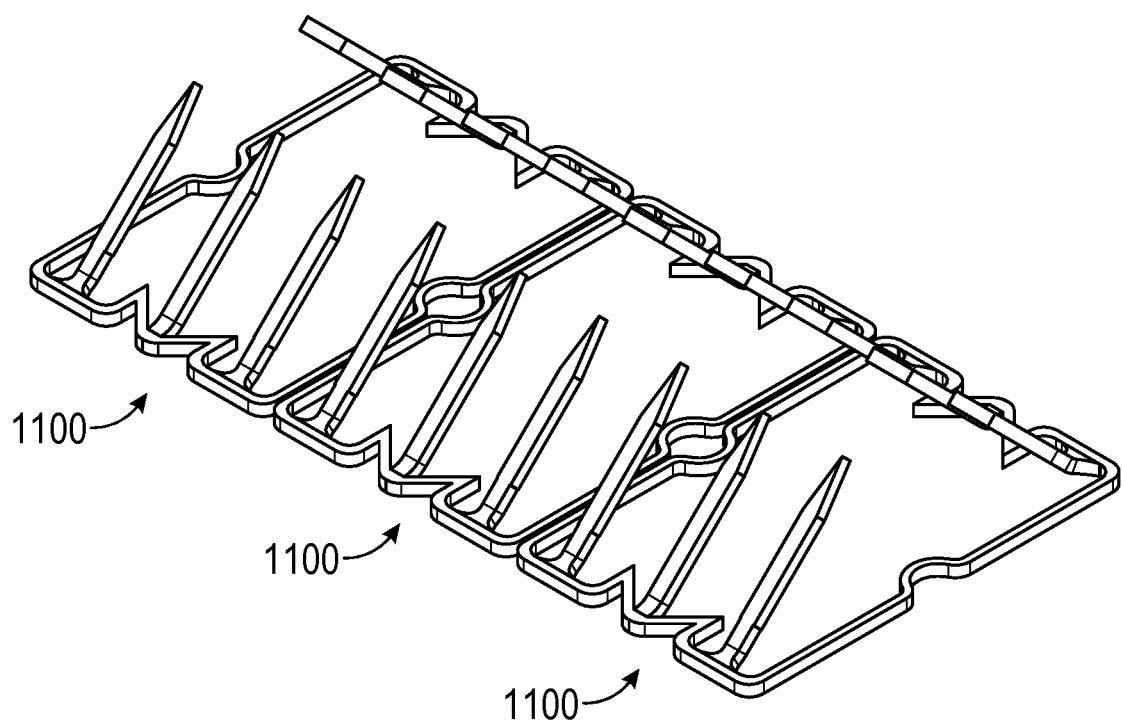

FIGS. 11D and 11E illustrate an array of deep skin staples 1100. The staple leg spacing D10 is designed to be uniform across the array of deep skin staples, as illustrated in FIG. 11D. In an example, the deep skin staples 1100 can be fused along bridge portions 1110A and 1110B between adjacent deep skin staples. Alternatively, the deep skin staples 1100 can be delivered in an array format affixed to a backing material that holds each staple in relative position. In the example with the array of deep skin staples 1100 affixed to a backing, the backing can include perforations or other separation guides to allow for easy use of as many deep skin staples 1100 as needed to close a particular wound.

Note, the terms "connection", "connects", "couples", and "coupling" are used in the description merely to describe a relationship between components, these terms are not intended to suggest that the staple 100 is or is not a single monolithic structure. The staples discussed throughout this disclosure can be a single monolithic structure. Conversely, the staple 100 can be formed from multiple parts joined together in the manufacturing process at certain connection points. As discussed in additional detail within the related applications noted above, the staples can be manufactured according to a wide variety of methods and out of a wide variety of materials. This disclosure contemplates use of similar methods and materials as discussed in reference to the staples discussed in the related applications. For example, the discussed and illustrated staples can be stamped from a suitable metal, modeled from biocompatible materials, and/or produced through an additive manufacturing process, among other techniques. Materials can include stainless steel, titanium, tungsten, nitinol, or other suitable metallic materials. Staples can also be produced out of various polymer materials, some of which may be absorbable to eliminate the need for removal.

Also note, the terms "distal" and "proximal" are used herein for one of two different purposes. In certain examples, the terms distal and proximal are merely used as relative terms to describe basic orientation. In other examples, the terms are used in their standard context to describe structures that are closer (proximal) or further (distal) from the perspective the user or from a patient's core. For example, in describing the deep skin staple 100, the structure includes a proximal extension 112 and a distal extension 114—as the devices illustrated are symmetrical the terms are merely used to differentiate the different ends. Examples of an asymmetric deep skin staple or an asymmetric applicator would result in the proximal and distal terms taking on specific meaning in reference to the person applying the deep skin staple.

Definitions

All definitions, as defined and used herein, should be understood to control over dictionary definitions, definitions in documents incorporated by reference, and/or ordinary meanings of the defined terms. Note, not all key terms are defined within the section of the specification, terms used within the specification that are not specifically defined herein should be interpreted in light of the specification and/or with their normal customary meaning.

As used herein and unless otherwise indicated, the terms "a" and "an" are taken to mean "one", "at least one" or "one or more". Unless otherwise required by context, singular terms used herein shall include pluralities and plural terms shall include the singular.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one of a number or lists of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Reference to the term "e.g.," is intended to mean "e.g., but not limited to" and thus it should be understood that whatever follows is merely an example of a particular embodiment but should in no way be construed as being a limiting example. Unless otherwise indicated, use of "e.g.," is intended to explicitly indicate that other embodiments have been contemplated and are encompassed by the present invention.

By "about" is meant a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight, or length. In any embodiment discussed in the context of a numerical value used in conjunction with the term "about," it is specifically contemplated that the term about can be omitted.

By "approximate" is meant a quantity, level, value, number, frequency, percentage, dimension, size, amount, weight, or length that varies by as much as 10, 9, 8, 7, 6, 5, 4, 3, 2 or 1% to a reference quantity, level, value, number, frequency, percentage, dimension, size, amount, weight, or length. In any embodiment discussed in the context of a numerical value used in conjunction with the term "approximate," it is specifically contemplated that the term about can be omitted.

Unless the context requires otherwise, throughout the present specification and claims, the word "comprise" and variations thereof, such as, "comprises" and "comprising" are to be construed in an open, inclusive sense, that is, as "including, but not limited to".

By "consisting of" is meant including, and limited to, whatever follows the phrase "consisting of" Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "spring characteristic" has its ordinary meaning, i.e., a characteristic that causes an object (e.g., a deep skin staple device including a central spring structure disclosed herein) to exert an opposing force against any stretching force that is applied, wherein the opposing force is related to any change in length of the object such that the object possessing a spring characteristic will retract substantially into its original resting position once the stretching force is removed. For example, in various embodiments, when a wound closure device disclosed herein as having spring characteristics is stretched (e.g., longitudinally across a wound), the spring characteristics of the device will cause the device to retract back into the device's original resting position (or substantially back into its original resting position) once the stretching force is removed. In some embodiments, the stretching and securing of the device longitudinally across a wound (see, e.g., spring arms 125, 325, 425 in all figures and spring bridge 310 in FIGS. 3A-3D) results in the retraction of the device back into its resting state after the stretching force is removed, and the result of the retraction is that the tissue (e.g., skin) to which the device is secured is stretched in a direction that opposes a tension of the skin that naturally pulls the wound apart, thus, resulting in the closure of the wound.

The term "substantially" means nearly totally or completely, for instance, 95% or greater of some given quantity (e.g., 96%, 97%, 98%, 99%, or greater than 99%, including all integers, decimals, and percent ranges between).

As used herein, the term "wound closure device" as used generally means a device used for closing a wound, a device used to evert a wound, a device used for covering a wound, a device used for protecting a wound, a wound dressing, a bandage, etc.

As used herein, the term "wound" means an injury to tissue or skin caused by scrapes, cuts, abrasion, surgical procedures (e.g., caused by minimally invasive surgery, laparoscopic surgery, robotic surgery, incisional biopsies, general surgery, and cosmetic surgery), denuded skin, burns, ulcers (e.g., diabetic ulcers, ulcers from vascular insufficiency, pressure sores, and burns), or other skin problems (e.g., allergies). Wounds may range from superficial (e.g., affecting merely the epidermis) to more traumatic (e.g., lesions which affect layers of skin or tissue at depths which are beneath the epidermis). Wounds may be of any length or shape, e.g., in some embodiments, wounds are straight, jagged, or curved.

As used herein, the term "tissue" means any human or other animal tissue including, but not limited to skin, muscle, tendon, bone, heart, lung, kidney, brain, bowel, colon, rectum, stomach, esophagus, etc.

The terms "affixed" and "attached" are used interchangeably throughout, and have their ordinary meaning, for example, a first thing (e.g., a staple) being connected or fastened to a second thing (e.g., a backing). Accordingly, other terms such as, "fastened", and "bound" may also be used in a similar manner.

The term "connected" or "interconnect" is used herein to describe when two separate things (e.g., two adjacent central spring structures or a central spring structure and legs) are in direct proximity with one another and are either affixed together or integrally connected to one another.

The term "integrally connected" is used herein to refer to two separate structures that are in direct and seamless contact with one another such that they are a single monolithic structure. Thus, reference to two "integrally connected" structures is purely for descriptive purposes, and the two structures are, in fact, one single structure.

The term "flexible" or "elastic" is meant to describe any material that is capable of sustaining a bending force without being damaged. In some embodiments, a "flexible" material comprises enough flexibility as to allow the device of the present invention to bend so as to fit the contours of the biological barrier, such as, e.g., the skin, vessel walls, or the eye, to which the device is applied. Thus, in some embodiments a material or structure used herein may comprise a material property of flexibility.

The term "grasping" is used herein to describe a staple-based anchoring of a wound closure device to its intended location on the surface of the skin or other tissue to which it is applied. The anchoring does not require penetration into the skin or tissue by the staples. For example, the wound closure device can be anchored via friction generated by the contact of the staples with the skin or other tissue. In some embodiments, the wound closure device is anchored by grasping, optionally with or without the assistance of the other various components of the present wound closure devices and systems, such as, for example, an adhesive.

The term "longitudinally" (or "along the longitudinal axis") is used herein to describe a direction on the device that extends across a wound (e.g., a laceration) when appropriately applied. Conversely, the term "laterally" (or "along the lateral axis") means the axis of the device that is perpendicular to the longitudinal axis, e.g., an axis of a device that extends parallel to a wound (e.g., a laceration) when appropriately applied according to the present disclosure.

The term "material property" means a physical property of a material making up or comprised in a wound closure device described herein. So, said another way, e.g., but not to be limited in any way, a material having a material property of elasticity is an elastic material; a material having a material property of liner spring characteristic is a material that stretches; and a material having a material property of flexibility is a flexible material.

The term "penetration" or "penetrate" is meant herein to refer to the action of piercing the skin or tissue, for example, with one or more of the staples disclosed herein.

The term "inflammation" is meant to have its ordinary medical meaning, i.e., a biological response of a tissue to a harmful stimulus. Common signs of inflammation include pain, heat, redness (erythema), swelling (edema), and loss of function.

The term "rigid" is used herein to mean that the rigid object (e.g., a bridge portion of a staple would closure device disclosed herein) does not expand.

The term "stretchable" as used herein is meant to encompass any material that can be elongated in any direction, e.g., as a result of a pulling force. "Stretchable" encompasses the term "elastic" and, thus, an object that is said to be stretchable should be understood to optionally comprise elasticity. Thus, in some embodiments, if an object is said to be stretched, this is meant to include at least two embodiments; the first being that the stretching force will be counteracted by a retractile force, and thus once the stretching force is removed, the object will inherently attempt to retract (e.g., as is the case with an elastic object). The second embodiment is one in which the object does not inherently comprise elasticity, and thus no such retractile force is inherent. In various embodiments, the devices of the present disclosure comprise both flexibility and stretchability. In particular embodiments, such devices are stretchable longitudinally. In particular embodiments, the devices are stretchable and elastic longitudinally and they are flexible.

Deep Skin Staple Manufacturing

The deep skin staple or an array of deep skin staples (collectively references below as staples(s)) comprised in the wound closure devices disclosed herein may be manufactured using any method available to the skilled artisan. In some embodiments, the staples are made by microfabrication processes that are based on established methods e.g., those used to make integrated circuits, electronic packages, and other microelectronic devices, augmented by additional methods used in the field of micromachining and micro-molding.

Deep skin staples can be fabricated, e.g., using replica molding; injection molding; microlithography; die cutting and etching; cutting; laser cutting; etching; stamping, or combinations thereof, such as have been described, e.g., in WO2007127976A2; WO2002072189A2; WO2002064193A2; U.S. Pat. Nos. 6,503,231 and 6,334,856, WO1999064580 and WO2000074763; WO2012167162, all of which are incorporated herein by reference. For example, but not to be limited, staple can be fabricated by (i) etching the staple directly, (ii) etching a mold and then filling the mold with a melt or solution comprising the staple material to form the staple product, or (iii) etching a staple master, using the master to make a mold, and then filling the mold to form the staple replica (of the master).

In various embodiments, the deep skin staples are manufactured monolithically. For example, in some embodiments, the staples are stamped from one piece of metal. Methods for utilizing this process, sometimes called micro-stamping (or stamping of small parts), are known in the art (e.g., with respect to the mass production of delicate electric circuit components, such as connectors), and, in some embodiments, they comprise using a permanent tool or a progressive die, where material (e.g., sheet metal) is fed continuously into the tool which is set up in a stamping machine. Features of the stamping machine, including cutting means (and means for removal of materials) and forming (bending) of the staples are created in multiple number of steps, or progressively. The machinery used to produce the staple 100A, 100B, 100C, 100D, 300, 400A, 400B, 400C (collectively referenced as staple or deep skin staple) can include a male component and a female component used to bend the staples to the desired angle. The tips of the staple can be bent to the desired angle either during the stamping of the staple from a sheet of metal or after the staple has been stamped. Thus, in some embodiments, the entire staple or array of staples (e.g., including all of the one or more staple portions, all of the one or more staples included on each array of staples, all of the one or more bridge portions including all of the one or more longitudinally extending portions contained therein) is monolithic. As used herein "monolithic" means produced from the same material (i.e., not individually produced and then attached), and if a structure (e.g., an array of staples) is said to be "produced monolithically" it is intended that this mean the structure (e.g., a deep skin staple or array of interconnected deep skin staples) is produced from the same material and is not individually produced and then attached or connected. For example, in some embodiments, the entire array of deep skin staples (including all of the one or more staple portions, all of the one or more staples included on each array of staples, all of the one or more bridge portions (central spring structures) including all of the one or more longitudinally extending portions contained therein) is produced monolithically (e.g., from a single sheet of metal, optionally via stamping). In other embodiments, the deep skin staples are manufactured by etching, such as, e.g., photochemical etching. In this process, raw material is masked with materials to be removed exposed. The process involves a photochemical reaction that removes the exposed materials and leaves the materials that were protected with the mask, i.e., the material with the desired geometry in a two-dimensional piece. The final array is then formed by a secondary forming process. The secondary forming process can include the use of a custom fixture to bend the staples to the desired bend radius, angle, and height.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The claimed invention includes:

1. A deep skin staple comprising: a bridge portion including an elongate section extending along a longitudinal axis of the deep skin staple; a first spring arm extending from a distal end of the bridge portion; a second spring arm extending from a proximal end of the bridge portion; a first leg coupled to the first spring arm, the first leg extending inferiorly at a first angle relative to the bridge portion and angled towards a middle of the bridge portion; and a second leg coupled to the second spring arm, the second leg extending inferiorly at a second angle relative to the bridge portion and angled towards the middle of the bridge portion, wherein, upon application to a wound, the first leg and the second leg extend into a reticular dermis layer.

2. The deep skin staple of claim 1, further comprising:
   a first set of spring arms including the first spring arm and a third spring arm extending laterally in opposite directions from the distal end of the bridge portion;
   a second set of spring arms including the second spring arm and a fourth spring arm extending laterally in opposite directions from the proximal end of the bridge portion.

3. The deep skin staple of claim 2, further comprising:
   a first set of legs including the first leg and a third leg coupled to the third spring arm and extending inferiorly at the first angle relative to the bridge portion; and
   a second set of legs including the second leg and a fourth leg coupled to the fourth spring arm and extending inferiorly at the second angle relative to the bridge portion.

4. The deep skin staple of claim 3, wherein each leg of the first set of legs and the second set of legs includes a shovel portion including a width and a length to produce a surface area perpendicular to the longitudinal axis.

5. The deep skin staple of claim 4, wherein the shovel portion terminates in a pointed tip adapted to penetrate skin.

6. The deep skin staple of claim 3, wherein the first set of spring arms includes a first spring arm extending in a first direction generally transverse to the longitudinal axis and a second spring arm extending in a second direction generally transverse to the longitudinal axis, the second direction opposite the first direction.

7. The deep skin staple of claim 6, wherein the first spring arm extends in the first direction from a position on the bridge portion directly opposite the second spring arm.

8. The deep skin staple of claim 3, wherein each of the first set of spring arms and the second set of spring arms includes a first open triangular spring arm with a hypotenuse coupled to the bridge portion and a second opposing open triangular spring arm with a hypotenuse coupled to the bridge portion.

9. The deep skin staple of claim 8, wherein the first open triangular spring arm terminates in a transverse portion coupled a first leg of the first set of legs and the second open triangular spring arm terminates in a transverse portion coupled to a second leg of the first set of legs.

10. The deep skin staple of claim 1, wherein each leg of the first leg and the second leg includes an angled connection to a respective spring arm of the first spring arm and the second spring arm.

11. The deep skin staple of claim 10, wherein the angled connection includes a reduced cross-sectional area with respect to a shovel portion of each leg.

12. The deep skin staple of claim 11, wherein the shovel portion of each leg includes an extended cross-sectional area in a direction transverse to the longitudinal axis.

13. The deep skin staple of claim 1, wherein each spring arm of the first spring arm and the second spring arm includes an S-shaped bend between the bridge portion and a leg coupled to each spring arm.

14. The deep skin staple of claim 1, wherein the bridge portion includes a spring structure.

15. The deep skin staple of claim 14, wherein the spring structure is a circular section in a middle section of the bridge portion.

16. The deep skin staple of claim 14, wherein the spring structure is a diamond shaped structure in a middle section of the bridge portion.

17. The deep skin staple of claim 1, wherein the first leg and the second leg include a vertical length in a range from 1 mm to 6 mm.

18. The deep skin staple of claim 1, wherein the first leg is angled toward a wound at an angle ranging from 20 degrees to 89 degrees when applied to close the wound, and wherein the second leg is angled toward a wound at an angle ranging from 20 degrees to 89 degrees when applied to close the wound.

19. A wound closure kit comprising:
the deep skin staple of claim 1; and
an application instrument including an opposing pair of retention wedges extending from an inferior surface and an elongate handle portion, wherein the deep skin staple is receivable between the pair of retention wedges.

20. A wound closure system comprising:
a deep skin staple adapted to modulate forces within a reticular dermis layer when applied to a wound, the deep skin staple comprising:
a bridge portion including an elongate section extending along a longitudinal axis of the deep skin staple;
a first set of spring arms extending laterally from opposite sides of a distal end of the bridge portion;
a second set of spring arms extending laterally from opposite sides of a proximal end of the bridge portion;
a first set of legs coupled to the first set of spring arms, the first set of legs extending inferiorly at a first angle relative to the bridge portion and angled towards a middle of the bridge portion; and
a second set of legs coupled to the second set of spring arms, the second set of legs extending inferiorly at a second angle relative to the bridge portion and angled towards the middle of the bridge portion; and
an application instrument including an opposing pair of retention wedges extending from an inferior surface and an elongate handle portion, wherein the deep skin staple is receivable between the pair of retention wedges.

21. The system of claim 20, wherein the application instrument includes a release notch positioned adjacent a proximal retention wedge of the pair of retention wedges on a surface of the application instrument.

22. The system of claim 20, wherein the release notch is adapted to facilitate release of the proximal retention wedge upon rotation of the elongate handle after application of the deep skin staple.

23. The system of claim 20, wherein the application instrument made from a translucent material to enable visualization of a wound during application of the deep skin staple.

24. The system of claim 20, wherein the application instrument includes a tension indicator on a superior surface configured to indicate an application tension applied to the deep skin staple.

* * * * *